(12) United States Patent
Tam-Chang et al.

(10) Patent No.: US 8,334,029 B2
(45) Date of Patent: Dec. 18, 2012

(54) MATERIALS AND METHODS FOR THE PREPARATION OF ANISOTROPICALLY-ORDERED SOLIDS

(75) Inventors: Suk-Wah Tam-Chang, Reno, NV (US); Sean M. Casey, Reno, NV (US); Isaac K. Iverson, Minnetonka, MN (US); Wonewoo Seo, Longmont, CO (US)

(73) Assignee: Board of Regents of the Nevada System of Higher Education, on behalf of the University of Nevada, Reno, Reno, NV (US)

( * ) Notice: Subject to any disclaimer, the term of this patent is extended or adjusted under 35 U.S.C. 154(b) by 0 days.

(21) Appl. No.: 13/079,731

(22) Filed: Apr. 4, 2011

(65) Prior Publication Data

US 2011/0257400 A1     Oct. 20, 2011

Related U.S. Application Data

(60) Division of application No. 12/567,673, filed on Sep. 25, 2009, now Pat. No. 7,943,208, which is a continuation of application No. 10/996,133, filed on Nov. 22, 2004, now Pat. No. 7,625,497.

(60) Provisional application No. 60/524,272, filed on Nov. 21, 2003.

(51) Int. Cl.
*G02B 5/30* (2006.01)
*C07D 221/18* (2006.01)
(52) U.S. Cl. ........................ 428/1.31; 546/26
(58) Field of Classification Search .................... 546/26; 252/585; 428/1.31
See application file for complete search history.

(56) References Cited

U.S. PATENT DOCUMENTS

| 5,405,962 | A  | * | 4/1995 | Muellen et al. | 546/27 |
| 7,625,497 | B2 | * | 12/2009 | Iverson et al. | 252/299.01 |
| 7,943,208 | B2 | * | 5/2011 | Carson et al. | 428/1.1 |
| 2010/0059716 | A1 | * | 3/2010 | Qu et al. | 252/500 |
| 2010/0072438 | A1 | * | 3/2010 | Qu et al. | 252/587 |
| 2011/0013124 | A1 | * | 1/2011 | Wang et al. | 349/96 |

OTHER PUBLICATIONS

Tam-Chang et al., "Ionic Quaterrylenebis(dicarboximide): A Novel Mesogen and Long-Wavelength Polarizing Material", Angew. Chem. Int. Ed. (2003, 42 No. 8, pp. 897-900).*

* cited by examiner

*Primary Examiner* — Shean C Wu
(74) *Attorney, Agent, or Firm* — Ryan A. Heck; UNR-DRI Technology Transfer Office

(57) ABSTRACT

The invention provides materials and methods for making anisotropic solids which may be in the form of films, layers, shaped elements, and other shaped articles. The methods provide anisotropic solids without the need for rolling, rubbing, or stretching to impart orientational alignment of the molecules of the solid. The methods employ organic or organometallic compounds which are soluble orienting molecules. The solvent or solvent system must be sufficiently volatile to be removed without disruption of the molecular orientation. The soluble orienting molecules include those containing one or more hydrophilic and/or ionic groups and the solvent or solvent system can be a polar organic solvent or solvent system or an aqueous solvent or solvent system. The invention also provides novel compounds having quaterrylene, perylene and naphthalene ring systems carrying one or more hydrophilic and/or ionic groups. These novel compounds can exhibit useful absorption and fluorescence properties in solution and in the solid phase and can exhibit useful liquid crystalline properties.

5 Claims, 8 Drawing Sheets

MATERIALS AND METHODS FOR THE PREPARATION OF ANISOTROPICALLY-ORDERED SOLIDS

CROSS-REFERENCE TO RELATED APPLICATIONS

This application is a divisional of, and incorporates by reference, U.S. patent application Ser. No. 12/567,673, filed Sep. 25, 2009 now U.S. Pat. No. 7,943,208, which application is in turn a continuation of, and incorporates by reference, U.S. patent application Ser. No. 10/996,133, filed Nov. 22, 2004, now U.S. Pat. No. 7,625,497, which in turn claims the benefit of, and incorporates by reference, U.S. Provisional Patent Application No. 60/524,272, filed Nov. 21, 2003.

STATEMENT REGARDING FEDERALLY FUNDED RESEARCH

This invention was funded in part by the United States government through the National Science Foundation grants NSF DMR 9876027 and NSF DMR0405532, NSF EPSCoR Infrastructure Enhancement Grant UCCSN-02-124. The United States government has certain rights in this invention.

BACKGROUND OF THE INVENTION

The construction of devices and materials through molecular self-assembly and self-organization processes is of considerable interest.[1-7] This invention relates to methods for controlling the self-organization of organic compounds, particularly into a lyotropic (solvent- and concentration-dependent) liquid-crystalline phase, in order to prepare micro-patterned organic solids in which molecular orientation and anisotropic (direction-dependent) properties are controlled or selected.

Patterned anisotropic solids have significant commercial applications, particularly in the fields of microelectronics and optics. Patterned inorganic semiconducting materials are generally useful in the field of microelectronics e.g. as transistors and electronic circuits. Patterned organic semiconducting materials are expected to be useful in similar applications, where the anisotropic orientation of the molecules in these organic materials can enhance the conducting properties of these materials e.g. anisotropic conducting properties. In the field of optics, patterned anisotropic solids have application as holographic films, as viewing angle-dependent optical materials, for use in stereoscopic displays, for use as polarizers, diffraction gratings, circular polarizers on retarders, waveguides, and as photonic materials.[8,9]

A wide range of methods is available for the micro- and nano-patterning of isotropic (direction-independent) materials including photolithography,[10] soft lithography,[11, 12] e-beam lithography, and scanning probe techniques.[13, 14] However, currently available methods for micro-patterning of anisotropic organic materials are limited to methods that employ either uniaxially stretched polymer films[15] or a photoalignment technique.[9] The method of the present invention generates micro-patterns and nano-patterns of anisotropic organic materials by exploiting the self-organization of organic and organometallic compounds, particularly chromonic liquid crystals on templates.

U.S. Pat. Nos. 5,405,962; 5,650,513; 5,808,073; 5,986,099; and 6,124,458 and WO 96/22332 relate to the synthesis of quaterrylenetetracarbimides and derivatives thereof. Each of these patent documents is incorporated by reference herein in its entirety to the extent that it is not inconsistent with the disclosure herein for descriptions of methods of synthesis, sources of starting materials and methods of making derivatives of quaterrylenes, as well as for structures of various art-known quaterrylene derivatives. These patents also provide descriptions of applications of certain quaterrylene derivatives.

U.S. Pat. No. 6,136,976 relates to syntheses of certain perylene-3,-4-dicarboxylic acid imides and certain applications of the compounds disclosed. U.S. Pat. No. 6,166,210 relates to certain perylene imide monocarboxylic acids and certain applications of the compounds disclosed. U.S. Pat. No. 5,948,910 relates to certain water-soluble perylene dyestuffs. U.S. Pat. No. 5,508,137 relates to certain perylene amidine imide dyes. U.S. Pat. No. 5,466,807 relates to certain perylene compounds containing sulfonic acid groups in particular, compounds based on perylene-3,4,9,10-tetracarboxylic acid monoanhydride monoimides which are substituted by alkylene- or arylenesulfonic acid groups on one or both imide nitrogen atoms, or on corresponding tetracarboxylic acid diimides, or on a halogenation product thereof which are reported to be useful as pigments and fluorescent dyestuffs as well as polymer-soluble dyestuffs. U.S. Pat. No. 4,719,236 relates to certain perylene derivatives particularly ether derivatives. U.S. Pat. No. 6,784,301 relates to certain perylene derivatives which are reported to be crystallization modifiers. Each of these patent documents is incorporated by reference herein in its entirety to the extent that it is not inconsistent with the disclosure herein for descriptions of methods of synthesis, sources of starting materials and methods of making perylene derivatives, as well as for structures of various art-known perylene derivatives. These patents also provide descriptions of certain applications of perylene derivatives.

U.S. published patent application 200424151A1 (published Feb. 5, 2004) relates to the use of functionalized perylene-3,4,9,10-tetracarboxylic acid diimides as initiator and/or co-reactant for polymerization reactions, to polymers prepared using the perylene-3,4,9,10-tetracarboxylic acid diimide compounds, to the use of the colored and/or fluorescent polymers, and to certain functionalized perylenetetracarboxylic acid diimides. This reference is incorporated herein in particular for descriptions of method of synthesis, sources of starting materials and methods of making derivatives as well as for structures of various art-known perylene derivatives.

U.S. Pat. No. 6,049,428 and references cited therein relate to dichroic light polarizers made employing dichroic dyes of a number of specific formulas. Dichroic dyes of formulas I-XXXIV therein can be employed as discussed hereinbelow in the methods of this invention to make anisotropic solids. This patent is incorporated by reference herein at least in part for its description of certain dichroic dyes. U.S. Pat. No. 6,174,394 relates to a method of making polarizers employing a polarizing coating formed from dyes having a stable liquid crystalline phase. This patent is incorporated by reference herein at least in part for its description of a method of making polarizers.

U.S. Pat. No. 6,149,857 relates to methods of making films and coatings having anisotropic conductive pathways there between.

U.S. Pat. Nos. 6,411,354, and 6,570,632 relate to alignment of lyotrophic liquid crystals. U.S. published application 2003 0154909 A1 and corresponding published PCT application WO 02/063660 relate to methods for obtaining anisotropic crystalline films and devices employed in the method. These patent documents are incorporated by reference herein at least in part for descriptions of alignment of lyotrophic liquid crystals and methods for obtaining anisotropic films which can also be employed with compounds of this invention.

Each of the following publications of the inventors hereof is incorporated by reference herein in its entirety I. K. Iverson and S-W. Tam-Chang (1999) J. Am. Chem. Soc. "Cascade of Molecular Order by Sequential Self-Organization, Induced Orientation, and Order Transfer Processes" 121:5801-5802; I. K. Iverson, S. M. Casey, W. Seo, S-W Tam-Chang (2002) "Controlling Molecular Orientation in Solid Films via Self-Organization in the Liquid Crystalline Phase" Langmuir 18:3510-3516; I. K. Iverson "Aggregation and Self-Organization of Perylene-diimide Dye Analogs into Liquid Crystalline Phases and Subsequent Order Transfer to the Solid Phase" Doctoral Dissertation, University of Nevada Reno, dated May 2002; S-W. Tam-Chang, W. Seo, I. K. Iverson, and S. M. Casey (2003) "Ionic Quaterrylenebis(dicaroxyimide): A Novel Mesogen and Long-Wavelength Polarizing Material" Angew. Chem. Int. Ed. 42(8):897-900. (Feb. 21, 2003); and T. D. Carson, W. Seo, S-W, Tam-Chang, and S. M. Casey "Novel Polarized Photoluminescent Films Derived from Sequential Self-Organization, Induced-Orientation, and Order-Transfer Processes" (2003) Chem. Mater. 15, 2292-2294.

Long-wavelength absorbing and/or emitting compounds are useful as fluorescent dyes and probes for biological studies and for sensors. These compounds also have applications in areas such as optical recording, thermally-written displays, laser printers, laser filters, infrared photography, fiber-optic communications, and optical applications in conjunction with commercially available GaAlAs lasers that emit around 780 nm. (Law, K. Y. Chem. Rev. 1993, 93, 449-486; Emmelius, M.; Pawlowski, G.; Vollmann, H. W. Angew. Chem. Int. Ed. Eng. 1989, 28, 1445-1600.) Near-Infrared (NIR) polarizers have applications as optical isolators that are used in conjunction with semiconductor lasers and fiber optics (U.S. Pat. No. 5,278,853).

There are examples of non-ionic quaterrylenebis(dicarboximide)s that absorb and emit at long wavelengths (red and near-infrared), but these compounds are soluble only in concentrated sulfuric acid (strongly oxidizing and corrosive) and chlorinated organic solvents (up to only about $10^{-2}$ M). Their limited solubility limits their processibility. (Quante, H.; Mullen, K. Angew. Chem. Int. Ed. Engl. (1995), 34, 1323-1325; Geerts, Y.; Quante, H.; Platz, H.; Mahrt, R.; Hopmeier, M.; Bohm, A.; Mullen, K. J. Mater. Chem. 1998, 8, 2357-2369.)

Thermotropic liquid-crystalline perylenebis(dicarboximide)s and lyotropic ionic perylenebis(dicarboximide)s have been previously reported. (Law, K. Y. Chem. Rev. (1993) 93, 449-486; Würthner, F.; Sautter, A.; Schmid, D.; Weber, P. J. A. Chem. Eur. J. (2001) 7, 894-902; Würthner, F.; Sautter, A. Chem. Commun. 2000, 445-446; Gregg, A. B.; Cormier, R. A. J. Am. Chem. Soc. (2001), 123, 7959-7960; Schenning, A. P. H. J.; Herrikhuyzen, J. V.; Jonkheijm, P.; Chen, Z.; Würthner, F.; Meijer, E. W. J. Am. Chem. Soc. (2002), 124, 10252-10253; Daffy, L. M.; de Silva, A. P.; Gunaratne, H. Q. N.; Huber, C.; Lynch, P. L. M.; Werner, T.; Wolfbeis, O, S. Chem.-Eur. J. (1998) 4, 1810-1815; Langhals, H. Heterocycles (1995) 40, 447-500; Holtrup, F. O.; Müller, G. R. J.; Quante, H.; De Feyter, S.; De Schryver, F. C.; Mullen, K. Chem.-Eur. J. (1997), 3, 219-225; O'Neil, M. P.; Niemczyk, M. P.; Svec, W. A.; Gosztola, D.; Gaines, G. L.; Wasielewski, M. R. Science (1992) 257, 63-65; Gregg, B. A. J. Phys. Chem. (1996) 100, 852-859; Schmidt-Mende, L.; Fechtenkötter, A.; Müllen, K.; Moons, E.; Friend, R. H.; MacKenzie, J. D. Science (2001) 293, 1119-1122; Langhals, H.; Ismael, R.; Yürük, O. Tetrahedron (2000) 56, 5435-5441; Würthner, F.; Thalacker, C.; Diele, S.; Tschierske, C. Chem. Eur. J. (2001) 7, 2245-2253; Cormier, R. A.; Gregg, B. A. J. Phys. Chem. B. (1997) 101, 11004-11006; Cormier, R. A.; Gregg, B. A. Chem. Mater. (1998) 10, 1309-1319; Liu, Z.-R.; Rill, R. L. Anal. Biochem. (1996) 236, 139-145; Tuntiwechapikul, W.; Lee, J. T.; Salazar, M. J. Am. Chem. Soc. (2001) 123, 5606-5607.)

Dichroic compounds that are commercially available as carboxylate dyes or sulfonated dyes or synthesized by the sulfonation of azo or polycyclic compounds can be used for the fabrication of dichroic thin film (absorption) polarizers by the mechanical shearing of lyotropic liquid-crystalline phases of these sulfonated dyes in the presence of surfactants and additives. (Gvon, Khan Ir.; Bobrov, Yuri A.; Bykov, Victor A.; Ignatov, Leonid Y.; Ivanova, Tatianna D.; Popov, Sergei I.; Shishkina, Elena Y.; Vorozhtsov, Georgiy N. "Thermostable and Lightfast Dichroic Light Polarizers" PCT/US94/05493. International publication number WO 94/28073; Khan, Ir Gvon; Bobrov, Yuri A.; Ignatov, Leonid Y.; Shishkina, Elena Y.; Lazarev, Pavel I.; Kurbatov, Alexey V. "Dichroic Light Polarizers" PCT/US95/14413. U.S. Pat. No. 6,049,428; Bobrov, Y. A.; Casey, S. M.; Ignatov, L. Y.; Lazarev, P.; Phillips, D.; Tam-Chang, S.-W. "Novel Dichroic Polarizing Materials and Approaches to Large Area Processing" in Flat Panel Display Materials-1998, edited by Parsons, G.; Fahlen, T. S.; Morozumi, S.; Seager, C.; Tsai, C-C. (Mater. Res. Soc. Proc., Warrendale, Pa., 1998), pp. 225-228.)

Major drawbacks of this technique for making polarizers include the required use of large quantities of highly corrosive solvents and reagents for the synthesis of sulfonate dyes making them difficult to use and expensive to dispose of; the sulfonated dyes used are often not well defined in structure; the mixtures of products is hard or impossible to separate and purify and as a result, the properties of lyotropic liquid crystals of these dyes and the optical performance of the resultant thin dichroic polarizers are hard to control and reproduce; the carboxylate dyes are not stable to storage and insoluble particles may be generated which lead to thin films with poor optical properties. Additionally, the need for surfactants and additives further complicates the optimization of the optical performance of the polarizing materials.

It is believed that this method for preparing dichroic thin film polarizers (based on the mechanical shearing of lyotropic liquid crystals) has only been used for the preparation of dichroic thin film polarizers. It has not been used, for example, for the fabrication of fluorescent polarizers.

U.S. published patent application 2004 0215015 A1 (published Oct. 28, 2004) and published PCT application WO 2004/096805 relate to certain water-soluble sulfoderivatives of perylenetetracarboxylic acid dibenzimidazole and the use of these materials to generate thin anisotropic films and optical elements based on the films. See also: T. Fiske, L. Ignatov, P. Lazarev, V. Nazarov, M. Paukshto Molecular Alignment in Crystal Polarizers and Retarders, Society for Information Display, Int. Symp. Digest of Technical Papers (Boston, Mass., May 19-24, 2002), p. 566 to 569. V. Nazarov, L. Ignatov, K. Kienskaya, Electronic Spectra of Aqueous Solutions and Films Made of Liquid Crystal Ink for Thin Film Polarizers, Mol. Mater. 14(2), 153 to 163 (2001). U.S. published application US 2004 0058091 (published Mar. 25, 2004) relates to sulfoderivatives of 1,8-naphthoylene-1',2'-benzimidazole and their use in the formation anisotropic thin films. In both published applications, the films are reported to be formed by application onto a substrate surface and oriented by any known method such as those described in PCT Publication Nos. WO 94/28073 and WO 00/25155.

U.S. published application 2003 0232153 A1 and published PCT application WO 2003/104242 relate to certain sulfoderivatives of indanthrone and their use to make anisotropic films.

Photoluminescent polarizers are an essential component of a recently developed polarization sensing technique for visual detection of analytes. In addition, photoluminescent polarizers can be used in place of the sheet polarizer and color filter combination that is employed in color liquid-crystal displays. Photoluminescent polarizers can be prepared by mechanically stretching polymers with incorporated fluorescent dyes. (Gryczynski, I.; Gryczynski, Z.; Lakowicz, J. R. Anal. Chem. (1999) 71, 1241-1251; Lakowicz, J. R.; Gryczynski, I.; Gryczynski, Z.; Dattelbaum, J. D. Anal. Biochem. (1999) 267, 397-405; Weder, C.; Sarwa, C.; Montali, A.; Bastiaansen, C.; Smith, P. Science (1998) 279, 835-837; Montali, A.; Bastiaansen, C.; Smith, P.; Weder, C. Nature (1998) 392, 261-264; Palmans, A. R. A.; Smith, P.; Weder, C. Macromolecules (1999), 32, 4677-4685.) This method, however, involves the laborious synthesis of fluorescent polymers or the impregnation of fluorescent dyes into stretchable polymers, the mechanical stretching of polymer films which limits the size of the photoluminescent polarizing films that can be produced by this method, and the additional step of mounting the polarizing film (the stretched polymer film) on the substrate of interest.

The present invention in one aspect provides materials, particularly fluorescent anisotropic materials, and methods for the preparation of anisotropic materials which can be employed as polarizers, particularly fluorescent polarizer and in other optical elements and devices/Additionally the invention provides various compounds and compositions that are generally useful as dichroic dyes and fluorescent dyes in solution and in the solid phase.

SUMMARY OF THE INVENTION

The invention provides materials and methods for making anisotropic solids which may be in the form of films, layers, shaped elements (e.g., plates, discs, slabs, etc.), and other shaped articles. The methods provide anisotropic solids without the need for rolling, rubbing, or stretching to impart orientational alignment of the molecules of the solid. The methods employ substantially organic material (which herein includes organic and/or organometallic compounds) which may be composed of a single type of organic or organometallic molecule or a mixture of one or more different organic molecules and/or one or more different organometallic molecules. The molecules or compounds which provide for orientational alignment are designated soluble orienting compounds or molecules. Soluble orienting molecules are those which are soluble in a solvent or solvent system that is appropriate for use in the methods of the invention. The solvent or solvent system appropriate for use herein must not disrupt molecular self-organization and aggregation and preferably facilitates or enhances molecule self-organization and aggregation. The solvent or solvent system must be sufficiently volatile to be removed without disruption of the molecular orientation. In preferred embodiments, the soluble orienting molecule contains one or more hydrophilic and/or ionic groups and the solvent or solvent system is a polar organic solvent or solvent system or an aqueous solvent or solvent system. In more preferred embodiments, the solvent is an aqueous solvent.

The preferred organic material employed in the preparation of the anisotropic solid is an organic or organometallic compound or a mixture of such compounds wherein at least one of the organic or organometallic components of the material possesses hydrophilic groups (e.g., hydroxyl groups or ionic functional groups, among others). More preferably at least one of the organic or organometallic components carries one or more ionic or ionizable functional groups. Preferably at least one of the organic or organometallic components is a mesogen and more preferably amphiphilic mesogen. Preferably at least one of the organic or organometallic components comprises an aromatic group. Preferred aromatic groups are perylene or quaterrylene groups and other multiple aromatic ring systems disclosed herein below. In a specific embodiment at least one of the organic or organometallic components comprises both an aromatic functional group and an ionic or ionizable group. The organic material is preferably non-polymeric. However, during processing of the organic material to form the anisotropic solid components of the organic material may be cross-linked.

In specific embodiments, at least one organic or organometallic component of the organic material is an ionic compound comprising an aromatic group. In specific embodiments, at least one organic or organometallic component is a mesogen. In specific embodiments, at least one organic or organometallic component is an amphiphilic mesogen. In specific embodiments, at least one of the organic or organometallic components is a compound of the formulas herein below. In specific embodiments, at least one of the organic components is a dichroic dye. In specific embodiments, at least one of the organic components is an aromatic fluorescent or luminescent compound.

The methods of this invention can also employ soluble orienting molecules that have been shown in the art to form anisotropic solids using art-known photoalignment techniques and/or mechanical shearing techniques. In specific embodiments, Further, the methods of this invention can also employ derivatives containing one or more hydrophilic groups, including ionic derivatives, e.g., hydroxylated, carboxylate, amine or ammonium derivatives, of compounds that have been shown in the art to form anisotropic solids using art-known photoalignment techniques and/or mechanical shearing techniques.

The method can employ monomeric, dimeric and/or oligomeric mesogens. The method preferably employs monomeric mesogens. Mesogens can include organic and/or organometallic species. The method preferably employs organic mesogens which exhibit lyotrophic liquid-crystalline phases in a selected solvent or solvent system at selected mesogen concentrations. The method preferably employs mesogens that exhibit lyotropic chromonic liquid-crystalline phases in a selected solvent or solvent system at selected mesogen concentration. The liquid crystalline phases exhibited by mesogens can also be affected by temperature and the presence or absence of surfactants and inorganic salts.

The solvent or solvent system employed may be aqueous, organic or a mixture thereof. Solvents that can be employed include, among others, water, various aqueous solutions (of selected pH or of varying pH), alcohols, aqueous alcohol mixtures, organic acids (e.g., formic acid or trifluoroacetic acid) or aqueous organic acid mixtures (e.g., HCOOH/water mixtures). Organic solvents, particularly polar organic solvents, such as alcohols and DMSO, can also be employed. Solvents can include mixtures of water and any organic solvent at a concentration such that it is miscible with the water.

The method of this invention comprises the steps of:
providing a solution of an in organic or organometallic compound (preferably a mesogen) in an isotropic phase or in a lyotropic liquid-crystalline phase;

contacting a template which has at least one dimension that is micro-scaled, i.e., having at least one dimension that is less than 100 microns or nano-scaled having at least one dimension that is less than 1 micron; and removing sufficient solvent from the isotropic solution to form an anisotropic solid containing anisotropically oriented molecules.

The solution employed may be an isotropic solution or the solution may comprise a liquid crystalline phase, e.g., a lyotropic liquid crystalline phase. On removal of a portion of the solvent, an isotropic solution may form a liquid crystalline phase and on further removal of solvent form the anisotropic solid. Alternatively, on removal of sufficient solvent, an isotropic solution may directly form an anisotropic solid (i.e., an LC phase may or may not be an intermediate in the formation of the anisotropic solid.) When the solution employed comprises an LC phase removing sufficient solvent forms an anisotropic solid containing anisotropically oriented molecules. Preferably the solution employed comprises at least about 1% by weight of one or more soluble orienting molecules.

The rate of solvent removal from the solution is selectively controlled to allow and not disrupt orientation of the ionic organic and/or organometallic components of the solution. Dependent upon the concentration of the solutions and the solvent used, solvent may be removed over a time period of minutes to hours. Additionally, the temperature of the template may be selectively controlled during solvent removal to facilitate orientation of the mesogens.

The method is generally applicable to mesogens which exhibit lyotrophic liquid-crystalline phases, particularly chromonic lyotrophic liquid crystal phases and is specifically applicable to mesogens which exhibit ribbon-like or fiber-like structures in the LC phase. The presence of ribbon-like or fiber-like structures in the LC phase can be determined using any known method and particularly using the methods in the Examples herein.

In a specific embodiment, the solvent employed is an aqueous solvent (e.g., water, water/alcohol mixture, etc.). In a more specific embodiment, the solvent is water. In another specific embodiment, the solvent is a mixture of organic acid ($HCOOH$ or $CF_3COOH$, for example) and water.

In a specific embodiment the template is positioned in contact with a substrate such that the anisotropic solid formed by solvent removal is formed in contact with the substrate. The method allows formation of a unitary solid, for example in the form of a layer or structured layer. The composition of the anisotropic solid can be uniform. The method also allows for the formation of an anisotropic solid having a complex structure or pattern in which portions of the solid have different compositions.

In a further specific embodiment, the method is employed to form a plurality of micro-scaled or nano-scaled structures on a substrate (e.g., channels or ridges). In another specific embodiment, the method is employed to form a plurality of micro-scaled structures on a substrate in which one or more of the plurality of micro-structures are formed from different mesogens. Complex two and three dimensional micro-patterns of different mesogens on a substrate can be generated by the methods of this invention.

In one exemplary embodiment, complex micro-patterns or nano-patterns of two or more colored solids that polarize light can be formed on selected substrates. In this embodiment, structures on the substrate are formed using two or more solutions which contain ionic species, particularly mesogens, which absorb light at different wavelengths. A plurality of micro-scaled structures, at least some of which are composed of ionic species, particularly mesogens, that absorb at different wavelengths, can be formed on a substrate.

In another exemplary embodiment, micro-patterns are developed simultaneously on two surfaces of the substrate. In this embodiment, the substrate is sandwiched between two templates, which have the same or different patterns of microfeatures. The templates may or may not be aligned on opposite surfaces of the substrate. The relative positions or orientations of the templates which sandwich the substrate may be selected to achieve a desired relative positioning of anisotropic solid patterns on either side of the substrate. The relative position or orientation of structural features (e.g., lines, ridges, channels, etc.) of the two templates may be selected to achieve a desired relative positioning or orientation of those features on the substrate surfaces. For example, using templates to provide line features on a substrate, the angle between the line patterns of the two templates which sandwich the substrate may be selectively varied from 0° to 90°.

In another exemplary embodiment, complex patterns of anisotropic solid may be generated on a substrate by formation of multiple layers of anisotropic solids or patterned solids. A first layer of anisotropic solid or patterned solids is formed by filing a template in contact with a substrate with a solution containing an ionic organic or organometallic compound (preferably a mesogen) and removing solvent to form the solid on the substrate. A second layer of anisotropic solid or patterned solids is formed by filing a template, in contact with the first anisotropic layer formed, with a different solution containing a different ionic compound and thereafter removing solvent to form a second layer of anisotropic solid or patterned solid. The second solvent can be selected so that it does not substantially dissolve the ionic compound of the first layer. Alternatively, the ionic compound of the first layer can be cross-linked or polymerized prior to generation of the second layer. Multiple templates can be used to generate multiple layers of anisotropic solid or patterned solid on the substrate. Each layer formed can have the same or different structural features or pattern. Each layer formed may be composed of the same or different ionic compounds. The relative positioning or orientation of templates used to form adjacent layers can be selected to achieve a desired two or three dimensional pattern. For example, if templates containing line features are used to form layers, the angle between the line patterns of templates used to form adjacent layers may be selectively varied from 0° to 90°.

In a specific embodiment, the hydrophilic or ionic organic or organometallic compound (e.g., a mesogen) contains latent functional groups that can be used to polymerize or cross-link aligned ionic organic or organometallic compounds in the anisotropic solid formed by solvent removal prior to or after release or removal of the solid from the template. Cross-linking may be selectively triggered by a change in condition, such as irradiation with light of a selected wavelength, a change of temperature or the like. A cross-linking group and/or catalyst may be may be added to the mesogen solution to facilitate selective cross-linking. Examples of crosslinking included among others, a thiol group that can oxidized by iodine vapor or oxygen in air to form disulfide bonds or an acrylamide or an acrylate group that polymerizes upon UV irradiation or in the presence of a catalyst.

In a specific embodiment, one or more of the compounds in the solution contains a group or moiety that exhibits dichroic properties (direction-dependent absorption of light). In a specific embodiment, one or more of the organic compound in the solution is a dichroic dye.

In a specific embodiment, one or more of the soluble orienting organic or organometallic compounds in the solution contains a group or moiety that exhibits fluorescence, phosphorescence or electrochemiluminescence. In a specific embodiment, one or more of the ionic organic or organometallic compounds in the solution is a fluorophore.

In a specific embodiment, one or more of the soluble orienting organic or organometallic compounds in the solution contains a group or moiety that exhibits semiconducting properties. In a specific embodiment, one or more of the compound in the solution is a semiconductor.

In a specific embodiment, one or more of the soluble orienting organic or organometallic compounds in the solution contains a group or moiety that exhibits photoconducting properties. In a specific embodiment, one or more of the compound in the solution is photoconducting.

The method of this invention can employ solutions of mesogens which are lyotrophic liquid crystals. The method has been exemplified with certain chromonic lyotrophic liquid crystals, including perylenecarboximides, perylene mono (dicarboximides), perylene bis(dicarboximides), quaterrylenecarboximides, quaterrylenebis(dicarboximides), naphthalene monocarboxylmides, naphthalene mono(dicarboximide) monocarboxylmides. Additionally, azo-dyes and cyanine dyes that are lyotrophic liquid crystals can also be used to make anisotrophic solids using the method of this invention. In specific embodiments, pinacyanol chloride (a commercially available cyanine dye) and derivatives thereof can be employed in the methods herein to make anisotropic solids. In other specific examples, C.I. direct blue 67 and derivatives thereof (examples of azo dyes) are chromonic LC mesogens that can be used in the preparation of anisotropic materials by the methods herein. In other specific examples, dichroic dyes can be employed in the methods herein to make anisotropic solids.

In a specific embodiment the mesogens employed in the methods herein are compounds or salts of formulae I, II, III, IV-1, IV-2, VI-1 and VI-2 as described in more detail below.

The invention further provides kits for making anisotropic solids or for forming an anisotropic layer on a substrate. The kits comprise one or more hydrophillic or ionic orienting compounds, in particular, one or more of any of the hydrophillic orienting compounds of formulas I-VI below. The ionic orienting compound(s) may be provided as solids or in solution. The compounds may be provided in reweighed aliquots for use in one or more preparations. Additives as discussed herein may be included in the kit or in solutions within the kit. A kit may be provided with one or more templates, useful or one or more applications. The templates may be disposable or reusable. The kit can include instructions for carrying out the method.

The invention also provides novel compounds of the formulas hereinbelow which are useful in general as absorption dyes and fluorophores in solution, liquid-crystalline phases and in solid phase. Additionally, novel compounds herein can be employed as dyes, liquid crystals or components of liquid crystals. Certain of the molecules described hereinbelow are useful as fluorescent probes and labels in chemical and biological studies. More specifically, various compounds disclosed herein are useful for making fluorescent and anisotropic materials, for making anisotropic solids and are particularly useful for making such solids which have desirable optical and/or electrical properties. For example, certain compounds disclosed herein exhibit changes in optical or emission properties on interaction with or binding to nucleic acids and as such can be employed in assays for the detection of nucleic acids.

Other aspects of the invention will be illucidated on review of the figures, detailed description and examples.

As illustrated in a preferred embodiment, concentration of the isotropic solution containing the hydrophobic orienting molecules that are chromonic mesogens results in the formation of ribbon-like chromonic liquid crystals (4).

Figure 2A:
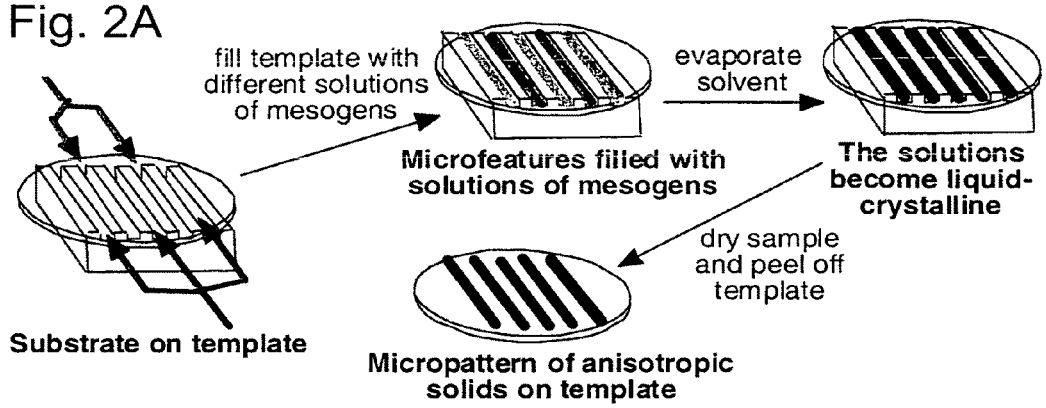
Figure 2B:
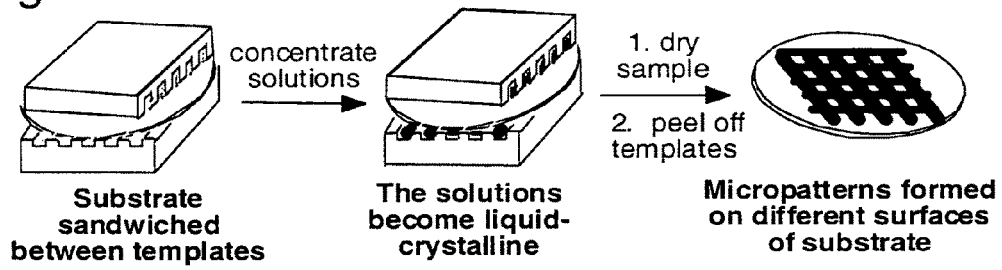
Figure 2C:
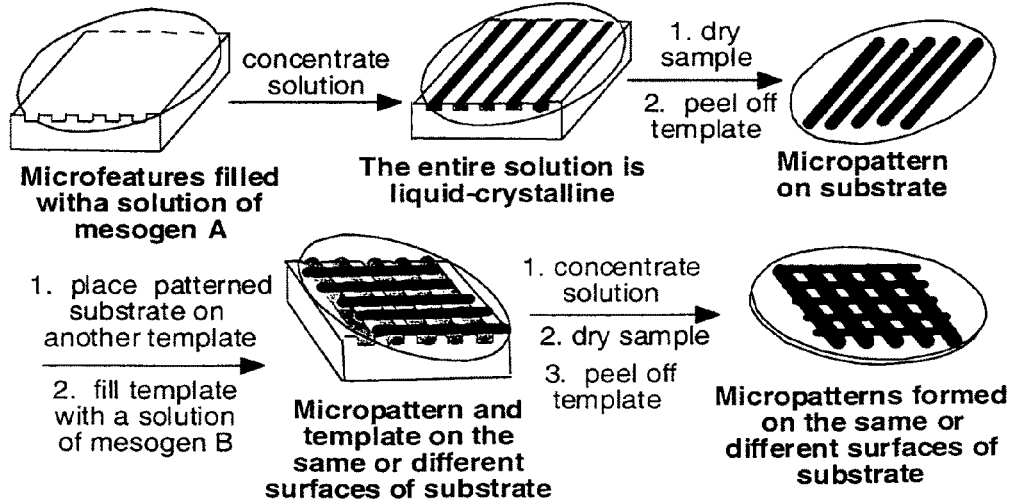

FIGS. 2A-2C are schematic representations of several exemplary methods for generating complex micropatterns of anisotropic solids. In FIG. 2A a parallel approach to micropatterns of multiple mesogens on the same surface of a substrate is illustrated. In FIG. 2B a sandwich approach leading to micropatterns formed simultaneously on different surfaces of a substrate is illustrated. In FIG. 2C a stepwise approach to micropatterns of multiple mesogens formed sequentially on the same or different surfaces of a substrate is illustrated.

Figure 3:
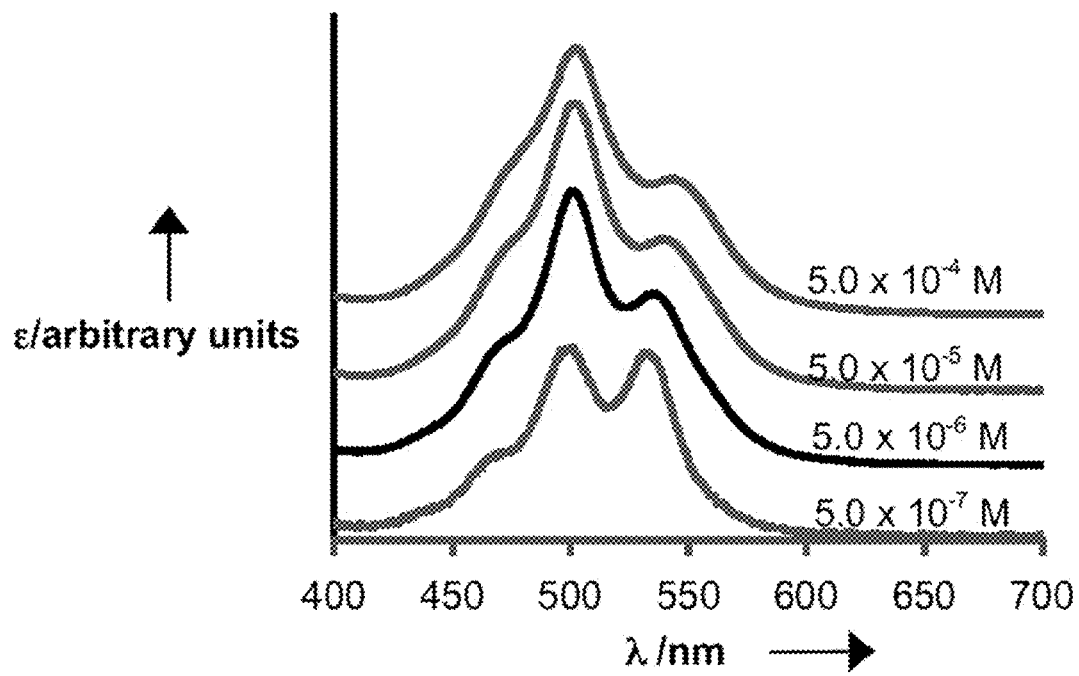

FIG. 3 illustrates offset visible absorption spectra of compound VIIi in water at 25° C. showing the dependence of the electronic absorption properties on the concentration of compound VIIi.

Figure 4A:
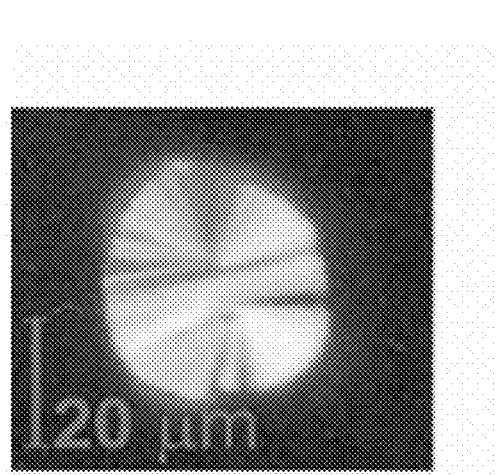
Figure 4B:
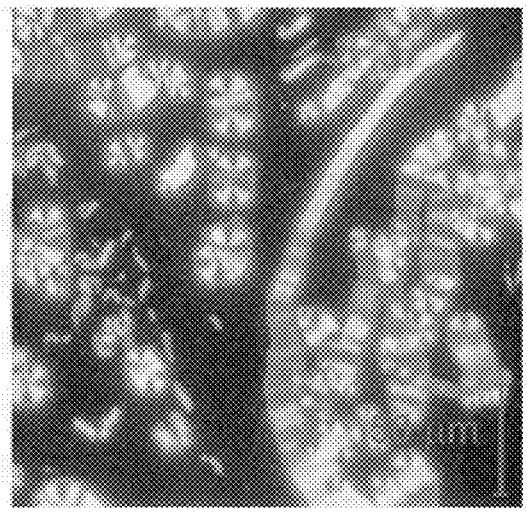
Figure 4C:
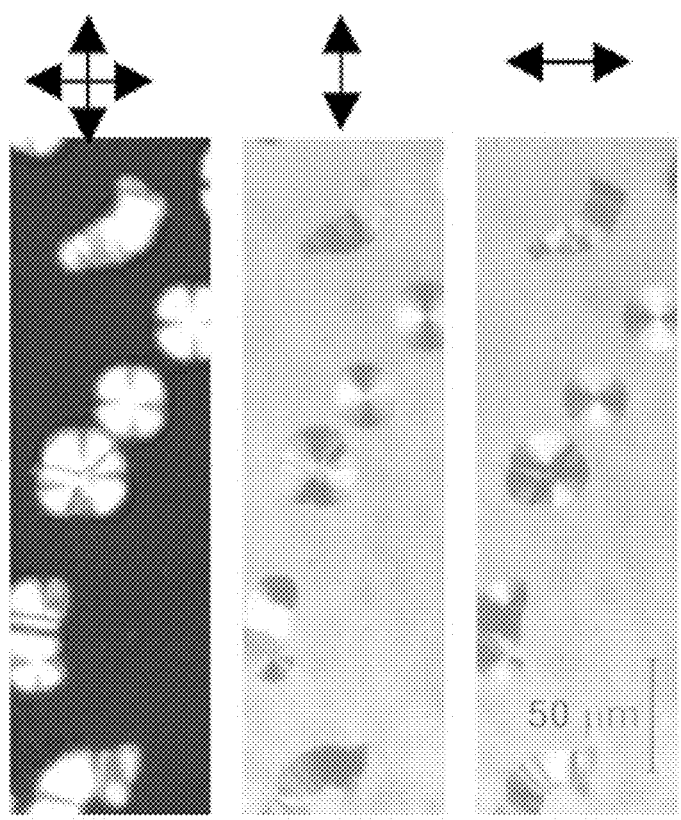

FIGS. 4A-C are optical micrographs showing the development of anisotropically oriented VIIi. FIG. 4A shows a chromonic liquid-crystalline phase developed from an isotropic solution of VIIi (~20 wt. % in water) viewed between crossed polarizers. FIG. 4B shows the growth of long ribbon-like chromonic liquid-crystalline structures view through crossed polarizers. FIG. 4C shows three views of the mesogens (VIIi) in the ribbon-like region between cross-polarizers (left) and between orthogonal polarizers (middle and right) demonstrating that the mesogens are anisotropically oriented.

Figure 5:
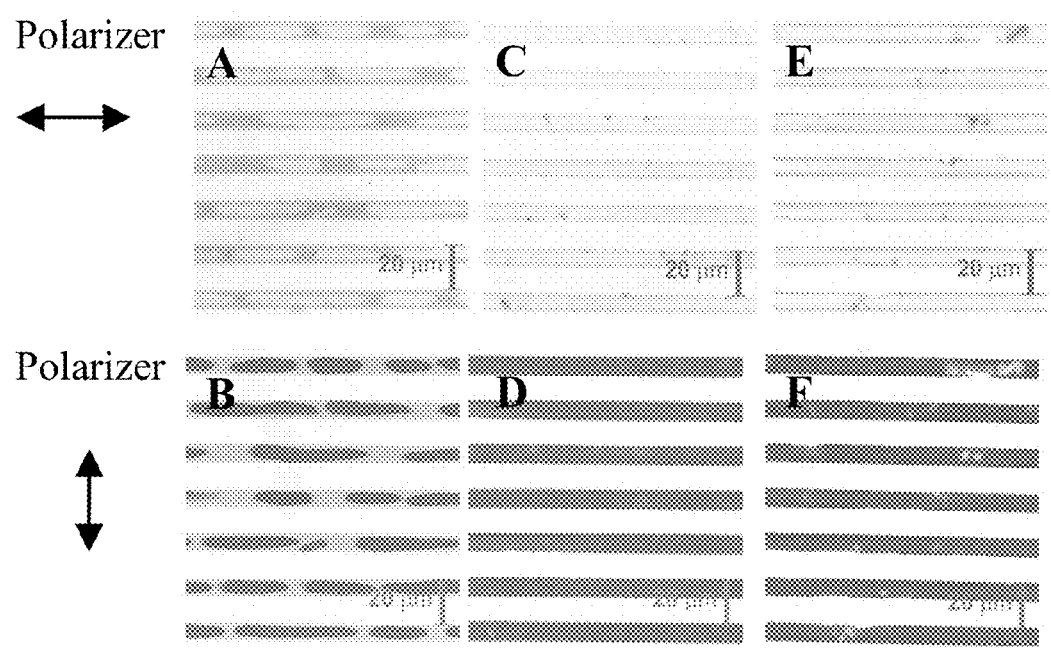

FIG. 5 illustrates optical micrographs showing: (A and B) ribbon-like liquid-crystalline structures that were developing slowly from an isotropic solution of compound VIII on a PDMS template, (C and D) the solution on the PDMS template was completely liquid-crystalline and anisotropically oriented, and (E and F) the anisotropic solid of compound VIIi on a glass cover-slip after the sample was dried and the PDMS template was peeled off. As indicated, the polarization axis of the incident light for A, C and E was parallel to the patterned lines, while that for B, D and F was perpendicular to the patterned lines.

Figure 6:
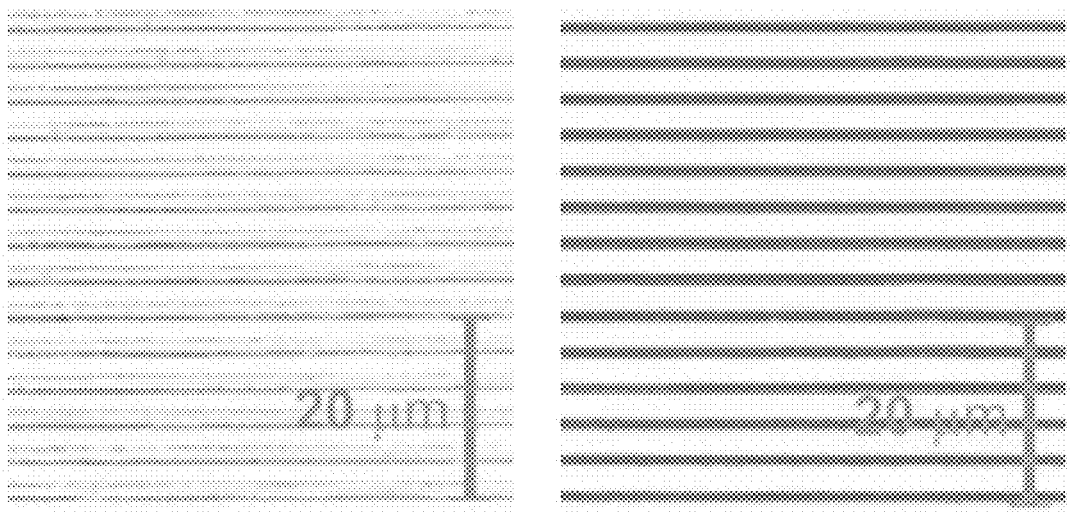

FIG. 6 illustrates optical micrographs showing anisotropic orientation of compound VIIi in a pattern of 2-µm lines on a glass cover-slip. The polarization axis of the incident light was parallel (left view) or perpendicular (right view) to the patterned lines. The patterned lines in the left view appear as light pink in color, while those in the right view are intense red in color.

Figures 7A, 7B:
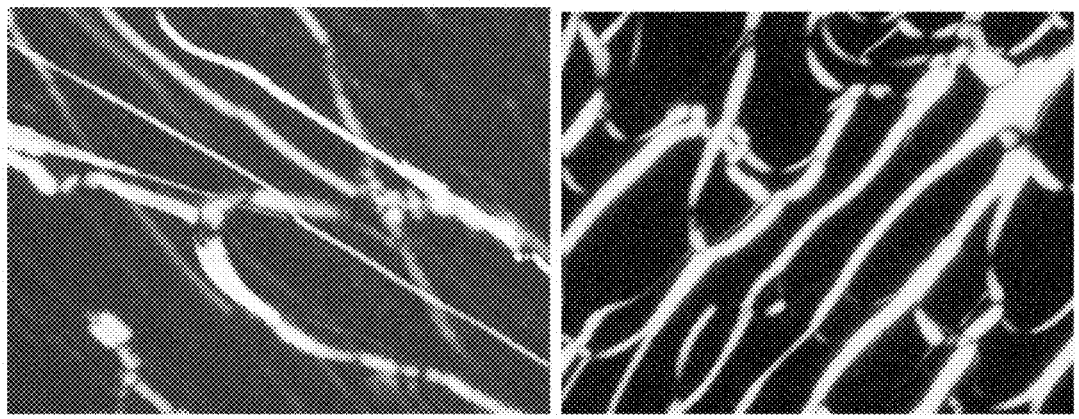

FIGS. 7A and 7B are optical micrographs. FIG. 7A shows the fiber-like chromonic LC structures developed from a solution of IIIb (4.9 wt. % in 5 vol % formic acid) on a glass substrate without a template. FIG. 7B shows the ribbon-like chromonic LS structures developed from a solution of IVe (2 wt % in 5 vol % formic acid) on a glass substrate without a template. Both samples were viewed between crossed polarizers.

Figure 8A:
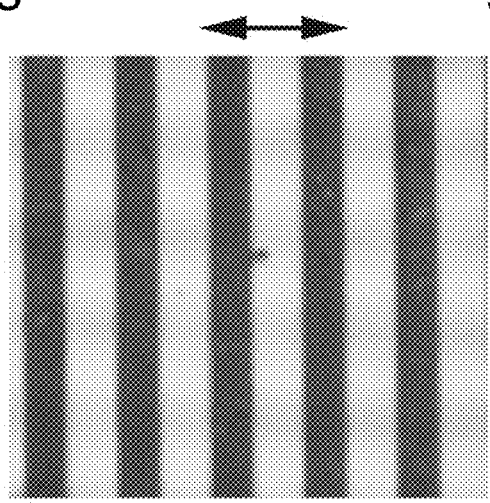
Figure 8B:
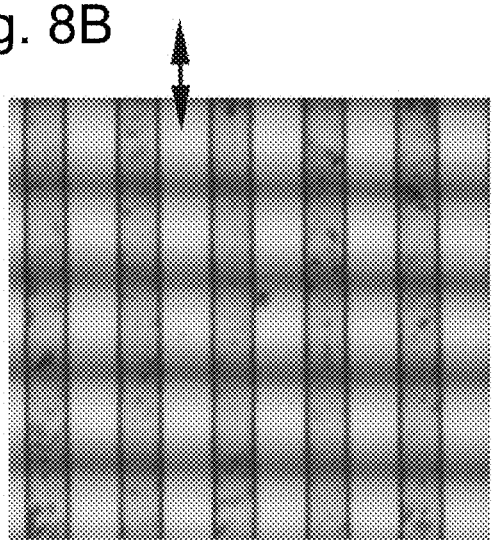
Figure 8C:
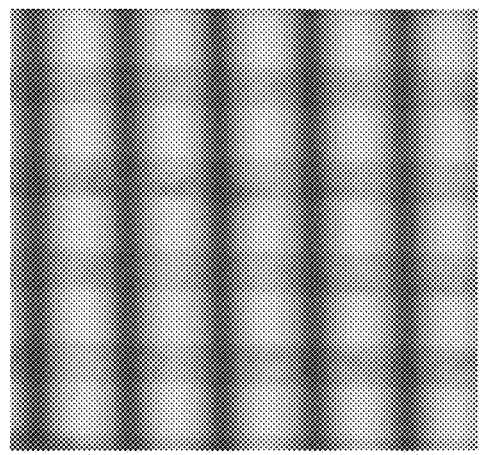
Figure 8D:
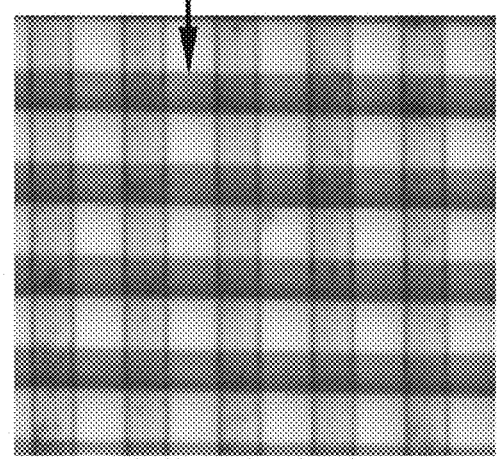

FIGS. 8A-D are optical micrographs of the double-sided sample prepared as described in Example 13 when the sample was viewed through a single polarizer. The micrographs show the anisotropic orientation of IIIb and IVe in micropatterns of line features (~20 μm in linewidth) on the opposite sides a glass cover slip. The images (FIG. 8A) and (FIG. 8B) were focused at side 1 and the images (FIG. 8C) and (FIG. 8D) were focused at side 2. The polarization axis of the incident light was perpendicular to the lines of IIIb in (FIG. 8A) and (FIG. 8C) and parallel to the lines of IVe in (FIG. 8C) and (FIG. 8D).

DETAILED DESCRIPTION OF THE INVENTION

In one aspect the invention relates to a method for making anisotropic solids. In another aspect the invention relates to compounds exhibiting useful UV-visable, and/or near-IR absorptions and/or fluorescence and/or liquid crystalline properties.

Figure 1:
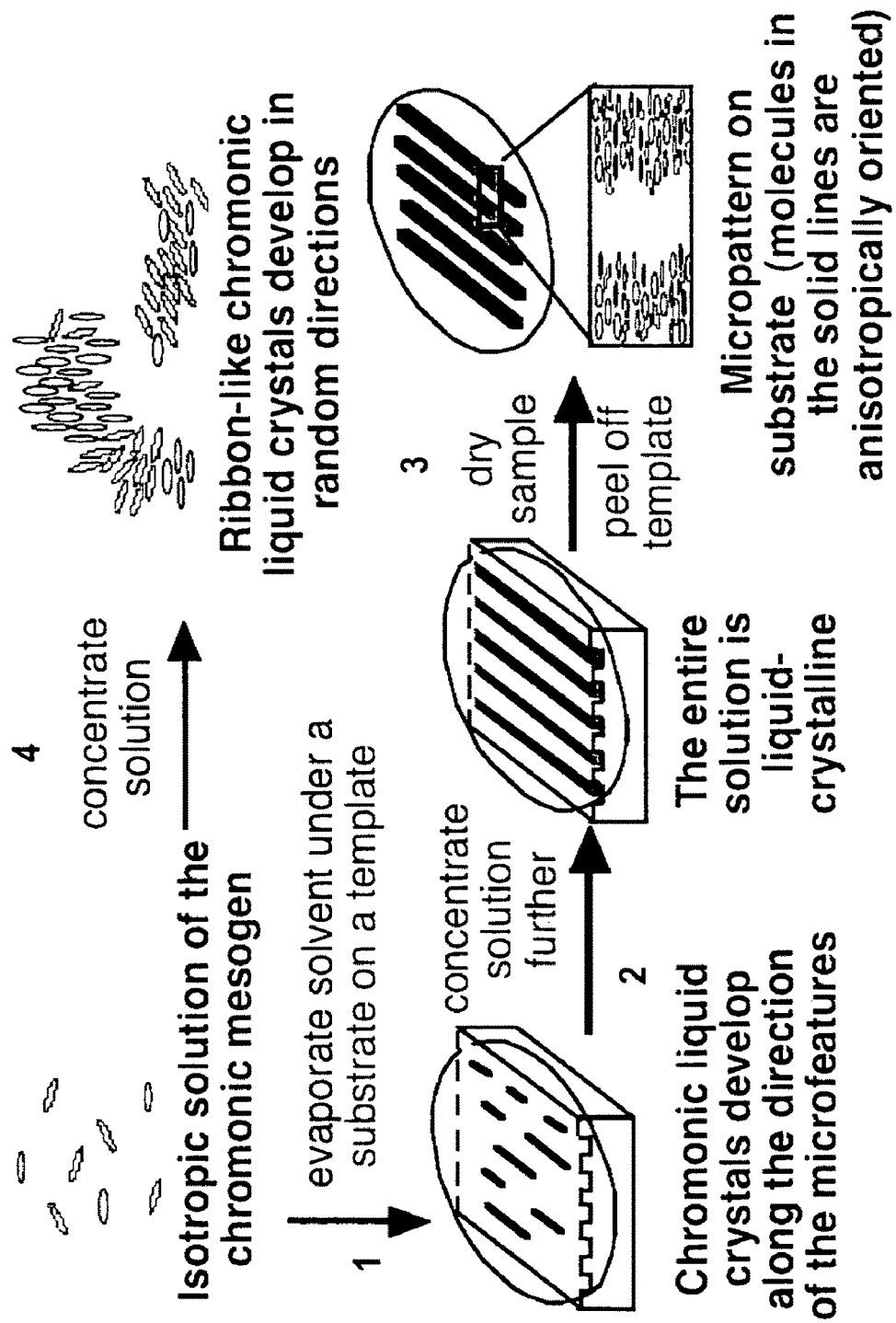
FIG. 1 is a schematic representation of templated-guided generation of a micropatterned anisotropically ordered solid exemplified employing chromonic liquid crystal mesogens. A template having microfeatures (uniform linear channel 8are illustrated). An isotropic solution is placed in contact with the microfeatures of the template and a substrate upon which the anisotropically oriented solid is to be formed and solvent is evaporated from the solution so that liquid crystals develop along the direction of the microfeatures (1). Further concentration by solvent removal results in the formation of anisotropicallly-oriented liquid crystals in a micropattern (2). The template can be removed to provide the micropattern of anisotropically oriented solid on the substrate (3).

The method of the present invention is illustrated in FIG. 1. In the method illustrated, a soluble orienting organic or organometallic compound which can be an organic or organometallic compound having one or more hydrophilic or ionic groups (which preferably is a mesogen, particularly an amphiphilic mesogen and more preferably is a lyotropic liquid-crystalline mesogen) and which is soluble in aqueous or organic media (solvents or solvent systems) is used to form an anisotropic solid. The soluble orienting compound is organic or organometallic and preferably contains appropriate functional groups to enhance its solubility in a selected solvent or solvent system. A solution of the soluble orienting compound is introduced into a template (mold or die). The template preferably has at least one dimension or structural feature that is micro-scaled or nano-scaled.

Solvent is removed from the solution in contact with the template so that aggregation of the soluble orienting compound occurs (the solvent is removed in such a way and at such a rate that orientation is not significantly disrupted). Noncovalent intermolecular interactions of the soluble orienting compound including Van de Waals interactions, π-stacking and/or entropically driven hydrophobic interactions are believed to drive molecular aggregation.

In a preferred embodiment, the soluble orienting compound is a mesogen, particularly an amphiphilic mesogen. The solution can initially be isotropic, so that solvent removal generates a lyotropic liquid-crystalline phase[16-20] in which the mesogens self-organize into liquid-crystalline domains. The mesogens in such LC phases possess liquid-like mobility and yet retain long-range orientational order. In some cases, the LC phase comprises ribbon-like or fiber-like structures of aggregated mesogens. It is believed that the template with micro-scaled or nano-scaled dimensions or features serves to guide the long range structure the liquid-crystalline aggregate to generate anisotropic orientation.

Upon continued evaporation of solvent from the solution containing LC domains in which the mesogens are anisotropically oriented an anisotropic solid forms in the template conforming to the structural features of the template. During solvent removal, the entire solution becomes liquid-crystalline and anisotropic, and the sample is dried to yield a micro-patterned anisotropic solid of the mesogen. Alternatively, the initial mesogen solution added to the template may be sufficiently concentrated so that desirable LC domains are already present. In this case, solvent removal will also result in the formation of an anisotropic solid.

Thus, it is believed that in the method herein a cascade of molecular order is generated starting with an isotropic solution (or solution containing some measurable level of LC domains) and ending with a well-defined micro-pattern or nano-pattern of the anisotropically ordered solid. The micro-pattern or nano-pattern of the anisotropic solid formed in the template can be transferred to a substrate by removing the template.

There are many important benefits of the use of the method of this invention. The anisotropic features are believed to be formed by the self-aggregation of molecular constituents into anisotropically ordered ensembles, a "bottom-up" approach, so that the minimum size of the features that can be obtained should only be limited by the size of the molecular aggregates. For orienting compounds that form single-molecule wide aggregates, the width of the aggregates can be as small as 10-20 Å. With the use of an appropriate template, the fabrication of micro-scale (i.e., having at least one dimension that is about less than 100 μm) or nano-scale (i.e., having at least one dimension that is less than 1 micron) patterned anisotropic materials can be produced. By design of the molecular structure of the orienting compound, optical and physical properties of the resultant anisotropic solid can be adjusted to achieve materials having desired combinations of properties.

For example, the conductivity of the solid can be affected by selection of molecular structure. Semiconducting or photoconducting properties of the anisotropic material can be controlled at the molecular level. The methods herein can be used to prepare single or multiple layers of anisotropic solid as well as more complex patterns of the anisotropic solid. For example, line patterns aligned in different directions, line patterns employing different mesogens; line patterns on opposite surfaces of a substrate; combinations of patterns using two or more templates; and the overlay of multiple patterns (which may be the same or different) using one or more templates can all be achieved by the methods herein. By using non-planar templates and/or interwoven micro-channels or nano-channels[21] to guide the organization of the chromonic liquid crystals, 3-dimensional patterns of anisotropic materials may be formed.

In general, the method involves the preparation of a solution of one or more soluble orienting molecules in a solvent or solvent system. The solvent or solvent system is selected such that it can be removed by any known method that does not disturb ordering of the hydrophilic orienting molecules as the solvent or solvent system is removed. Solvent is preferably removed without mixing, stirring or other agitation. Vacuum and or mild heating may be applied to facilitate solvent removal. Heating applied should not disrupt the molecular orientation that develops on solvent removal. In a specific embodiment, the temperature of the system may be controlled to facilitate and maintain the desired molecular orientation of the soluble orienting molecules. As illustrated herein, soluble orienting molecules can be substituted with one or more functional groups which enhance their solubility in a given solvent or solvent system.

In a specific embodiment the concentration of the soluble organic and/or organometallic compounds (or combined concentration of a mixture of hydrophillic and/or ionic organic and or organometallic compounds) in the solution introduced into the template is between about 1 wt. % to about 65 wt. % and any subranges thereof. Certain isotropic solutions used in the methods herein can have concentrations of the ionic organic or organometallic compounds that form the anisotropically oriented component of the anisotropically oriented solid ranging from about 0.5 wt. % to about 45 wt. %. (including all subranges thereof). Solution concentration ranges also include about 1 wt. % to about 20 wt % (and all subranges thereof), about 5 wt. % to about 45 wt. % (and all subranges thereof) and about 5 wt. % to about 20 wt. % (and all subranges thereof) of the hydrophillic or ionic organic or organometallic compounds that form the anisotropically oriented components. The quality (uniformity of patterns and anisotropic optical performances) of the patterned anisotropic solids formed by the processes herein are generally lower if the concentration of the ionic organic or organometallic component in the solution is too low (e.g. <0.1 wt %). Solutions useful in the invention may be non-isotropic and contain liquid crystalline phases.

In specific preferred embodiments, this method employs an aqueous solvent and a reusable template, operates under ambient conditions, and does not require photoalignment or mechanical rubbing or stretching of the substrate. Neither does it require polymerization or the application of pressure or heat. The method of the invention thus provides a convenient and inexpensive approach to the manufacturing of micropatterned anisotropic materials.

Complex two dimensional (2-D) micro-patterns or nano-patterns of different mesogens on a substrate can be generated by the methods of this invention.

In one exemplary approach (illustrated in FIG. 2A), that is designated the parallel approach, microfluidic techniques are used to introduce two or more solutions of different mesogens to desired separated regions of the micro-features or nano-features on a template. The solutions are then concentrated to generate anisotropically oriented liquid crystals that are subsequently dried to give micro- or nano-patterned anisotropic solids. By selecting mesogens that absorb light at different wavelengths, complex micro- or nano-patterns of colored solids that polarize light are produced.

In another exemplary approach (illustrated in FIG. 2B), micro- or nano-patterns are developed simultaneously on two surfaces of the substrate. A substrate (e.g., a glass coverslip) is sandwiched between two templates that have the same or different patterns of micro- or nano-features. This approach is designated the sandwich method. If both templates contain line features, the angle between the line patterns of the two templates may vary from 0° to 90°. The templates are then filled with the solutions of the desired mesogens (the same mesogen on both sides or different mesogens on the different surfaces of the substrate). Evaporation of solvent from the solutions allows the formation of liquid-crystalline materials that subsequently form anisotropic solids upon drying.

In another exemplary approach illustrated in FIG. 2C, a template with micro- or nano-features is used to guide the formation of liquid crystals of mesogen A to generate a micro- or nano-pattern of anisotropic solid A on one side of the substrate. After the first template is peeled off, the substrate with the micro- or nano-pattern of anisotropic solid is place onto a second template that may have the same or different micro- or nano-features as the first template. If both templates contain line features, the angle between the line patterns of the two templates may vary from 0° to 90°. The micro- or nano-features of the second template are then filled with a solution of mesogen A or a different mesogen B. Solvent is then allowed to evaporate slowly to generate the liquid crystals and subsequently the second micro- or nano-pattern of anisotropic solid. If mesogen A is insoluble in the solvent used for mesogen B, the micro- or nano-patterns of mesogens A and B can be prepared on the same side or different sides of the substrate surface.

Complex three dimensional (3-D) micro- or nano-patterns of one or more mesogens on a substrate can also be generated by the methods of this invention.

It is known in the art that templates or molds (e.g., those made of PDMS) with 3-D features (e.g. interwoven micro- or nano-channels) can be prepared. An exemplary method for making such templates has been described[33]. These 3-D features, such as channels, wells or like indentations are filled with the one or more solutions of soluble orienting molecule. For example, microfluidic techniques can be used to selectively introduce the solution or solutions. Evaporation of solvent yields liquid-crystalline domains and subsequent leads to the formation of 3-D micro- or nano-patterns of anisotropic materials.

Complex 2D and 3D micropatterns can be made by applying one or more of these approaches separately, or by applying a combination of these approaches.

Anisotropically oriented solids can be formed on substrates including transparent, semi-transparent, non-transparent materials and/or reflective materials. Substrates may include any combination of transparent, semi-transparent, non-transparent materials and/or reflective portions. Suitable substrates include, among others, glass, mica, plastic or metal or polymer substrates. The substrate is generally selected for compatibility with the anisotropic solid to be formed, the solvent or solvent system used and suitability for a given application. For example, transparent or semi-transparent substrates would be generally more suitable for use in transmissive optical applications and non-transparent or reflective substrates generally more suitable for use as semiconducting materials or as optical materials in the reflective mode or emissive mode. The solvent system and substrate are selected generally to avoid damage to the substrate by the solvent system.

The invention also provided anisotropically oriented solids containing one or more novel orienting compounds of this invention. These solids may be formed in a variety of shapes. In general, one dimension of the solid or a feature of the solid is micro-scale or nano-scale. Films and layers of anisotropic solid of varying thickness can be prepared by the methods herein by varying the concentration of the soluble orienting molecule in the solution used to make the anisotropic solid and the dimensions of the template employed. Films and layers that range in thickness from less than 100 nm up to 100 microns can generally be prepared. The preferred thickness of the film or layer will depend upon the application. Films and layers of anisotropic materials of this invention can be employed in optical and electronic applications, among others.

Anisotropic solids of this invention made by the method herein or made employing the novel compounds herein can exhibit dichroic ratios (as that term is understood in the art) of 10 or more or 20 or more.

Anisotropic solids, including films and layers of anisotropic solids, of this invention can be employed as polarizers and in particular as fluorescent polarizers.

The substrate may be pretreated to enhance interaction of the solid formed with the substrate. Pretreatment may include application of a coating, and or chemical etching or mechanical abrasion. In certain cases, e.g., glass substrates, it is preferred that the surface is clean and commercially-available precleaned glass slides or coverslips have been found to be suitable.

In a specific embodiment, the template (mold or die) used in the method herein is made of flexible materials to facilitate removal of the solid. The template used may provide for formation of surface features on an anisotropic solid or may provide for formation of a three-dimensionally shaped solid. For example, the template may be selected and contacted with the solution, such that on removal of solvent and formation of the solid less than all the surfaces of the solid conform to surfaces of the template. The anisotropic solid can be formed as a layer on a substrate or as a separate structure, such as a disk, plate or slab. In a specific embodiment, the template is made from materials that have only weak interactions with the solid to avoid any significant sticking, so that the anisotropic solid can be removed from the template intact. In a specific embodiment, the template is made of an elastomer material, particularly an elastomeric polymer, such as poly (dimethylsiloxane) (PDMS). An advantage of the use of an elastomeric polymer in the template is that it makes good contact with substrate upon which the anisotropic solid is to be formed.

In a specific embodiment the template comprises one or more internal micro or nano-scale structures, such as ridges, channels, wells and the like, such that complementary micro- or nano-scale structures are formed in, on or out of the anisotropic solid.

In a specific embodiment the template is made from an organic polymer, or mixture of organic polymers, or an organic-inorganic hybrid polymer. Suitable organic polymers for use in templates include among others, poly(dimethylsiloxane) (PDMS), Teflon™, various polyurethanes, various polystyrenes, and poly(methyl methacrylate) (PMMA). Preferable the template is made of an elastomeric polymer such as PDMS. Template materials may include organic or inorganic polymer additives which may enhance desirable template properties such as elasticity, flexibility, non-sticking, and durability for repeated use. Preferred materials for use in templates are those that result in high fidelity, e.g., sub-0.1 micron, molding.

In a specific embodiment the template is sacrificial, so that it can be destroyed by chemical treatment (heat, etc.), exposure to light or other treatments to release the anisotropic solid without damaging the solid. Destruction of the template can be followed by one or more washing steps to remove undesired residues. In a specific embodiment, the template is formed from a material that can be destroyed by exposure to light, particularly by light of a selected frequency, and any residue remaining can then be removed by solvent washing.

In specific embodiments, compounds useful in the method of this invention for generation of anisotropic solids are mesogens which are compounds which exist under suitable temperature, pressure or concentration in a suitable solvent or solvent system in a liquid crystal phase. In preferred embodiments, compounds useful in the method of this invention are amphiphilic mesogens in which the mesogen is composed of molecules having portions that are hydrophilic and other portions that are hydrophobic. A lyotropic liquid crystal phase is formed by dissolving an amphiphilic mesogen in a suitable solvent under selected temperatures pressures and at selected mesogen concentrations. Those of ordinary skill in the art can determine using well-known methods if a given molecule is a mesogen or amphiphilic mesogen and can determine using well-known methods if a given type of liquid crystal phase is present in a solid or liquid (solution).

Compounds useful in the methods herein include those of formula I:

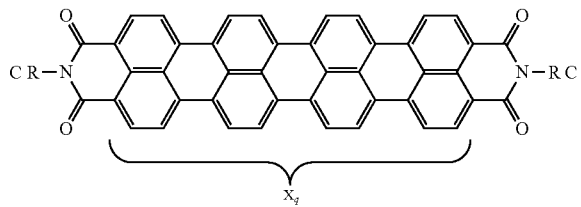

where:

R are hydrophillic groups including charged groups and C are one or more appropriate counterions for any charged groups present and $X_q$ represents "q" possible substituents on the aromatic ring system.

Hydrophilic groups generally include charged groups, including cationic groups (i.e., groups containing protonated amine groups or quaternary ammonium groups) or anionic groups (groups containing carboxylate groups, or sulfate groups, or sulfonate groups or phosphate groups or phosphonate groups) or nonionic groups, including ionizable groups (e.g., groups containing amines which can be protonated or from which quaternary ammonium ions can be formed, guanidinium groups or groups containing carboxylic acids which can formed carboxylates) as well as groups containing polar functional groups, such as alcohols, esters and ethers.

In specific embodiments, R that is uncharged is selected from alkyl, alkenyl, alkynyl or aryl groups substituted with one or more hydrophilic substituents or in which one or more C, CH, $CH_2$, $CH_3$ moieties are replaced with one or more O atoms, S atoms, P atoms, —CO— groups, —O—CO— groups, —$SO_3$— groups, N atoms, —$NR^1$— groups, or —$NR^1CO$— groups. Hydrophillic R include among others, amine groups, diamine groups, polyamine groups, alcohols, esters and acids. Hydrophilic substituents include among others one or more hydroxyls, thiols, alkoxyl groups, —COOH groups, or —$COOR^2$ groups. $R^1$ and $R^2$ are optionally substituted alkyl, alkenyl, alkynyl or aryl groups. R groups optionally have additional substituents including one or more halogens, nitro groups, cyano groups, isocyano groups, thiocyano groups, or isothiocyano groups. Specific uncharged R groups include: —$(CR_4R_5)_a$—OH, —$(CR_4R_5)_a$—O—$(CR_4R_5R_6)$, —$(CR_4R_5)_a$—[O—$(CR_4R_5)_b]_c$—$CR_4R_5R_6$, —$(CR_4R_5)_a$—SH, —$(CR_4R_5)_a$—S—$(CR_4R_5R_6)$, —$(CR_4R_5)_m$—$NR_1R_2$; —$(CR_4R_5)_m$—$NR_8$ $(R_7)_x$—$(CR_4R_8)_p$—$NR_1R_2$; —$(CR_4R_8)_m$—O—$(CR_4R_8)_p$—$NR_1R_2$, cyclic ethers, e.g., —$CR_9$—$(CR_4R_5)_a$—O—$R_{10}$, where $R_9$ and $R_{10}$ are linked to form a ring, -cyclic amines, e.g., —$(CR_4R_5)_m NR_1R_2$ where $R_1$ and $R_2$ are linked to form a ring, cyclic diamines, e.g, —$(CR_4R_5)_m NR_9R_{10}$—$NR_9R_{10}$ where groups $R_9$ and $R_{10}$ are linked to form a ring.

In specific embodiments, R that is positively charged is selected from protonated amines (which contain one or more than one nitrogen that can be protonated), quaternary ammonium ions (which contain one or more than one quaternary nitrogen) and guanidinium ions. Positively charged R can be selected, for example, from the group consisting of: —$(CR_4R_5)_m$—$N^+R_1R_2R_3$; —$(CR_4R_5)_m$—$NR_8$ $(R_7)_x$—$(CR_4R_8)_p$—$N^+R_1R_2R_3$; or —$(CR_4R_8)_m$—O—$(CR_4R_8)_p$—$N^+R_1R_2R_3$. —$(CR_4R_8)_m$—$N^+R_1R_2R_3$ where $R_1$ and $R_2$ are linked to form a ring, —$(CR_4R_5)_m$—$N(R_1)_x R_9 R_{10}$—$N(R_1)_y R_9 R_{10}$ where groups $R_9$ and $R_{10}$ are linked to form a ring, x and y=0 or 1 to indicate the presence of $R_1$ and either or both of x and y are 1 and one or both nitrogens in the groups are positively charged.

In specific embodiments, R that is negatively charged is selected from the group consisting of: $-(CR_4R_5)_m-SO_3^-$; $-(CR_4R_5)_m-COO^-$; or $-(CR_4R_5)_m-O-(CR_4R_5)_p-COO^-$; $-(CR_4R_5)_m-NR_6-(CR_4R_5)_p-COO^-$, $-(CR_4R_5)_m-NR_6-COO^-$, and $-(CR_4R_5)_m-PO_3^-$.

When R is positively charged C is one or more suitable anions and when R is negatively charged and C is one or more a suitable cations. In general, when R contains more than one charged group, C represents one or more counterions that neutralize the charge on R. When R contains more than one group that can be ionized, protonated or quaternized, one or more of these groups may be charged. For example, when R is $-(CR_4R_5)_m-NR_8(R_7)_x-(CR_4R_5)_p-N^+R_1R_2R_3$, the second and/or third nitrogens in the R group can also be positively charged and C (the number of anions or their charge) is selected to make the compound charge neutral;

$R_{1-3}$ are, independently of each other and any other $R_{1-3}$ in the compound, selected from the group consisting of H or optionally substituted alkyl or alkyl in which one or more C, CH or $CH_2$ moieties can be replaced with one or more O atoms, S atoms, P atoms, $-CO-$ groups, $-O-CO-$ groups, $-SO_3-$ groups, $-PO_3-$ groups, N atoms, $-NR^1-$ groups, or $-NR^1CO-$ groups;

$R_{4-6}$ are, independently of one another and independently of other $R_4$ and $R_5$ in the compound, selected from H, halogen, optionally substituted alkyl or alkyl in which one or more C, CH or $CH_2$ moieties can be replaced with one or more O atoms, S atoms, P atoms, $-CO-$ groups, $-O-CO-$ groups, $-SO_3-$ groups, $-PO_3-$ groups, N atoms, $-NR^1-$ groups, or $-NR^1CO-$ groups;

$R_7$ (if present) is selected from the group consisting of hydrogen or optionally substituted alkyl or alkyl in which one or more C, CH or $CH_2$ moieties can be replaced with one or more O atoms, S atoms, P atoms, $-CO-$ groups, $-O-CO-$ groups, $-SO_3-$ groups, $-PO_3-$ groups, N atoms, $-NR^1-$ groups, or $-NR^1CO-$ groups, where x is either 0 or 1 to indicate the presence or absence of $R_7$;

$R_8$ is selected from the group consisting of hydrogen, optionally substituted alkyl or alkyl in which one or more C, CH or $CH_2$ moieties can be replaced with one or more O atoms, S atoms, P atoms, $-CO-$ groups, $-O-CO-$ groups, $-SO_3-$ groups, $-PO_3-$ groups, N atoms, $-NR^1-$ groups, or $-NR^1CO-$ groups, or $-(CR_4R_5)_r-NR_1R_2(R_3)_y$, where $R_{1-5}$ are as defined above, r is an integer ranging from 1-6 and y is 0 or 1 to indicate the presence or absence of $R_3$;

$R_{9-10}$ are, independently of each other and any other $R_{9-10}$ in the compound, selected from the group consisting of optionally substituted alkyl groups or alkyl groups in which one or more C, CH or $CH_2$ moieties can be replaced with one or more O atoms, S atoms, P atoms, $-CO-$ groups, $-O-CO-$ groups, $-SO_3-$ groups, $-PO_3-$ groups, N atoms, $-NR^1-$ groups, or $-NR^1CO-$ groups;

a, b, c, m and p are integers ranging generally from about 1-20 and more preferably from 1-12, in specific embodiments, m+p ranges from 1 to 12, a+b ranges from 1-12 or a+c(b) ranges from 1-18;

each X, independent of other X in the compound, is a substituent on the aromatic ring system selected from:

a non-charged substituent on the aromatic ring system wherein each X independent of other X is selected from the group consisting of alkyl, alkoxy, alkyl sulfide, alkyl disulfide, cyano, isocyano, thiocyano, isothiocyano, nitro, or halogen, wherein one or more C, CH or $CH_2$ groups of the alkyl groups or alkoxy groups can be replaced with one or more of an O atom, S atoms, P atoms, a $-CO-$ group, a $-O-CO-$ group, a $-SO_3-$ group, a $-PO_3-$ group, an N atom, an $NR_1$ group, an $-NR_1-CO-$ group and wherein one or more C of the alkyl or alkoxy group can be substituted with one or more halogens, hydroxyl, thiol, cyano, isocyano, thiocyano, isothiocyano or nitro groups; or a charged substituent, where a charged X is accompanied by an appropriate counterion;

when R is negatively charged X can be negatively charged and when R is positively charged X can be positively charged;

negatively charged X include among others, $-COOH$ or $-COO^-$, $-SO_3H$ or $-SO_3^-$, $-PO_3H$ and $PO_3^{2-}$;

positively charged X can, among others, be guanidinium ions, $-NR_1(R_2)_z(CR_4R_5)_m-N^{\oplus}R_1R_2R_3$ or $-NR_1(R_2)_z(CR_4R_5)_m-NR_6(R_7)_y(CR_4R_5)_p-N^{\oplus}R_1R_2R_3$, where $R_{1-7}$ are as defined above, and y and z can be 0 or 1 to indicate the absence or presence of the group, when z is 1 and y is 1 additional N in the group can be positively charged;

charged X groups can also include alkyl groups carrying one or more charged or ionizable substituents, including any of $-COOH$ or $-COO^-$, $-SO_3H$ or $-SO_3^-$, guanidiunium ions, $-NR_1(R_2)_z(CR_4R_5)_m$ $N^{\oplus}R_1R_2R_3$ or $-NR_1(R_2)_z(CR_4R_5)_m$ $NR_6(R_7)_y(CR_4R_5)_pN^{\oplus}R_1R_2R_3$, where $R_{1-7}$ are as defined above, y and z can be 0 or 1 to indicate the absence or presence of the group, when z is 1 and y is 1 additional N in the group can be positively charged; and q is an integer ranging from 0 to 16 (when q is 0, all X are hydrogens and the ring system is not substituted).

Each R in the compound may be the same or different, but charged R's in the same compound preferably are either both positively charged or are both negatively charged.

Counterions C appropriate for a given application and compatible with a given ionic orienting molecule herein can be readily selected by one of ordinary skill in the art. In specific embodiments, anions and cations are selected to provide salts that are soluble in selected solvents or solvent systems. In specific embodiments, anions and cations are chosen to provide salts that are soluble in water or aqueous solution. Anionic C can be selected, for example, from halides ($F^-$, $Br^-$, $Cl^-$, $I^-$), nitrates, chlorates, perchlorates, acetate (or other anions derived from carboxylic acids), trifluoroacetate (or other anions derived from halogenated carboxylic acids), sulfate, alkyl or aryl sulfates, and alkyl or aryl sulfonates. Cationic C can be selected, for example, from alkalii metal cations ($Na^+$, $K^+$, $Cs^+$, $Li^+$, etc.), alkaline earth metal cations ($Mg^{+2}$, $Ca^{+2}$, etc.), ammonium cations, alkyl or aryl ammonium cations, alkoxy or aryloxy ammonium cations, pyridinum cations or other cations of nitrogen-containing aryl groups. In specific embodiments, counterions are non-toxic in the form in which they are employed and for applications with biological molecules, the selected counterions preferably do not exhibit detrimental effect on such biological molecules.

The terms alkyl, alkenyl, alkynyl are used herein in the broadest sense that they are used in the art and include straight-chain, branched or cyclic alkyl, alkenyl or alkynyl groups. Alkenyl groups may contain one or more double bonds. Alkynyl groups may contain one or more triple bonds.

In specific embodiments, X is not a charged group. In other specific embodiments, X is not a $-SO_3H$ or an $-SO_3^-$ group. In specific embodiments, X are all hydrogens.

Compounds of Formula II (perylenebis(dicarboxylmides) are also useful in the methods herein:

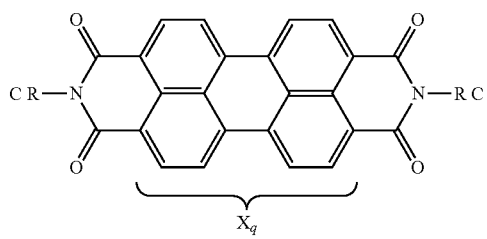

where:

R are hydrophilic groups which can be uncharged or charged groups and C are one or more appropriate counterions paired with charged R groups and $X_q$ represents "q" (in this case 0-8) possible substituents on the aromatic ring system. Variables R, C, if present, and X, if present are generally as defined above formula I.

Mesogens of Formula III (perylenemono(dicaroximides)) are also useful herein:

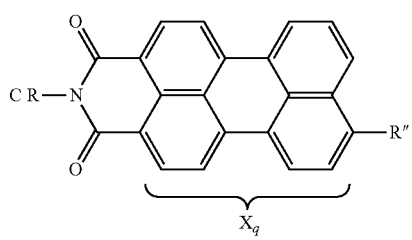

where:

R is a charged group and C is one or more appropriate counterions and $X_q$ represents "q" (0-9) possible substituents on the aromatic ring system; all of R, C, if present, and X, if present, are as defined above for formula I; and R" is hydrogen or a non-hydrogen substituent or a hydrophilic group and the hydrophilic group may be charged or uncharged. R" can be a non-charged group selected from the group consisting of alkyl, alkoxy, alkyl sulfide, alkyldisulfide, thiol, cyano, isocyano, thiocyano, isothiocyano, nitro, or halogen, wherein one or more C, CH or $CH_2$ groups of the alkyl groups or alkoxy groups can be replaced with one or more of an O atom, a S atom, a P atom, a —CO— group, an —O—CO— group, a —$SO_3$— group, a —$PO_3$— group, a N atom, an $NR_1$ group, an —$NR_1$—CO— group and wherein one or more C of the alkyl or alkoxy group can be substituted with one or more halogens, hydroxyl, cyano, isocyano, thiocyano, isothiocyano or nitro groups; R" can also be selected from any of the non-charged or charged groups R groups listed above in the definitions of variable in Formula I.

In specific embodiments, R" is a halogen. In other specific embodiments, R" is hydroxyl or thiol. In other specific embodiments, R" is an amine containing one or more nitrogens (including diamines, cyclic amines, and cyclic diamines). In other specific embodiments, R" is a group containing one or more protonated amines and/or one or more quaternary ammonium groups. In other specific embodiments, R" is an amine containing two or more N atoms. In other specific embodiments, R" is a cyclic amine or cyclic diamine, each of the N of which may be protonated or quaternized to form a quaternary ammonium group. In other specific embodiments, R" is an alkyl group substituted with one or more hydroxyl groups. In other specific embodiments, R" is an ether group or a polyether group. In other specific embodiments, R" is an ester group. In specific embodiments, R" is a substituent other than —$SO_3H$ or —$SO_3^-$.

Compounds useful herein also include those of formulae IV-1 and IV-2:

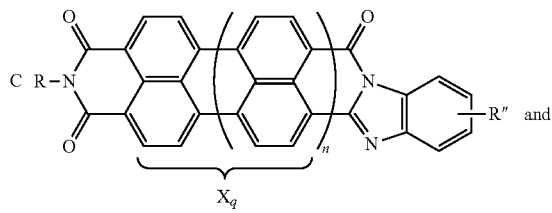

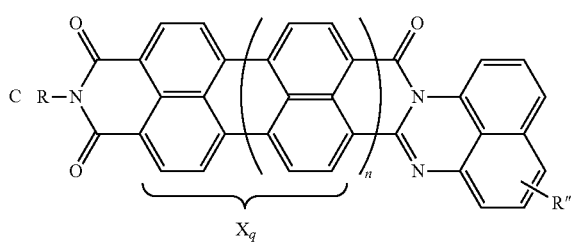

where:

n is 0 or 1;

R is a hydrophilic or charged group as defined in formulas I, II, and III above and if R is charged C is one or more appropriate counterions (as defined above) and $X_q$ represents "q" possible substituents (0 to (4n+4)) on the aromatic ring system;

X, and R" are as defined in formulas I, II and III above and q is an integer ranging from 0 to 8 (when q is 0, all X are hydrogens) with the exception that there can be one or more of R" substituents on the molecule;

Compounds of formulae VI-1 and VI-2 are useful in the methods herein:

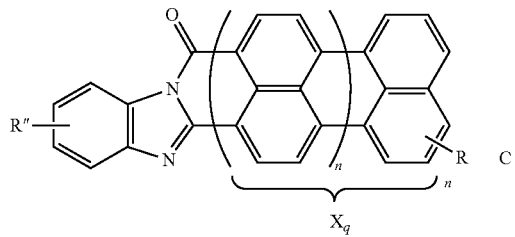

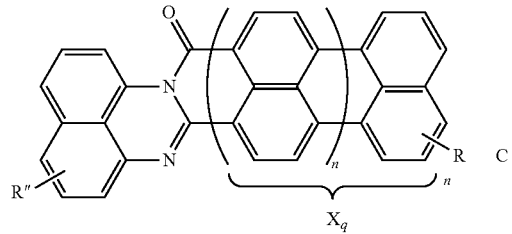

where:

n is 0 or 1;

R is a hydrophilic group or a charged group as defined above in Formulas I, II and III and C, if present, is one or more appropriate counterions as defined above and $X_q$ represents "q" possible substituents on the aromatic ring system; and X and R" are as defined in formulas I and III above, and q is an integer ranging from 0 to 9 (when q is 0, all X are hydrogens).

Exemplary compounds useful herein include those of the above formulae in which:

A. When R is $-(CR_4R_5)_m-N^+R_1R_2R_3$; $-(CR_4R_5)_m-NR_6(R_7)_x-(CR_4R_5)_p-N^+R_1R_2R_3$; or $-(CR_4R_5)_m-O-(CR_4R_5)_p-N^+R_1R_2R_3$:

all $R_{4-5}$ are all hydrogens and at least one of $R_{1-3}$ is a hydrogen; or at least one of the $R_{4-5}$ in the compound is an alkyl group, the remaining $R_{4-5}$ being hydrogens and at least one of $R_{1-3}$ is a hydrogen; or any $R_{1-5}$ in the compound that are alkyl groups are alkyl groups having from 1-4 carbon atoms; or any $R_{1-5}$ in the compound that are alkyl groups are alkyl groups having 1 or 2 carbon atoms; or any $R_{4-5}$ in the compound that are alkyl groups are methyl groups; or any $R_{1-3}$ in the compound that are alkyl groups are ethyl groups; or all $R_{4-5}$ are hydrogens and two of $R_{1-3}$ are alkyl groups; or all $R_{4-5}$ are hydrogens and two of $R_{1-3}$ are ethyl groups; or m or p is 1-4;

if present, $R_6$ is an alkyl group having from 1 to 4 carbon atoms; or if present, $R_6$ is a hydrogen; or if present, $R_6$ and $R_7$ are both hydrogen;

if present, $R_6$ is an alkyl group having 1-4 carbon atoms and, if present, $R_7$ is a hydrogen; or if present, $R_6$ and $R_7$ are both alkyl groups having from 1-4 carbon atoms;

q is 0; or at least one X is an alkyl or alkoxy group; or q is 1-4; or q is 1-4 and X is alkyl or alkoxy having from 1-3 carbon atoms q is 1-4 and X is a methyl group; or q is 1-4 and X is a methoxy group;

q is 1-4 and X is a halogen; or q is 1-4 and X is a fluorine, or

R" is hydrogen; or

R" is Br, Cl or F; or

R" is $-NR_1(R_2)_z(CR_4R_5)_m$ $N \circledR R_1R_2R_3$ or combinations of the listed variables.

B. When R is $-(CR_4R_5)_m-N(R_7)_x[(CR_4R_5)_r-N^+R_1R_2R_3] (CR_4R_5)_p N^+R_1R_2R_3$ all $R_{4-5}$ are hydrogens and at least one of $R_{1-3}$ is a hydrogen; or at least one of the $R_{4-5}$ in the compound is an alkyl group, the remaining $R_{4-5}$ being hydrogens and at least one of $R_{1-3}$ is a hydrogen; or any $R_{1-5}$ in the compound that are alkyl groups are alkyl groups having from 1-4 carbon atoms; or any $R_{1-5}$ in the compound that are alkyl groups are alkyl groups having 1 or 2 carbon atoms; or any $R_{4-5}$ in the compound that are alkyl groups are methyl groups; or any $R_{1-3}$ in the compound that are alkyl groups are ethyl groups; or all $R_{4-5}$ are hydrogens and two of $R_{1-3}$ are alkyl groups; or all $R_{4-5}$ are hydrogens and two of $R_{1-3}$ are ethyl groups; or if present, $R_7$ is a hydrogen; or if present, $R_7$ is an alkyl group having from 1-4 carbon atoms; or if present, $R_7$ is a methyl group; or m, p and r are 1-4;

q is 0; or at least one X is an alkyl or alkoxy group; or q is 1-4; or q is 1-4 and X is alkyl or alkoxy having from 1-3 carbon atoms;

q is 1-4 and X is a methyl group; or q is 1-4 and X is a methoxy group;

q is 1-4 and X is a halogen; or q is 1-4 and X is a bromine; or

R" is hydrogen; or

R" is a halogen; or

R" is $-NR_1(R_2)_z(CR_4R_5), N^{\oplus}R_1R_2R_3$, or combinations of the variables listed.

C. When R is $-(CR_4R_5)_mCOO^-$; or $-(CR_4R_5)_mO-(CR_4R_5)_pCOO^-$:

all $R_{4-5}$ are all hydrogens; or at least one of the $R_{4-5}$ in the compound is an alkyl group, the remaining $R_{4-5}$ being hydrogens; or any $R_{4-5}$ in the compound that are alkyl groups are alkyl groups having from 1-4 carbon atoms; or any $R_{4-5}$ in the compound that are alkyl groups are alkyl groups having 1 or 2 carbon atoms; or any $R_{4-5}$ in the compound that are alkyl groups are methyl groups; or any $R_{4-5}$ in the compound that are alkyl groups are ethyl groups; or m and p are 1-4; or q is 0; or at least one X is an alkyl or alkoxy group; or q is 1-4; or q is 1-4 and X is alkyl or alkoxy having from 1-3 carbon atoms;

q is 1-4 and X is a methyl group; or q is 1-4 and X is a methoxy group;

q is 1-4 and X is a halogen; or q is 1-4 and X is a fluorine; or q is 1-4 and X is bromine; or R" is a halogen; or R" is H; or R" is $-COOH$ or $-COO^-$ or combinations of the listed variables.

Exemplary compounds useful herein include those of the above formulas in which R is an amine, diamine, cyclic amine or cyclic diamine including ionic forms and salts thereof in which one or more nitrogens can be protonated or formed into a quaternary ammonium ion. Exemplary compounds useful herein R groups include those which are alkyl groups substituted with one or more hydrophilic groups. Exemplary compounds useful herein include those of the above formulas in which R" is an amine, diamine, cyclic amine or cyclic diamine including ionic forms and salts thereof in which one or more nitrogens can be protonated or formed into a quaternary ammonium ion. Exemplary compounds useful herein R" groups include those which are alkyl groups substituted with one or more hydrophilic groups.

Additional exemplary compounds useful herein are provided in the examples.

In preferred embodiments, suitable anionic counterions (negatively charged C) include, among others, halides (e.g., $Cl^-$, $Br^-$, $I^-$); carboxylates (e.g., $R_8COO^-$, where $R_8$ is H, an alkyl or a halogenated alkyl group, including among others, HCOO⁻, CH₃COO⁻, or CF₃COO⁻); alkyl or aryl sulfonates (e.g., phenyl sulfonates, e.g., 4-CH₃-phenyl-SO₃⁻, or 4-CF₃-phenyl-SO₃⁻).

In preferred embodiments, suitable cationic counterions (positively charged C) include, among others, alkali metals (e.g., Na⁺, K⁺, etc.); and ammonium ions (e.g., NH₄⁺, N(R₉)₄⁺, where each R₉ can independently be hydrogen or an alkyl group, preferably alkyl groups having 1-4 carbon atoms).

Choice of counterion can affect solubility of the salt in a selected solvent or solvent system. For examples, sulfate salts are generally insoluble.

Exemplary compounds of formula I include:
Ia where q is 0 and R is CH₂CH₂N⁺H(Et)₂- (where Et is ethyl) and with suitable counterion (e.g., Cl⁻ or HCOO⁻);
Ib where q is 0 and R is CH₂CH₂N⁺ R"(Et)₂-, where R" is ethyl or methyl with suitable counterion (e.g., Br, HCOO⁻ or 4-CH₃-phenyl-SO₃⁻).

Exemplary compounds of formula II include:
Compounds of formula II where R is negatively charged, q is 0 and R is –CHR"COO⊖ where R" is H or alkyl and with suitable counterion (e.g., K⊕): for Compound IIa R" is H, for Compound IIb R" is methyl; for Compound IIc, R" is —CH(CH₃)₂, and for Compound IId, R" is —CH₂CH(CH₃)₂.

Compounds of formula II where R is positively charged (designated Formula VII) where q is 0:
VIIa: R is —CH₂CH₂N⊕H(Et)₂, C is Cl⊖ or HCOO⊖
VIIc R is —CH₂CH₂N⊕H₃, C is Cl⊖ or HCOO⊖
VIId R is —CH₂CH₂CH₂N⊕H(Me)₂, C is Cl⊖ or HCOO⊖
VIIe R is —CH₂CH₂CH₂N⊕H(Bu)₂, C is Cl⊖ or HCOO⊖, where Bu is n-butyl
VIIf R is —CH(C(Me)₂)CH₂CH₂N⊕H(Me)₂, C is Cl⊖ or HCOO⊖
VIIg R is —CH₂CH₂NH₂(CH₂CH₂N⊕H₃)₂, C is Cl⊖ or HCOO⊖
VIIh R is —CH₂CH₂CH₂N⊕HMeCH₂CH₂N⊕H₃, C is Cl⊖ or HCOO⊖
VIIi R is —CH₂CH₂N⊕Me(Et)₂, C is 4-CH₃-phenyl-SO₃⊖
VIIj R is —CH₂CH₂N⊕Me(Et)₂, C is I⊖
VIIk R is —(CH₂)₃N⊕(Me)₂(CH₂)₃N⊕H₂Me, C is 4-CH₃-phenyl SO₃⊖

Specific examples of compounds of formula III include:
IIIa: R=—(CH₂)₂N⊕HEt₂, q=0; C=Cl⊖, or HCOO⊖ or CH₃C₆H₄SO₃⊖
IIIb: R=—(CH₂)₂N⊕HEt₂, q=1, X=Br, C=Cl⊖, or HCOO⊖
IIIc: R=(CH₂)₂N⊕HEt₂, q=1 X=—NR"(CH₂)ₘN⊕R'''Et₂, R'''=H, or Me, or Et, C=Br⊖, or Cl⊖ or HCOO⊖, or CH₃C₆H₄SO₃⊖
IIId: R=—(CH₂)₂N⊕MeEt₂, q=0; C=CH₃C₆H₄SO₃⊖
IIIe: R=—(CH₂)₂N⊕MeEt₂, q=1, X=Br, C=CH₃C₆H₄SO₃⊖

Compounds IIIf-IIIk as described in the Examples.

Specific examples of compounds of formula IV-1 and IV-2 include:
IVa: n=0, q=0, R=—(CH₂)₂N⊕HEt₂, R"=H, C=HCOO⊖:
IVb: n=0, q=0, R=—(CH₂)₂N⊕HEt₂, R"=H, C=CH₃COO⊖:
IVc: n=0, q=0, R=—(CH₂)₂N⊕HEt₂, R"=OMe, C=CH₃COO⊖:
IVd: n=0, q=0, R=—(CH₂)₄N⊕H₃, R"=H, C=CH₃COO⊖:
IVe: n=1, q=0, R=—(CH₂)₂N⊕HEt₂, R"=H, C=HCOO⊖; (IVa-e based on the structure IV-1) and
IVf, based on the structure of formula IV-2, n=0, q=0, R=—(CH₂)₂NHEt₂, R"=H,C=CH₃COO—

Specific examples of compounds of formula IV-1 in which R are anionic designated herein compounds of formula V:
Va: n=1, q=0, R"=COO⊕, R₄=H, R₅=H, C=K⊖

Vb: n=1, q=0, R"=COO⊖; R₄=H, R₅=H, C=⊕NH₄
Vc: n=1, q=0, R"=COO⊖, R₄=H, R₅=—CH(CH₃)₂, C=K⊕
Vd: n=1, q=0, R"=COO⊖, R₄=H, R₅=—CH(CH₃)₂, C=⊕NH₄

Exemplary compounds of formula VI useful in this invention include:
VIa: n=0, q=0, R=—NH₂(CH₂)₄⊕NH₃, R"=H, C=CH₃COO⊖ and additional compounds described in the Examples.

In several of the specifically exemplified compounds useful in this invention listed above, the positively charged R groups may contain more than one N which can be charged, in the formulas listed for such R groups it will be understood that each N in the R group may be positively charge or may become positively charged on protonation.

The methods herein can also employ cyanine dyes as soluble orienting molecules. An exemplary cyanine dye is:

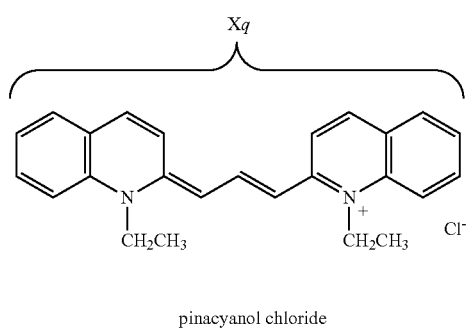

pinacyanol chloride where Xq represents one or more substituents on the available ring sites in the molecule, where X is defined above. Specific X include halogens, nitro groups, hydroxyl groups, sulfate groups, cyanide, isocyanide, thiocyanide, isothiocyanide, alkyl, and halogenated alkyl.

The methods herein can also employ azodyes. An exemplary azo dye is:

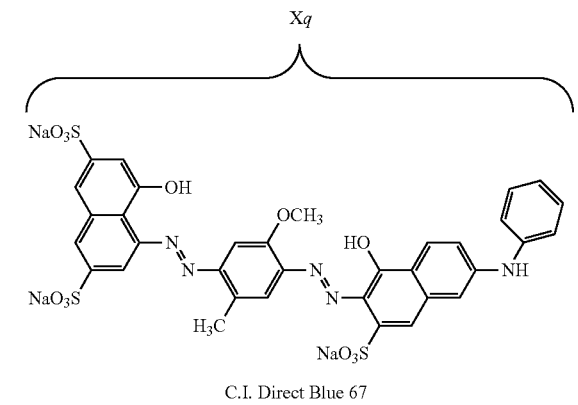

C.I. Direct Blue 67 where Xq represents one or more substituents on the available ring sites in the molecule, where X is defined above. Specific X include halogens, nitro groups, hydroxyl groups, sulfate groups, cyanide, isocyanide, thiocyanide, isothiocyanide, alkyl, and halogenated alkyl.

The methods of this invention can employ organometallic lyotropic liquid crystals as orienting compounds. These metallomesogens form liquid crystals (nematic and M-chromonic type) in apolar solvents (in the presence or absence of other organic molecules, e.g. trinitrofluorenone). Exemplary metallomesogens include those of formulas:

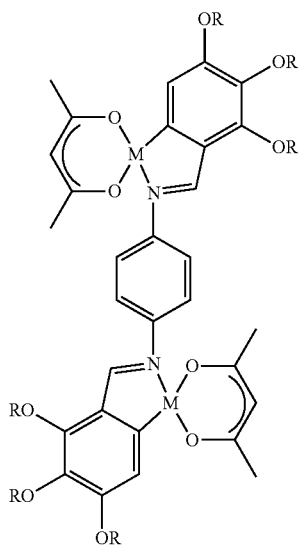

e.g., M = Pd or Pt,
R = alkyl
solvent: apolar solvents

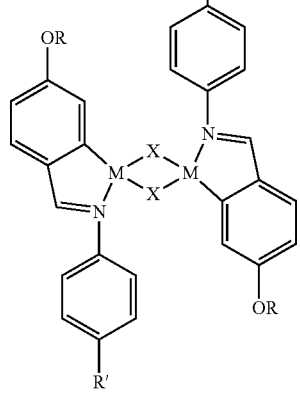

e.g., M = Pd or Pt, X = Br, Cl, I
R = alkyl, R' = H or OR
solvent: apolar solvents and derivatives thereof including those derivatives having one or more X substituents as defined above on available ring sites, where X is as defined above. Specific X include halogens, nitro groups, hydroxyl groups, sulfate groups, cyanide, isocyanide, thiocyanide, isothiocyanide, alkyl, and halogenated alkyl.

Additional examples of organic and organometallic mesogens that are useful in the methods herein are provided in Dirk Blunk, Klaus Praefcke, and Volmar Vill "Amphotropic Liquid Crystals" in "Handbook of Liquid Crystals, vol. 3" Demus D., Goodby, J., Gray, G. W., Spiess, H.-W., Vill, V. Eds. Wiley-VCH: New York. 1998, p332-334, which is incorporated by reference herein for its description of these mesogens.

The solutions containing soluble organic and/or organometallic orienting compounds that function for orientation of the molecules to form the anisotropic solid (i.e., hydrophobic or ionic orienting molecules or compounds) can also contain additional organic (non-mesogenic or that do not form chromogenic LC phases) or inorganic components present in amounts that do not detrimentally interfere with the formation of the desired LC phase (e.g., chromogenic phase).

The solutions employed in the method of this invention may contain a single kind of hydrophobic or ionic orienting compound or a mixture of such compounds of different chemical structures.

Various organic, organometallic and inorganic additives can be introduced into the ionic orienting molecule-containing solutions to affect the chemical, physical, optical or electronic properties of the anisotropic solid. For example, certain inorganic particles (preferably, nano-sized particles) can be added to affect, e.g., enhance, desirable mechanical or electrical properties. Examples of nano-sized particles that can beneficially affect the properties of anisotropic solids of this invention include, among others, gold, silver, titanium oxides, polystyrene and derivative polystyrene. Nano-sized particles are preferred to avoid disruption of the LC packing. In addition, plasticizers and surfactants and other additives which affect rheological properties can be employed which do not detrimentally affect molecular orientation of the soluble orienting molecules. Preferably all such additives are soluble in the solvent or solvent system employed. For example, water-soluble additives are preferred for use in aqueous solvents.

The orienting compound-containing solution used in the method herein can contain non-mesogenic organic, and/or organometallic components which beneficially affect the properties of the anisotropic solid. For example, additives, such as surfactants and/or inorganic salts may enhance the formation of a desired LC phase. Dopants added to the solution herein can increase the conductivity of the anisotropic solids that result from the methods herein. Additionally, additives which affect the optical properties of the anisotropic solid, but do not affect the formation of that solid can be employed.

Any additive to the soluble orienting compound-containing solution should be present in an amount that does not detrimentally interfere with the formation of the desired LC phase and preferably should be present in an amount sufficient to convey a desired beneficial property to the solid.

The invention also provides novel orienting compounds of the formulas I-VI herein and various salts and ionic forms thereof. These compounds include perylene and quaterylene compounds carrying one or more hydrophilic substituents and ionic perylene and ionic quaterrylene compounds. Compounds of formulas I-VI herein can be made by methods herein or in view of methods herein and methods that are generally well-known in the art.

This invention also provides novel compounds that exhibit liquid crystalline phase, particularly lyotrophic liquid crystalline phases. As such certain mesogenic compounds of this invention can be employed in various liquid crystal applications as well as additives to liquid crystals. Certain compounds of this invention, including, but not limited to Ia, exhibit the development of chromonic liquid-crystalline domains in solution (e.g., aqueous solution or water) into ribbon-like structures over 200 microns in length which can vary in width from less than 5 micron up to about 20 micron.

This invention also provides novel compounds, in particular, compounds 4, 5 and IIIa-k which exhibit desirable absorption and fluorescence properties in solution and in the solid phase. Compounds of formulas herein exhibit fluorescence properties in solution (aqueous or organic) and in solid phase. Some of these compounds (including but not limited to compounds IIIc, IIIf-IIIk) exhibit uv-vis absorption properties that are pH dependent and fluorescence properties that are dependent on the solvent, pH, and the absence or presence of biologically relevant molecules such as nucleic acids (DNA, RNA, and oligonucleotides.) These compounds are generally useful as dichroic dyes and fluorescent dyes in solutions as well as useful in the preparation of anisotropic materials.

In particular, compounds 4, 5, and compounds with general structures III can exhibit beneficial properties as absorption dyes which include: intensive absorption in the visible light region; dichroic (direction-dependent) absorption; solubility in a wide range of solvents including aqueous solvents of various pH, organic solvents (including dimethylsulfoxide, organic acids such as acetic acid, formic acid, and trifluoroacetic acid, halogenated organic solvents such as $CH_2Cl_2$, alcohols, such as methanol), and mixtures of aqueous and organic solvents. Compounds with structures with at least one N atom on the aromatic rings (including IIIc, IIIf-IIIk) exhibit pH dependent absorption properties, and can be used as pH probes. In particular, compounds 4, 5, and compounds with general structures III can exhibit beneficial properties as fluorescent compounds including: direction dependent fluorescence; fluorescence in both solid phase and solution phase, including aqueous solvents of various pH, organic solvents (including dimethylsulfoxide, organic acids such as acetic acid, formic acid, and trifluoroacetic acid, halogenated organic solvents such as $CH_2Cl_2$, alcohols such as methanol), and mixtures of aqueous and organic solvents; and compounds with structures with at least one N atom on the aromatic rings (including IIIc, IIIf-IIIk) exhibit pH dependent fluorescence properties, and can be used as pH probes. Fluorescence properties of compounds of this invention (in particular compounds IIIc, IIIf-IIIk) are sensitive to their microenvironment (hydrophobic or hydrophilic environment), which is potentially useful in probing local environments in biological systems such as proteins or lipid membranes or nucleic acids. Compounds of this invention exhibit excitation and emissions at long wavelengths (e.g., red and near-infrared) in the visible region, which minimizes inferences from autofluorescence of biological molecules making these molecules particularly useful as biological labels and in biological assay applications. Compounds of this invention can exhibit large Stoke shifts (difference in the $\lambda_{max}$ values of excitation and emission), such that excitation light can be filtered readily from emission, therefore simplifying optics designs.

When a group of substituents is disclosed herein, it is understood that all individual members of that group and all subgroups, including any isomers and enantiomers of the group members, are disclosed separately. When a Markush group or other grouping is used herein, all individual members of the group and all combinations and subcombinations possible of the group are intended to be individually included in the disclosure. When a compound is described herein such that a particular isomer or enantiomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Specific names of compounds are intended to be exemplary, as it is known that one of ordinary skill in the art can name the same compounds differently.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure.

Optical, electronic and liquid crystalline properties of the molecules, solutions and solids of this invention can be assessed employing methods that are well-known in the art.

All patents and publications mentioned in the specification are indicative of the levels of skill of those skilled in the art to which the invention pertains. References cited herein are incorporated by reference herein in their entirety to indicate the state of the art as of their filing date and it is intended that this information can be employed herein, if needed, to exclude specific embodiments that are in the prior art. For example, when a compound is claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, reagents, solid substrates, synthetic methods, purification methods, and analytical methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Each references cited herein is incorporated by reference herein to the extent that it is not inconsistent with the disclosure of this application. If there is an inconsistency in definitions of terms or in discussion of mechanisms of activity between the present specification and definitions in any of the journal articles or patents incorporated by reference herein, the definitions of this specification take precedence.

References cited herein include those that provide an overview of art-known methods and techniques, synthetic methods useful for making molecules of this invention, additional descriptions of chemical structures of compounds useful in this invention, and additional descriptions of applications of the anisotropic solids made by the methods herein.

THE EXAMPLES

Example 1

This example describes an improved method for the synthesis of quaterrylene bis(dicarboximide)s, in particularly ionic quaterrylene bis(dicarboximide)s Ia and Ib, as outlined in Scheme 1. (See also: -W. Tam-Chang, W. Seo and I. K. Iverson (2004) J. Org. Chem. 69:2719-2726 which is incorporated herein in its entirety.)

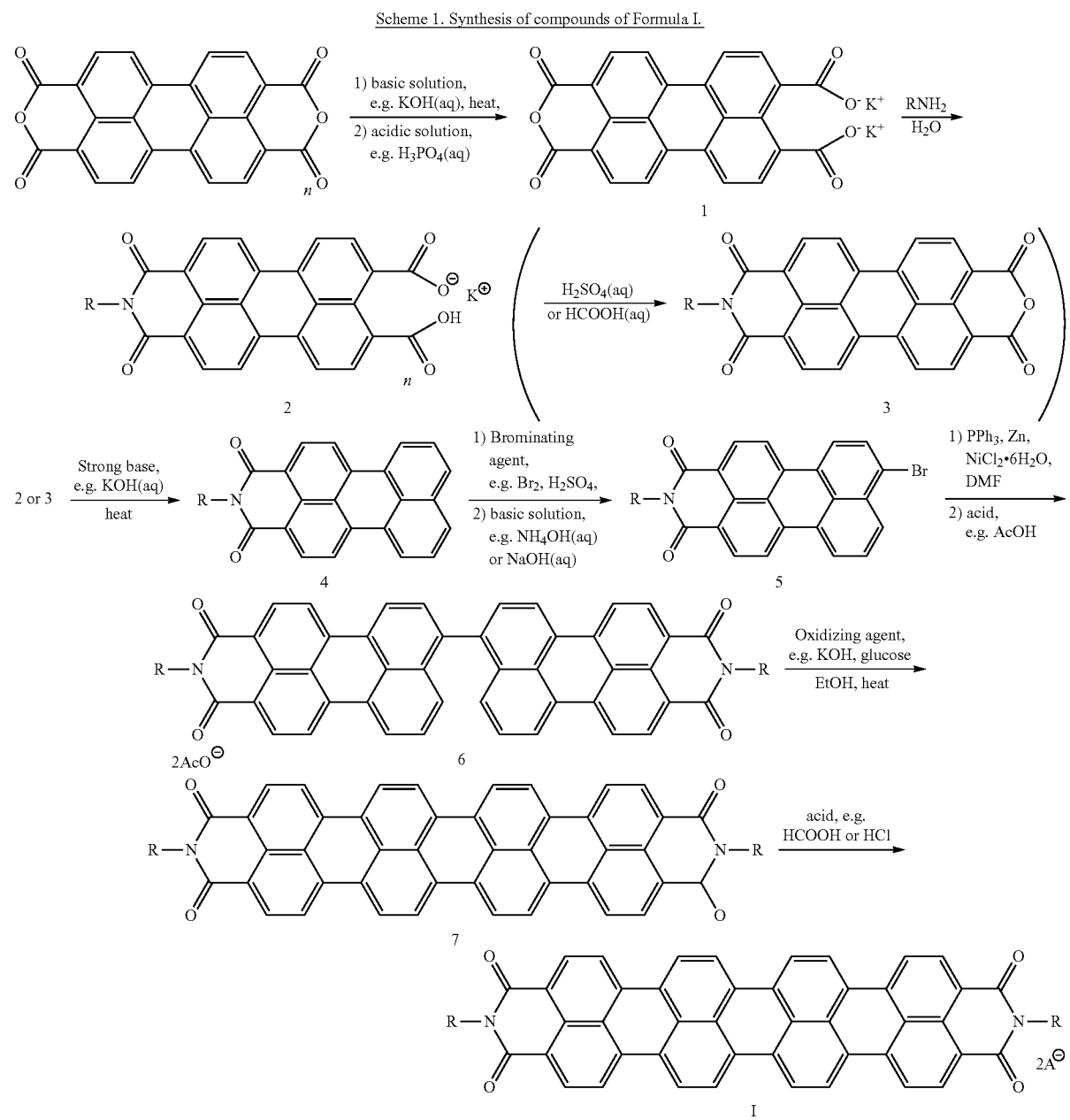

Ia is the compound of formula I, where q is 0 and R is —CH$_2$CH$_2$N$^+$H(Et)$_2$ (where Et is ethyl) and with suitable counterion (e.g., Cl$^-$ or HCOO$^-$); Ib is the compound of formula I, where q is 0 and R is —CH$_2$CH$_2$N$^+$R"(Et)$_2$, where R" is ethyl or methyl with suitable counterion (e.g., Br$^-$, HCOO$^-$ or 4-CH$_3$-phenyl-SO$_3^-$).

The procedure previously reported for the synthesis of non-ionic quaterrylene-bis(dicarboximide) (Quante, H. I; Mullen, K. (1995) Angew, Chem. Int. Ed. Engl. 34:1323 and Geerts Y. et al. (1998) J. Mater. Chem. 8:2357-2369) cannot be used for the synthesis of ionic quaterrylenebis(dicarboximide)s (e.g. Ia and Ib) because it causes the oxidative cleavage of the R groups. Furthermore, the direct conversion of compound 2 to 4 simplifies the procedure and significantly reduced the time required for synthesis.

Monopotassium salt of N,N-Diethylammoniumethylperylene-3,4-dicarboxylicimide-9,10-dicarboxylic acid (2)

Compound 1 (9.82 g, 21.9 mmol) was suspended in doubly-distilled water at 0° C. to RT. A total of 10.63 g of N,N-diethylethylene diamine (exemplary RNH$_2$ of Scheme 1) was dissolved in water and added drop-wise to the suspension of 1. This was stirred for several hours. Acetone was added into the resulting solution to induce precipitation. The mixture was allowed to stand overnight, and the resulting brick red precipitate was collected using suction filtration. The residue was resuspended in acetone and the mixture was refluxed for an hour. The brick red solid was then isolated by suction filtration, washed with acetone, and under vacuum with heating overnight to yield 10.90 g (19.94 mmol, 91%) of 2 as a brick red solid.

N,N-Diethylammoniumethylperylene-3,4-dicarboxylicimide-9,10-dicarboxylic anhydride monosulfate or monoformate (3)

If desired, compound 3 can be prepared from the solution of 2 as follows: After acidification with 0.5 M sulfuric acid, the orange precipitate that formed was filtered, washed with 0.1M sulfuric acid, and dried under vacuum to give 3 in over 90% yield. For characterization purposes, the formate salt of 2 was also prepared by dissolving 1.10 grams of the isolated material in 125 mL of 88% formic acid, and then 75 mL of ethanol were added followed by 125 mL of dibutyl ether that was layered on slowly. The mixture was allowed to sit overnight to allow for complete precipitation. The bright red solid was filtered and washed with excess acetone and dried to give 0.75 g (75% recovery) of 3. All characterization was performed with the formate salt unless otherwise noted. 1H NMR (300 MHz, [D]TFA): δ=8.71 (d, 2H, $^3$J (H,H)=8 Hz; Ar—H), 8.51 (unresolved multiplet, 4H; Ar—H), 8.33 (d, 2H, $^3$J (H,H)=8 Hz; Ar—H), 8.08 (s, 1H; formate proton), 4.81 (unresolved t, 2H; α-CH$_2$), 3.87 (unresolved t, 2H; β-CH$_2$), 3.64 (multiplet, 4H; —N—(CH$_2$)—), 1.53 (t, $^3$J (H,H)=7 Hz, 6H; CH$_3$) ppm; $^{13}$C NMR (125 MHz, dTFA): δ=167.5, 163.4, 138.4, 137.1, 136.5, 135.4, 133.0, 131.1, 127.9, 127.8, 126.9, 126.7, 124.2, 119.5, 55.2, 50.5, 38.3, 9.3 ppm; IR (KBr): ν=1767, 1724, 1697, 1654, 1595, 1365, 1247, 808, 738 cm$^{-1}$; MS (FAB, m/z) Calcd for C$_{30}$H$_{23}$N$_2$O$_5$ (M$^+$.), 491. found: 491.

N,N-Diethylaminoethylperylene-3,4-dicarboxylmide (4)

Compound 4 can be prepared from 2 or 3. The direct reaction of 2 to give 4 was more efficient, since additional acidification and filtering steps were eliminated. Compound 2 (5.43 g, 9.93 mmol) and KOH (5.67 g, 86.75 mmol) were placed in a Teflon™ cup. Doubly distilled water (80 g) was added. After sonication for 30 minutes, the Teflon™ cup was then placed inside a 325-mL steel reactor vessel with a steel lid. The closed reactor vessel was completely submerged in a sand bath in a detonation safe room. The temperature was ramped to about 220° C. and maintained for about 12 h. The lid was removed after the vessel was cooled to RT. Its contents were washed out with excess water and filtered, washed with water again, and the solid obtained was dried under vacuum. This dried crude solid was then added to 200 mL of boiling chloroform and added to a basic alumina pad (4 cm in h.×14 cm in dia.). The basic alumina was eluted with an acetone/chloroform mixture (1:9 v/v). The eluent was collected until the filtrate became colorless. The volume of the filtrate was reduced and the product crystallized out slowly. Red needle-like crystals were filtered and dried under vacuum to give 4 in about 70% yield. $^1$H NMR (500 MHz, CDCl$_3$): δ=8.10 (d, $^3$J (H,H)=7.5 Hz, 2H; Ar—H), 7.93 (d, $^3$J (H,H)=7 Hz, 2H; Ar—H), 7.81 (d, $^3$J (H,H)=7.5 Hz, 2H; Ar—H), 7.67 (d, $^3$J (H,H)=8.5 Hz, 2H; Ar—H), 7.38 (t, $^3$J (H,H)=8.5 Hz, 2H; Ar—H), 4.23 (t, $^3$J (H,H)=8 Hz, 2H; α-CH$_2$), 2.80 (t, $^3$J (H,H)=8 Hz, 2H; β-CH$_2$), 2.71 (q, $^3$J (H,H)=7 Hz, 4H; —N—(CH$_2$)—), 1.15 (t, $^3$J (H,H)=7 Hz, 6H; CH$_3$) ppm; $^{13}$C NMR (125 MHz, [D]TFA): S=168.6, 142.9, 136.2, 135.6, 135.2, 132.0, 129.7, 129.3, 129.0, 128.3, 128.1, 122.5, 119.1, 54.6, 51.5, 38.7, 9.8 ppm; UV-vis (2.1×10$^{-4}$ M of the acetate salt in H$_2$O) λ$_{max}$ (ε, M$^{-1}$ cm$^{-1}$)=491 nm (18,000); UV-vis (2.5×10$^{-4}$ M in CHCl$_3$) λ$_{max}$ (ε, M$^{-1}$ cm$^{-1}$)=489 nm (36,000), 508 nm (34,000); IR (KBr): ν=2965 (m), 2806 (w), 1688 (s), 1649 (s), 1592 (s), 1571 (m), 1500 (w), 1423 (w), 1365 (s), 1295 (m), 1244 (m), 1211 (w), 1162 (w), 1088 (w), 855 (w), 837 (w), 810 (s), 752 (s) cm$^{-1}$; HRMS (DEI, m/z) Calcd for C$_{26}$H$_{24}$N$_2$O$_2$(M$^+$), 420.1838. found: 420.1822.

N,N-Diethylaminoethyl-9-bromoperylene-3,4-dicarboxylmide (5)

The bromination of 4 was achieved using bromine in sulfuric acid. The use of other brominating agents (such as bromine with iron or iron(III) bromide as catalyst caused the oxidative cleavage of the compound). In a 250-mL round-bottomed flask, 1.20 g (2.85 mmol) of compound 4 and 65 mL of concentrated sulfuric acid were mixed together. The mixture was cooled to −5° C., and then 0.19 mL of bromine were added drop-wise with a syringe. The reaction mixture was stirred vigorously at −5° C. for 1 hour. While still cold, the reaction mixture was poured into 250 mL of pre-chilled water in a 1000-mL recovery flask in an ice bath, and the pH of the resultant solution was adjusted to pH 8-9 by slowly adding about 170 mL of 30% NH$_4$OH (aq). A bright red precipitate formed, and the suspension was sonicated for 3 h to ensure complete deprotonation of the amine. The solid was filtered and washed with 300 mL of 5% NH$_4$OH (aq). The product was dried under vacuum to yield 1.41 g (2.81 mmol, 98%) of bright red solid 5. Compound 5 can be further purified by recrystallization in a 1% triethylamine/dimethylformamide (DMF) solution. The solid filtrate was washed with ether and dried under vacuum to recover 80% of 5. $^1$H NMR (500 MHz, CDCl$_3$): δ=8.34 (d, $^3$J (H,H)=8 Hz, 1H; Ar—H), 8.31 (d, $^3$J (H,H)=8 Hz, 1H; Ar—H), 8.14 (d, $^3$J (H,H)=7.8 Hz, 1H; Ar—H), 8.12 (d, $^3$J (H,H)=8.5 Hz, 1H; Ar—H), 8.06 (d, $^3$J (H,H)=7.5 Hz, 1H; Ar—H), 7.99 (d, $^3$J (H,H)=8 Hz, 1H; Ar—H), 7.85 (d, $^3$J (H,H)=8 Hz, 1H; Ar—H), 7.69 (d, $^3$J (H,H)=8 Hz, 1H; Ar—H), 7.54 (t, $^3$J (H,H)=7.5 Hz, 1H; Ar—H), 4.29 (t, $^3$J (H,H)=8 Hz, 2H; α-CH$_2$), 2.82 (t, $^3$J (H,H)=8 Hz, 2H; β-CH$_2$), 2.71 (q, $^3$J (H,H)=8 Hz, 4H; —N—(CH$_2$)—), 1.14 (t, $^3$J (H,H)=7.5 Hz, 6H; CH$_3$) ppm; $^{13}$C NMR (125 MHz, CDCl$_3$): δ=163.75, 163.74, 136.23, 136.08, 132.77, 131.34, 131.26, 131.16, 130.01, 129.41, 129.35, 128.79, 128.77, 128.10, 126.22, 126.05, 124.21, 123.52, 121.20, 121.18, 120.55, 120.27, 50.09, 47.94, 38.26, 12.58 ppm; UV-vis (5.6×10$^{-5}$ M, CHCl$_3$) λ$_{max}$(ε, M$^{-1}$ cm$^{-1}$)=513 nm (35,600), 488 nm (36,000); IR (KBr): ν=2966 (m), 1693 (s), 1647 (s), 1592 (s), 1562 (s), 1496 (w), 1365 (s), 1294 (w), 1244 (m), 1162 (m), 1113 (w), 1064 (w), 804 (s), 748 (s) cm$^{-1}$; HRMS (FAB, m/z) Calcd for C$_{28}$H$_{24}$BrN$_2$O$_2$ (MH$^+$), 499.1021. found: 499.1004.

9,9'-Bis-[(N,N-diethylammoniumethyl)perylene-3,4-dicarboxylicimide]diacetate (6)

A total of 0.48 g (2.0 mmol) of NiCl$_2$.6H$_2$O was dissolved in 47 mL of DMF in a 100-mL round-bottomed flask. The solution was purged with argon for 20 minutes. Then the solution was warmed to 50° C. and 2.10 g (8.0 mmol) of triphenylphosphine were added and dissolved while stirring under N$_2$. After 10 minutes, 0.25 g (4.0 mmol) of zinc dust (325 mesh) were added, and the mixture was stirred vigorously under N$_2$. The solution changed color over the course of 30 min from blue to red. After 1 h of stirring under N$_2$ at 50° C., 1.00 g (2.0 mmol) of compound 5 was added, and a condenser was fit to the round-bottomed flask. After stirring at 50° C. for another 4.5 h, the reaction mixture was allowed to cool, and the product that precipitated was filtered, washed with acetone, and dried. The solid was then dissolved in 30 mL of boiling glacial acetic acid (AcOH). After cooling, 70 mL of chloroform were added and the solution was filtered through a pad of cellulose in a 60-mL fritted glass funnel. The cellulose was washed with excess chloroform. The filtrate was rotaevaporated to remove most of the AcOH. A total of 10 mL of chloroform and 100 mL of ethylacetate (EtOAc) were added. The solution was kept at ~0° C. for 2 h. The precipitate was then filtered off and washed with excess EtOAc. The resulting solid was dark purple/red and was sonicated with diethyl ether (Et$_2$O) and then filtered and washed with excess Et$_2$O in order to remove residual acetic acid. The solid 6 was dried under vacuum to weigh 840 mg (0.88 mmol, 88%). $^1$H NMR (500 MHz, CDCl$_3$): δ=8.61 (d, $^3$J (H,H)=8.5 Hz, 2H; Ar—H), 8.59 (d, $^3$J (H,H)=8.5 Hz, 2H; Ar—H), 8.58 (d, $^3$J (H,H)=8 Hz, 2H; Ar—H), 7.72 (d, $^3$J (H,H)=8 Hz, 2H; Ar—H), 7.56 (d, $^3$J (H,H)=8 Hz, 2H; Ar—H), 7.50 (t, $^3$J (H,H)=6.8 Hz, 2H; Ar—H), 4.41 (unresolved t, 4H; α-CH$_2$—), 3.04 (broad, 4H; —CH$_2$—NR$_2$), 2.93 (multiplet, 8H; —N—(CH$_2$)—), 2.04 (s, 6H; acetate —CH$_3$), 1.24 (t, $^3$J (H,H)=6.8 Hz, 12H; CH$_3$) ppm; $^{13}$C NMR (125 MHz, CDCl$_3$): δ=164.1, 140.79, 137.53, 137.32, 133.84, 131.94, 130.06, 129.70, 129.67, 129.64, 129.45, 128.40, 127.64, 126.92, 124.30, 123.62, 121.17, 121.11, 120.80, 120.65, 49.02, 47.57, 36.71, 11.23 ppm; UV (2.7×10$^{-7}$ M in CHCl$_3$) λ$_{max}$ (ε, M$^{-1}$ cm$^{-1}$)=534 nm (47,000); IR (KBr): ν=3435, 1691, 1655, 1592, 1572, 1364, 1293, 1064, 812, 753, 672 cm$^{-1}$; HRMS (FAB, m/z) Calcd for C$_{56}$H$_{47}$N$_4$O$_4^+$(M$^{2+}$—H$^+$) 839.3597. found: 839.3607.

Bis-(N,N-diethylammoniumethyl)quaterrylene-3,4: 13,14-tetracarboxylic diimide diformate (Ia) and derivatives Ib A total of 1.01 g (1.20 mmol) of the acetate salt 6, 10 g of d-glucose (55.5 mmol), approximately 150 g of KOH pellets (2.3 mol), and 200 mL of absolute ethanol were added to a 500-mL round-bottomed flask. The mixture was heated at 135° C. under nitrogen for 3 hours. After cooling to RT, 200 mL of water were added to dissolve all of the KOH and glucose. The undissolved solid was filtered, and washed with hot water and acetone. After drying under vacuum, the solid 7 was dissolved in formic acid. Addition of diethyl ether to the formic acid solution resulted in the formation of a blue precipitate of Ia and a red solid of the unreacted compound 6. The solid mixture was filtered and dried under vacuum. The solid mixture was then refluxed in chloroform for 30 min. to dissolve the unreacted compound 6, and the undissolved formate salt Ia was filtered and washed with chloroform, and dried under vacuum to yield 0.51 g (0.54 mmol, 45%) of Ia. Other attempts with longer times for the oxidative aromatization gave yields as high as 60%. $^1$H-NMR (300 MHz, D$_2$SO$_4$): δ=8.89 (br, Ar—H), 8.67 (br, Ar—H), 8.42 (br, Ar—H)—(all three peaks integrate to 16H), 5.78 (br, 2H; N—H), 4.46 (br, 4H; α-CH$_2$), 3.07 (br, 4H; β-CH$_2$), 2.80 (br, 8H; —N—(CH$_2$)—), 0.79 (t, 12H; CH$_3$) ppm; IR (KBr): ν=1685 (s), 1647 (s), 1573 (s), 1361 (s), 1286 (m), 1245 (w), 1220 (w), 1150 (w), 1099 (w), 1063 (m), 840 (m), 808 (s), 785 (w), 749 (m) cm$^{-1}$; HRMS (FAB, m/z) Calcd for C$_{56}$H$_{45}$N$_4$O$_4$ (M$^{2+}$—H$^+$), 837.34409. found: 837.3461.

Reaction of 7 with alkyl halides or methyl toluenesulfonate resulted in Ib (not shown in Scheme 1).

The synthesis of Ia and its $^1$H-NMR and UV-visible properties have been reported in S-W. Tam-Chang et al. (2004) J. Org. Chem. 69:2719-2726. As reported in S-W. Tam-Chang, W. Seo, I. K. Iverson, and S. M. Casey (2003) "Ionic Quaterrylenebis(dicaroxyimide): A Novel Mesogen and Long-Wavelength Polarizing Material" Angew. Chem. Int. Ed. 42(8):897-900. (Feb. 21, 2003) the compound of formula Ia where A is HCOO$^-$ exhibits long-wavelength electronic absorption in aqueous solution (aqueous formic acid) which varies with the concentration of formic acid, and in some cases varied with temperature and the concentration of the ionic carboximide in solution. Solutions of the ionic carboximide in 16.5 N formic acid were birefringent at concentrations of 4 wt % and greater indicating the formation of a lyotropic liquid-crystalline phase (P. J. Collings, J. S. Patel (1997) *Handbook of Liquid Crystal Research*, Oxford University Press, New York.) The optical textures observed in optical photomicrographs of solutions of the ionic carboximide (8 wt. % in 16.5 N HCOOH) in crossed polarizers are consistent with a chromonic, nematic liquid crystalline phase[16] (J. Lydon (1998) Curr. Opin. Colloid Interface Sci. 3:458-466). Oriented thin solid films of compound 1a were prepared by simultaneously coating and aligning a solution of the ionic compound in the chromonic nematic phase onto glass substrates by application of mechanical shearing force and solvent evaporation. The results observed indicated that the molecules were oriented in the film with their electronic transition moments perferentially aligned orthogonal to the shearing direction.

Example 2

In this example, compounds IIa-d were synthesized according to the procedure described below. Compounds of formula II where R is negatively charge have formula:

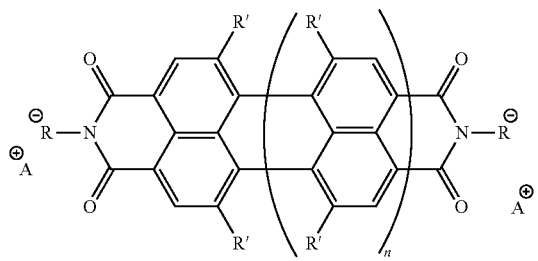

Compounds IIa-d have above formula where n is 1, R' is H, R is —CHR"COO⁻ and R" is H or alkyl and with suitable counterion (e.g., K⁺): for Compound IIa, R" is H, for Compound IIb, R" is methyl; for Compound IIc, R" is —CH(CH$_3$)$_2$, and for Compound IId, R" is —CH$_2$CH(CH$_3$)$_2$.

Perylenetetracarboxylic dianhydride (PTCA) (3.52 g, 8.97 mmol) was suspended in dimethyl sulfoxide (DMSO, 338 mL) and heated to about 100° C. A solution of glycine (16.84 g, 224.31 mmol) and 87.6% KOH (14.37 g, 224.31 mmol) in water (25 mL) was added drop-wise to the suspension. The mixture was stirred at about 100° C. for 3 hours. The resulting suspension was cooled to RT and the precipitate was collected by vacuum filtration. The residue was washed with a DMSO/water mixture (v/v=67:33) and methanol. To remove DMSO from the product, the dipotassium salt was recrystallized from water and acetone. The resulting solid was filtered and washed twice with acetone. The reddish solid of IIa was dried under vacuum overnight. Yield: 3.45 g, 5.92 mmol, 66%. ¹H NMR (500 MHz, CDCl$_3$): δ=8.32 (unresolved d, 4H; Ar—H), 8.08 (unresolved d, 4H; Ar—H), 5.07 (s, 4H; —CH$_2$—) ppm; ¹³C NMR (300 MHz, D$_2$O): δ=174.65, 163.46, 132.63, 131.16, 126.87, 123.36, 120.65, 44.14 ppm.

PTCA (0.515 g, 1.312 mmol) was suspended in DMSO (50 mL) and heated to about 100° C. A solution of L-alanine (3.221 g, 32.799 mmol) and 87.6% KOH (2.101 g, 32.799 mmol) in water (25 mL) was added drop-wise to the suspension. The mixture was stirred at about 100° C. for 3 hours. The resulting suspension was cooled to RT and the precipitate was collected by vacuum filtration. The residue was washed with a DMSO/water mixture (v/v=67:33) and methanol. The solid was recrystallized from water and acetone, filtered, and washed with acetone. The collected reddish solid (IIb) was dried under vacuum overnight. Yield: 0.59 g, 0.97 mmol, 74%. ¹H NMR (500 MHz, D$_2$O, 85° C.): δ=8.49 (d, 4H, ³J (H,H)=7.5 Hz; Ar—H), 8.08 (d, 4H, ³J (H, H)=5.5 Hz; Ar—H), 6.01 (q, 2H, ³J (H, H)=7 Hz; α-CH—), 2.35 (d, 6H, ³J (H, H)=7.5 Hz; CH$_3$) ppm; ¹³C NMR (300 MHz, D$_2$O): δ=177.6, 163.5, 132.5, 130.7, 127.1, 123.4, 122.8, 121.3, 52.5, 15.7 ppm.

PTCA (1.295 g) was suspended in DMSO (100 mL) and heated to about 100° C. A solution of L-valine (7.836 g, 66.222 mmol) and 87.6% KOH (4.242 g, 66.222 mmol) in water was added drop-wise to the suspension. The mixture was stirred at about 100° C. for 3 hours. The resulting suspension was cooled to RT and the precipitate was collected by vacuum filtration. The collected residue (IIc) was washed with a DMSO/water mixture (v/v=67:33) and acetone and dried under vacuum at 170° C. overnight. Yield: 1.63 g, 2.53 mmol, 77%. ¹H NMR (500 MHz, D$_2$O, 85° C.): δ=8.38 (d, 4H, ³J(H,H)=5 Hz; Ar—H), 7.51 (unresolved d, 4H; Ar—H), 5.60 (d, 2H, ³J (H,H)=8.5 Hz; α-CH—), 3.34 (unresolved multiplet, 2H; β-CH—), 1.91 (d, 6H, ³J(H,H)=4.5 Hz; CH$_3$), 1.50 (d, 6H, ³J(H,H)=5.5 Hz; CH$_3$) ppm; ¹³C NMR (300 MHz, D$_2$O): δ=176.65, 164.55, 133.34, 131.51, 128.16, 124.65, 122.94, 122.00, 62.62, 28.22, 22.94, 19.98 ppm.

PTCA (2.15 g, 5.371 mmol) was suspended in DMSO (215 mL), and the suspension was heated to 100° C. A solution of L-leucine (2.846 g, 21.482 mmol) and 87.6% KOH (1.376 g, 21.482 mmol) in warm water (107 ml) was added drop-wise to the suspension, and the mixture was stirred at 100° C. for 4 hours. The resulting suspension was cooled to RT and the suspended solids were collected by vacuum filtration. The collected residue was stirred with a DMSO/water mixture (v/v=67:33) for about an hour. The solid (IId) was filtered, washed with acetone, and dried under vacuum at 100° C. overnight. Yield: 2.43 g, 3.5 mmol, 65%. ¹H NMR (500 MHz, D$_2$O): δ=8.33 (d, 4H, ³J(H,H)=5.5 Hz; Ar—H), 7.57 (unresolved d, 4H; Ar—H), 6.08 (unresolved t, 2H; α-CH—), 2.84 (unresolved multiplet, 4H; β-CH$_2$—), 2.16 (unresolved multiplet, 2H; γ-CH—), 1.75 (d, 6H, ³J(H,H)=8.0 Hz; CH$_3$), 1.73 (d, 6H, ³J(H,H)=7.0 Hz; CH$_3$) ppm; ¹³C NMR (500 MHz, D$_2$O): δ=176.50, 163.81, 132.68, 130.60, 127.72, 124.33, 122.12, 55.55, 38.75, 26.30, 23.15, 21.82 ppm.

Studies by polarized optical microscopy showed that compounds IIb-d exhibit chiral lyotropic liquid-crystalline properties in aqueous solution.

Example 3

In this example, monoimide IIIa-k were synthesized according to the procedure described below (Scheme 2). In addition, studies by polarized optical microscopy showed that these compounds exhibit lyotropic liquid-crystalline properties in aqueous solution. These compounds also exhibit fluorescence properties in solution (aqueous or organic) and in solid phase. Some of these compounds (including, but not limited to compounds IIIc, IIIf-IIIk) exhibit uv-vis absorption properties that are pH dependent and fluorescence properties that are dependent on the solvent, pH, and the absence or presence of biologically relevant molecules such as nucleic acids (DNA, RNA, and oligonucleotides.)

Scheme 2: Synthesis of Monoamides III

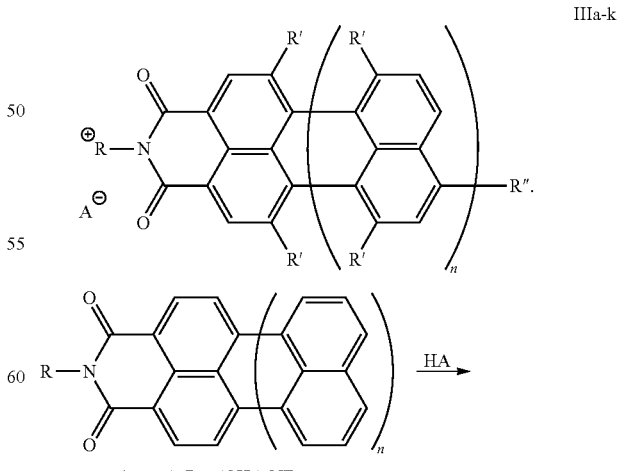

4: n = 1, R = (CH$_2$)$_2$NEt$_2$,

IIIa: n = 1, R = (CH$_2$)$_2$NHEt$_2$, A = Cl, HCOO, or C$_6$H$_4$SO$_3$

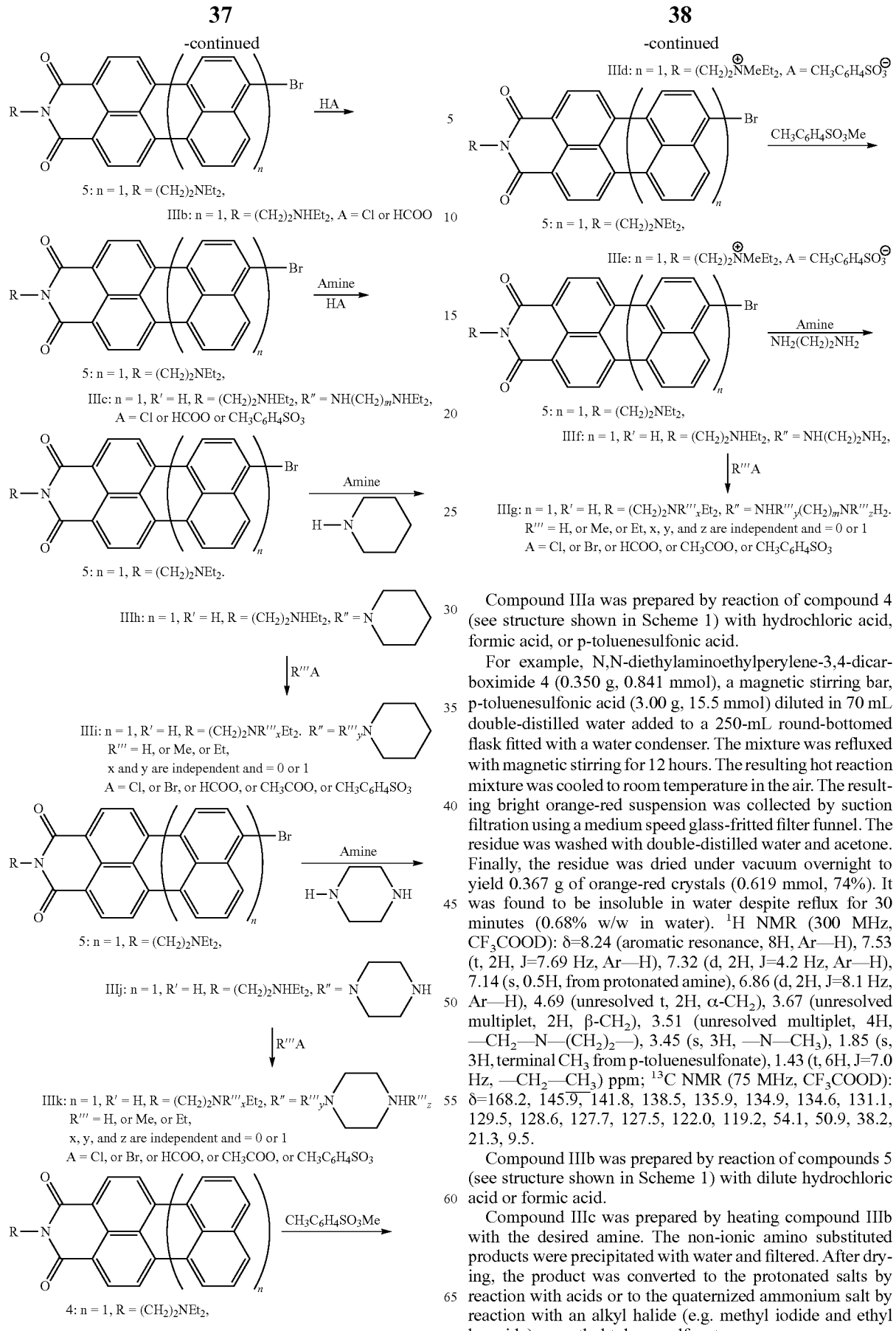

Compound IIIa was prepared by reaction of compound 4 (see structure shown in Scheme 1) with hydrochloric acid, formic acid, or p-toluenesulfonic acid.

For example, N,N-diethylaminoethylperylene-3,4-dicarboximide 4 (0.350 g, 0.841 mmol), a magnetic stirring bar, p-toluenesulfonic acid (3.00 g, 15.5 mmol) diluted in 70 mL double-distilled water added to a 250-mL round-bottomed flask fitted with a water condenser. The mixture was refluxed with magnetic stirring for 12 hours. The resulting hot reaction mixture was cooled to room temperature in the air. The resulting bright orange-red suspension was collected by suction filtration using a medium speed glass-fritted filter funnel. The residue was washed with double-distilled water and acetone. Finally, the residue was dried under vacuum overnight to yield 0.367 g of orange-red crystals (0.619 mmol, 74%). It was found to be insoluble in water despite reflux for 30 minutes (0.68% w/w in water). $^1$H NMR (300 MHz, CF$_3$COOD): δ=8.24 (aromatic resonance, 8H, Ar—H), 7.53 (t, 2H, J=7.69 Hz, Ar—H), 7.32 (d, 2H, J=4.2 Hz, Ar—H), 7.14 (s, 0.5H, from protonated amine), 6.86 (d, 2H, J=8.1 Hz, Ar—H), 4.69 (unresolved t, 2H, α-CH$_2$), 3.67 (unresolved multiplet, 2H, β-CH$_2$), 3.51 (unresolved multiplet, 4H, —CH$_2$—N—(CH$_2$)$_2$—), 3.45 (s, 3H, —N—CH$_3$), 1.85 (s, 3H, terminal CH$_3$ from p-toluenesulfonate), 1.43 (t, 6H, J=7.0 Hz, —CH$_2$—CH$_3$) ppm; $^{13}$C NMR (75 MHz, CF$_3$COOD): δ=168.2, 145.9, 141.8, 138.5, 135.9, 134.9, 134.6, 131.1, 129.5, 128.6, 127.7, 127.5, 122.0, 119.2, 54.1, 50.9, 38.2, 21.3, 9.5.

Compound IIIb was prepared by reaction of compounds 5 (see structure shown in Scheme 1) with dilute hydrochloric acid or formic acid.

Compound IIIc was prepared by heating compound IIIb with the desired amine. The non-ionic amino substituted products were precipitated with water and filtered. After drying, the product was converted to the protonated salts by reaction with acids or to the quaternized ammonium salt by reaction with an alkyl halide (e.g. methyl iodide and ethyl bromide) or methyl toluenesulfonate.

Compound IIId was synthesized according to the procedure described below. N,N-Diethylaminoethylperylene-3,4-dicarboximide 4 (1.83 g, 4.35 mmol), a magnetic stirring bar, and chloroform (50 mL) were added to a 250-mL round-bottomed flask fitted with a water condenser. Methyl p-toluenesulfonate (8.34 g, 43.5 mmol) diluted in chloroform (50 mL) was added to the flask. The mixture was refluxed in a hot oil bath with magnetic stirring for one hour. The resulting hot reaction mixture was cooled to room temperature. The resulting red suspension was collected by suction filtration using a medium porosity glass-fritted filter funnel. The residue was washed with chloroform and anhydrous diethyl ether and dried under vacuum overnight to yield 2.10 g of red solid (80%). $^1$H NMR (500 MHz, CF$_3$COOD): δ=8.22 (d, 2H, $^3$J (H,H)=8.0 Hz, Ar—H), 8.07 (d, 2H, $^3$J (H,H)=7.5 Hz, Ar—H), 7.91 (d, 2H, $^3$J (H,H)=9.0 Hz, Ar—H), 7.89 (d, 2H, $^3$J (H,H)=8.0 Hz, Ar—H), 7.73 (d, 2H, $^3$J (H,H)=8.0 Hz, Ar—H), 7.55 (dd, 2H, $^3$J (H,H)=7.5 and 8.0 Hz, Ar—H), 7.21 (d, 2H, $^3$J (H,H)=8.0 Hz, Ar—H), 4.88 (t, 2H, $^3$J (H,H)=7.7 Hz, α-CH$_2$), 3.82 (unresolved m, 6H, —CH$_2$—N—( CH$_2$)$_2$—), 3.45 (s, 3H, —N—CH$_3$), 2.26 (s, 3H, terminal CH$_3$ from p-toluenesulfonate), 1.76 (t, 6H, $^3$J (H,H)=7.0 Hz, —CH$_2$—CH$_3$) ppm; $^{13}$C NMR (75 MHz, CF$_3$COOD): δ=167.5, 146.0, 141.9, 139.0, 136.0, 134.9, 134.5, 131.6, 131.2 129.6, 129.0, 128.8, 128.0, 127.8, 127.4, 122.1, 119.3, 60.2, 58.9, 49.5, 36.0, 21.5, 8.6 ppm; UV (H$_2$O, 1.7×10$^{-5}$ M) λ$_{max}$=465 (ε=17600), 500 (ε=36700), 540 (ε=19900) nm. UV (H$_2$O, 3.2×10$^{-4}$ M) λ$_{max}$=485 nm (ε=18,588), UV (formic acid (aq., 0.47N), 3.1×10$^4$M) λ$_{max}$=483 nm (ε=16,716); IR (KBr): ν=1690, 1653, 1590, 1499, 1460, 1365, 1291, 1195, 1119, 1034, 814, 754, 679, 566; m.p.: 274° C. (decomposed).

Compound IIIf: In this example, a diamine (1° amino groups at both end) is used to illustrate the synthesis of compound of general structure III. A total of 0.236 g of compound 5 was added into 10 mL of distilled ethylenediamine. The mixture was stirred under nitrogen at about 130° C. for about 1 day. Excess ethylenediamine was removed by distillation. The residual solid was purified by column chromatography. The ether was added to the eluent that contained IIIf. Solid of compound IIIf was collected by suction filtration, washed with ether, and dried under vacuum at room temperature overnight. A total of 0.035 g of IIIf was obtained. Compound IIIf was converted to IIIg by reaction with the desired acid.

Compound IIIh: In this example, a cyclic amine (piperidine) is used to illustrate the synthesis of compound of general structure III. A total of 0.106 g of compound 5 was added into 10 mL of distilled piperidine. The mixture was refluxed under nitrogen for about 1 day. Excess piperidine was removed by distillation. Diethylether was added to the residual mixture and IIIh precipitated from solution. Solid of compound IIIh was collected by suction filtration, washed with ether and ethanol, and dried under vacuum at room temperature overnight. The solid was then dissolved into chloroform and extracted multiple times with 2M HCl (aq). The combined aqueous solution was converted into basic pH by addition of a basic solution (e.g., 5% NaOH (aq). Compound IIIh was then extracted from the aqueous solution into chloroform. The combined chloroform extract was dried with anhydrous sodium sulfate. Chloroform was removed by rotary evaporation, and the solid remained was dried under vacuum at about 70° C. overnight. A total of 0.061 g of IIIh was obtained. $^1$H NMR (300 MHz, CDCl$_3$) δ ppm: 8.46 (d, 1H, Ar—H), 8.44 (d, 1H, Ar—H), 8.34 (d, 1H, Ar—H), 8.27 (d, 1H, Ar—H), 8.24 (d, 1H, Ar—H), 8.18 (d, 1H, Ar—H), 8.16 (d, 1H, Ar—H), 7.58 (t, 1H, Ar—H), 7.13 (d, 1H, Ar—H), 4.29 (t, 2H, CH$_2$), 3.17 (broad, 4H, Ar—NCH$_2$), 2.81 (t, 2H, —CH$_2$), 2.71 (q, 4H, —NCH$_2$CH$_3$), 1.90 (multiplet, 4H, —CH$_2$ piperidine), 1.72 (broad, 2H, —CH$_2$), 1.14 (t, 6H, CH$_3$). Compound IIIh was converted to IIIi by reaction with the desired acid.

Compound IIIj: In this example, a cyclic diamine (piperazine) is used to illustrate the synthesis of compound of general structure III. A total of 0.107 g of compound 5 and 1.5 g of piperazine was added to 1 mL of DMSO. The mixture was stirred under nitrogen at about 140° C. for about 1 day. After the mixture was cooled to room temperature, diethylether was added and IIIj precipitated from solution. Solid of compound IIIj was collected by suction filtration, washed with ether and ethanol, and dried under vacuum at room temperature overnight. The solid was then dissolved into chloroform and extracted multiple times with 2M HCl (aq). The combined aqueous solution was converted into basic pH by addition of a basic solution (e.g., 5% NaOH (aq)). Compound IIIj was then extracted from the aqueous solution into chloroform. The combined chloroform extract was dried with anhydrous sodium sulfate. Chloroform was removed by rotary evaporation, and the solid remained was dried under vacuum at about 70° C. overnight. A total of 0.043 g of IIIj was obtained. $^1$H NMR (300 MHz, CDCl$_3$) δ ppm: 8.29 (d, 1H, Ar—H), 8.27 (d, 1H, Ar—H), 8.18 (d, 1H, Ar—H), 8.15 (d, 1H, Ar—H), 8.12 (d, 1H, Ar—H), 8.04 (d, 1H, Ar—H), 7.97 (d, 1H, Ar—H), 7.51 (t, 1H, Ar—H), 7.09 (d, 1H, Ar—H), 4.24 (t, 2H, —CH$_2$), 3.20 (broad, 8H, Ar—NCH$_2$CH$_2$NH), 2.79 (t, 2H, —CH$_2$), 2.70 (q, 4H, 8 Hz, —NCH$_2$CH$_3$), 1.14 (t, 6H, CH$_3$). Compound IIIj was converted to IIIk by reaction with the desired acid.

Compounds with the general structure of III (including compound 4 and 5) exhibit anisotropic fluorescence properties in solid phase, as well as solvent- and pH-dependent fluorescence properties in solution. For example, the uv-vis spectrum of IIIf in aqueous buffer solutions ranging in pH from about 3 to about 10 exhibits significant variation useful pH determination. At acidic pH the predominant form is expected to be IIIg. For example, the fluorescence emission spectrum of IIIh in solutions containing aqueous buffer (TE buffer pH 7.7 and methanol shows significant variation as the volume ratio of aqueous buffer to methanol is changed from 100:0 to 10:90. Fluorescence emission of these compounds is affected by exposure to biological molecules (e.g., nucleic acids). For example, the fluorescence spectrum of IIIj (~10$^{-6}$M) in aqueous buffer pH 7.7 exhibits a significant change in fluorescence intensity in the presence of an oligonucleotide. The double stranded oligonucleotide used in this example has a DNA backbone and comprised of one strand with sequence (5' to 3') of TGG GAG GGA GGG AGG GAG AG hybridized to its complementary strand. The excitation spectrum was collected at emission wavelength of 680 nm and emission spectrum was collected at emission wavelength of 540 nm.

Example 4

In this example, compounds IVa-f were synthesized according to procedure outlined in Scheme 3. In addition, studies were performed using compound IVe as an example to provide evidence for the formation of lyotropic chromonic liquid-crystalline phase and the fabrication of anisotropic materials that consist of a single lyotropic mesogen or a mixture of lyotropic mesogens.

Scheme 3. Synthetic scheme for compounds IVa-f

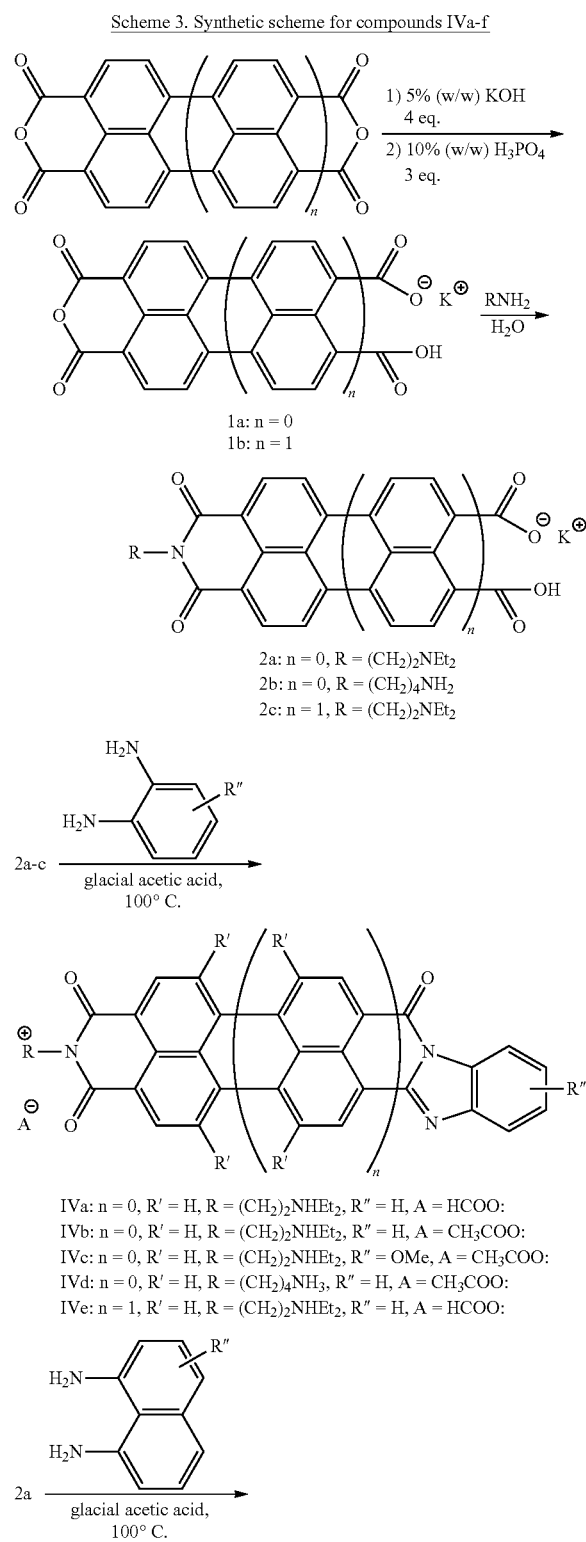

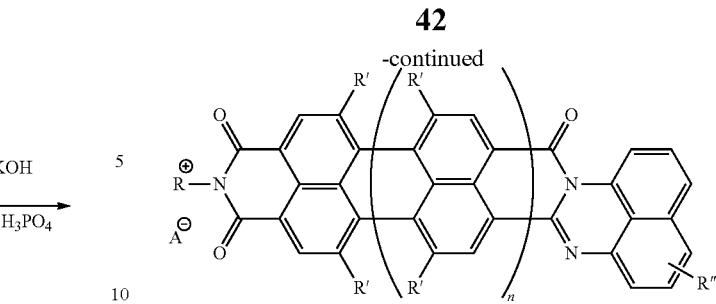

IVf: n = 0, R' = H, R = (CH$_2$)$_2$NHEt$_2$, R'' = H, A = CH$_3$COO:

1,4,5,8-Naphthalene tetracarboxylic dianhydride (5.217 g, 19.45 mmol) and KOH (4.441 g, 79.15 mmol) were stirred at 90° C. in distilled water (101 ml) for 3.5 h. To this solution, a 10% phosphoric acid solution (5.5867 g H$_3$PO$_4$ in 55 mL H$_2$O) was added drop-wise until the pH of the solution was between pH 4.0-5.0. A precipitate was formed during the addition of the acid. The mixture was stirred at about 90° C. for 3 h, cooled to RT, and the solid was filtered. The filtered solid, 1a was washed with distilled water and dried. (Yield: 5.930 g, 18.29 mmol, 94%).

Compound 1a (0.8904 g, 2.75 mmol) was stirred in 15 mL of distilled water for 5 min. N,N-diethyl ethylenediamine (1.8941 g, 16.30 mmol) was added. After the solution was stirred overnight, it was poured into 250 mL of acetone and the resulting solution turned cloudy. The mixture was allowed to sit for about 1 h. During this time an off-white solid precipitated out. The solid 2a was filtered, washed with acetone, and dried. (Yield: 1.117 g, 2.64 mmol, 96%)

Compound 2a (0.574 g, 1.36 mmol) and o-phenylenediamine (0.450 g, 4.16 mmol) were stirred in 15 mL of glacial acetic acid at about 100° C. for 17 h. The solution was cooled to RT and poured into 200 mL of diethyl ether. This caused the immediate precipitation of an orange solid. The orange solid IVb was collected by filtration, washed with ether, and dried under vacuum overnight (this caused loss of acetic acid from the acetate salt to yield the neutral amine). (Yield (neutral form): 0.459 g, 1.05 mmol, 77%). The compound was redissolved in formic acid or glacial acetic acid, crashed out in diethyl ether, filtered, and washed with ether. The solid obtained was air-dried to give the formate salt, IVa, or the acetate salt, IVb.

Compound 2a (0.489 g, 1.16 mmol), 4-methoxy-1,2-phenylenediamine dihydrochloride (0.736 g, 3.49 mmol), and 20 mL of glacial acetic acid were stirred at about 100° C. for 17 h. The solution was cooled to RT then poured into 200 mL of diethyl ether. This caused the precipitation of a red-brown solid that was then filtered, washed with ether, and dried overnight under vacuum. This crude product was stirred in 1.8 M KOH for 15 min. The undissolved red-orange solid, IVc (two isomers), was collected by centrifugation, rinsed with acetone, filtered, and dried. (0.353 g, 0.753 mmol, 65%)

Compound 1a (1.420 g, 4.38 mmol) was stirred in neat 1,4-diaminobutane (9.3906 g, 106.53 mmol) at about 100° C. overnight. The solution was allowed to cool to RT and then 50 mL of ether were added. The solid precipitate was filtered, washed with acetone and ether, and dried by aspiration. The crude solid was stirred in distilled water (about 40 mL) at 80° C. overnight. After the solution was filtered to remove any undissolved solid, about 350 mL of acetone were added. The crude solid, 2b, that precipitated out was filtered, washed with acetone and ether, and dried by aspiration. Compound 2b (~1.338 g, 3.39 mmol) and o-phenylenediamine (1.142 g, 10.53 mmol) were stirred in 30 mL of glacial acetic acid at 100° C. overnight. The solution was allowed to cool to RT and then poured into 200 mL of ether. The yellow-orange precipitate was filtered, washed with ether, and dried by aspiration. The solid was added to 80 mL of acetic acid, and the undissolved material was removed by centrifugation. The supernate was poured into 400 mL of diethyl ether causing a yellow-orange solid to precipitate out. The yellow-orange solid, IVd, was filtered, washed with ether, and dried by aspiration. (Yield: 0.438 g, 0.930 mmol, 27%)

The monopotassium salt of PTCA (1b, 1.01 g, 2.25 mmoles) was suspended in water (30 mL) and N,N-diethylene diamine (1.04 g, 9.19 mmoles) was added. The mixture was stirred at RT for an hour. Into the resulting solution, 100 mL of acetone was added to induce precipitation. The precipitates were filtered and washed with acetone and diethyl ether. The solid was dried under vacuum to yield 0.963 g (78.3%) of 2c. $^1$H-NMR (300 MHz, [D]TFA): δ=8.72 (d, 2H, $^3$J (H,H)=6.6 Hz; Ar—H), 8.51 (d, 2H, $^3$J (H,H)=7.3 Hz; Ar—H), 8.49 (d, 2H, $^3$J (H,H)=7.7 Hz; Ar—H), 8.32 (d, 2H, $^3$J (H,H)=7.0 Hz; Ar—H), 7.34 (s, 1H; N—H), 4.83 (unresolved t, 2H; α-CH$_2$—), 3.90 (unresolved t, 2H; β-CH$_2$—), 3.68 (unresolved multiplet, 4H; —N—(CH$_2$)—), 1.55 (unresolved t, 6H; CH$_3$) ppm; $^{13}$C-NMR (300 MHz, [D]TFA): δ=167.80, 138.63, 137.41, 136.72, 135.61, 133.29, 131.32, 128.18, 127.04, 126.86, 124.33, 119.80, 55.23, 50.76, 38.54, 9.53 ppm.

O-penylenediamine (0.3767 g), dissolved in 30 mL of acetic acid, was added to 0.943 g of 2c. The mixture was heated to about 100° C. for an hour. After cooling to RT, 100 mL of diethyl ether were added. The resulting solid obtained by filtration was then dissolved in concentrate formic acid. Addition of diethyl ether resulted in the precipitation of the formate salt. The formate salt was dried under vacuum at about 110° C. to yield 0.793 g of the neutral form of IVe. $^1$H-NMR (300 MHz, [D]TFA): δ=9.160 (Ar—H), 9.133 (Ar—H), 9.090 (Ar—H), 9.065 (Ar—H), 9.032 (Ar—H), 9.015 (Ar—H), 8.973 (Ar—H), 8.948 (Ar—H), 8.851 (Ar—H), 8.823 (Ar—H)—(overlapping resonance, all ten peaks integrate to 9H), 7.90 (Ar—H), 7.81 (Ar—H)—(both peaks integrate to 3H), 7.45 (broad, 1H; N—H), 4.76 (unresolved t, 2H; α-CH$_2$—), 3.68 (unresolved t, 2H; β-CH$_2$—), 3.49 (unresolved multiplet, 4H; —N—(CH$_2$)—), 1.44 (t, 6H, $^3$J (H,H) =6.6 Hz; CH$_3$) ppm; $^{13}$C-NMR (300 MHz, [d]TFA): δ=169.88, 168.31, 161.44, 148.84, 140.51, 137.98, 135.76, 133.76, 132.76, 132.19, 131.76, 131.18, 130.63, 129.44, 128.59, 128.15, 128.00, 127.64, 127.28, 124.91, 123.86, 119.52, 119.27, 117.90, 116.33, 115.52, 115.37, 115.14, 114.14, 57.94, 51.67, 38.81, 9.90 ppm. This product was converted back to the formate salt, IVe, by reaction with formic acid.

Compound 2a (0.529 g, 1.25 mmol) and 1,8-diaminonaphthalene (0.814 g, 5.15 mmol) were stirred at about 100° C. in 25 mL of glacial acetic acid for 19 h. After the solution was allowed to cool to RT, 250 ml of diethyl ether were added. This caused the precipitation of a dark purple precipitate that was filtered, washed with ether, and dried by aspiration. Excess 1,8-diaminonaphthalene was removed by stirring the crude product in ether overnight. The purple solid, IVf, was collected by filtration, washed with ether, and dried by aspiration. (Yield: 0.4473 g, 0.815 mmol, 65%). $^1$H NMR (300 MHz, [D]TFA): δ=9.12 (1H; Ar—H), 9.03 (1H; Ar—H), 8.94 (2H; Ar—H), 8.37 (1H; Ar—H), 7.7-7.37 (6H; Ar—H), 7.3 (1H; —NH$^+$), 4.72 (2H; N—CH$_2$), 3.67 (2H; N—CH$_2$—), 3.48 (4H; —NCH$_2$), 2.17 (3H; CH$_3$COO), 1.44 (6H; CH$_2$) ppm.

Example 5

In this example, compounds Va-d were synthesized according to procedure outlined in Scheme 4. Studies by polarized optical microscopy showed that these compounds exhibit lyotropic liquid-crystalline properties. In addition, studies were performed using compound Va and Vc as examples to provide evidence for the formation of lyotropic chromonic liquid-crystalline phase and the fabrication of anisotropic materials.

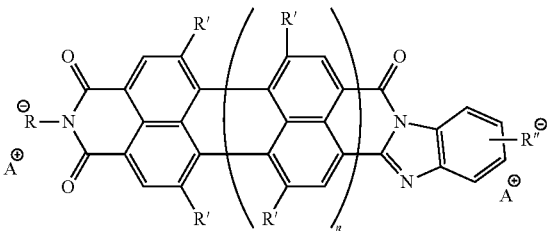

Va-d

Scheme 4. Synthetic scheme for compounds V.

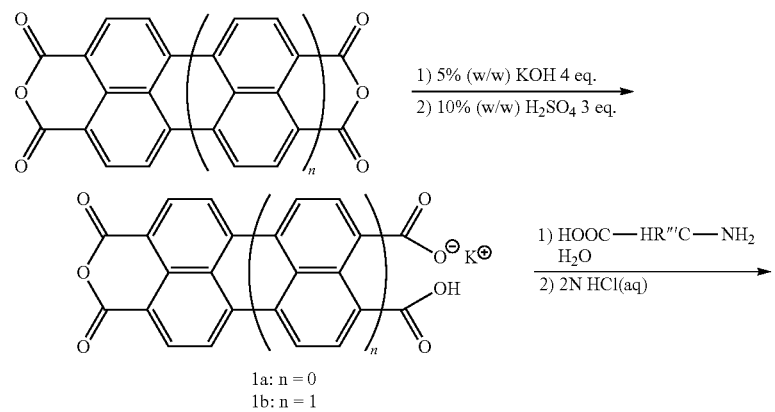

1a: n = 0
1b: n = 1

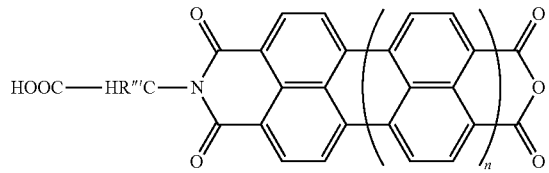
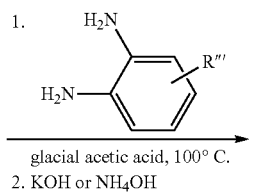

glacial acetic acid, 100° C.
2. KOH or NH₄OH

8a: n = 1, R''' = H
8b: n = 1, R''' = CH(CH₃)₂

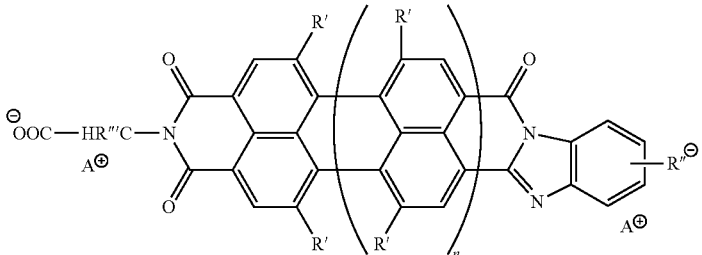

Va: n = 1, R' = H, R'' = COO, R''' = H, A = K
Vb: n = 1, R' = H, R'' = COO, R''' = H, A = NH₄
Vc: n = 1, R' = H, R'' = COO, R''' = CH(CH₃)₂, A = K
Vd: n = 1, R' = H, R'' = COO, R''' = CH(CH₃)₂, A = NH₄

The monopotassium salt (Ib) of PTCDA (3.0160 g, 6.73 mmol) was suspended in hot (~90° C.) DMSO (~200 mL). A solution of glycine (2.020 g, 26.90 mmol) and 87.6% KOH (1.723 g, 26.90 mmol) in water (~100 mL) was added dropwise to the hot suspension. After the addition was completed, the reaction mixture was stirred for 3 hours at about 90° C. The resulting mixture was allowed to cool to RT, and then the precipitate was collected by vacuum filtration. The residue collected was dissolved in about 200 mL of doubly-distilled water. The resulting solution was vacuum filtered to remove undissolved particles. 2 N HCl (aq, ~30 ml) was added to the filtrate and the mixture was stirred at about 90° C. for an hour. The precipitate formed was collected by vacuum filtration, washed with hot doubly-distilled water (400 mL), and dried under vacuum overnight to yield 2.71 g (90%) of 8a. $^1$H NMR (500 MHz, KOD (1.3 wt % in D₂O), 85° C.): δ=8.23 (d, 2H, 3J(H,H)=7.5 Hz; Ar—H), 8.15 (d, 2H, 3J(H,H)=7.0 Hz; Ar—H), 7.84 (d, 2H, 3J(H,H)=8.0 Hz; Ar—H), 7.78 (d, 2H, 3J(H,H)=8.0 Hz; Ar—H), 4.86 (s, 2H; CH2) ppm.

Glycine monoimide 8a (0.898 g, 1.999 mmol) and 1-methyl-2-pyrrolidinone (NMP, 60 mL) were heated to about 140° C. 3,4-Diamonobenzoic acid (2.509 g, 15.994 mmol) diluted in NMP (~40 mL) was added into the hot solution. After stirring at about 140° C. for 6 hours, the reaction mixture was allowed to cool to RT. 2 N HCl (50 mL) was added to the resulting mixture and a precipitate formed. The precipitate was collected by vacuum filtration and then dried under vacuum overnight. The solid was resuspended in hot DMSO. After stirring in hot DMSO for 6 hours, the mixture was filtered when it was hot. The solid obtained was washed with 2 N HCl (~100 mL) and hot water (~100 mL) and then dried under vacuum to yield a total of 0.999 g (88%) of the acid form of Va (as a mixture of two isomers). $^1$H NMR (500 MHz, D₂SO₄, a mixture of two isomers): δ=8.80 (s, Ar—H), 8.38 (Ar—H), 8.30 (Ar—H), 8.20 (Ar—H), 7.97 (s, Ar—H), 7.82 (Ar—H), 7.39 (Ar—H)— (all seven peaks integrate to 11H), 4.57 (s, 2H; CH₂) ppm. This mixture was converted to Va and Vb by reaction with KOH (aq) and NH₄OH (aq), respectively.

Alternatively, the dipotassium salt Va was converted to the diammonium salt Vb according to the following procedure. The dipotasium salt Va (0.9 g, 1.4026 mmol) was stirred with water (100 mL) at 90° C. for about 1 hour. 2 N HCl (aq, 50 mL) was added to acidify the solution. The resulting purple solid was collected by vacuum filtration. The purple residue was washed with hot water (200 mL). The residue was redissolved in ammonium hydroxide (30% NH₃, aq). The water and ammonia were evaporated to yield the solid form of the ammonium salt (Vb). Yield: 0.79 g, 1.32 mmol, 94%.

The monopotassium salt (1b) of PTCDA (3.366 g, 7.51 mmol) was suspended in hot (100° C.) DMSO (100 ml). A solution of L-valine (3.553 g, 30.03 mmol) and 87.6% KOH (1.992 g, 30.03 mmol) in water (~50 mL) was added to the hot suspension drop-wise. The hot reaction mixture was stirred for another 3 hours at about 100° C. Water (50 mL) was then added to the resulting hot reaction mixture and the mixture was filtered. The filtrate was acidified by 2 N HCl (~50 mL) and was stirred at ~90° C. for 1 hr. The precipitate formed was filtered and resuspended in DMSO (~100 mL) at 100° C. for 2 hr. After cooling to RT, the mixture was filtered. The resulting residue was washed with hot water and methanol. The purplish brown solid (8b) was then dried under vacuum at 100° C. overnight to yield 2.707 g (74%). $^1$H NMR (500 MHz, [D]DMSO, 100° C.): δ=8.72 (d, 2H, $^3$J (H,H)=7.0 Hz; Ar—H), 8.70 (d, 2H, $^3$J (H,H)=9.5 Hz; Ar—H), 8.51 (d, 2H, $^3$J (H,H)=8.0 Hz; Ar—H), 8.44 (d, 1H, $^3$J (H,H)=6.5 Hz; α-CH), 5.24 (d, 1H, $^3$J (H,H)=9.0 Hz; α-CH—), 2.79 (unresolved multiplet, 1H; β-CH—), 1.28 (d, 3H, $^3$J (H,H)=6.5 Hz; CH₃), 0.84 (d, 3H, $^3$J (H,H)=6.5 Hz; CH₃) ppm.

Compound 8b (2.023 g, 4.116 mmol) and NMP (100 mL) were heated to 140° C. 3,4-Diamonobenzoic acid (2.582 g, 16.47 mmol), dissolved in NMP (50 mL), was added into the hot solution of 8b. The mixture was stirred at 140° C. for 3 hours. After the reaction mixture was allowed to cool to RT, about 300 mL of 2 N HCl (aq) were added. The resulting precipitate was collected by vacuum filtration. The solid obtained was resuspended in 2 N HCl (aq) (~200 ml) and stirred at 90° C. for 12 hr. The resulting purple solid was collected by vacuum filtration and dried under vacuum. The product was purified by stirring the solid (3.102 g) in 90 mL of DMSO at 140° C. for 3 hours. After cooling to RT, the precipitate formed was collected by vacuum filtration, washed with hot 2 N HCl, and then suspended in 100 mL of water under reflux overnight. The resulting purple solid was collected by vacuum filtration and dried under vacuum to yield 1.167 g (47%) of the acid form of Vc (as a mixture of two isomers). $^1$H NMR (300 MHz, [D]TFA): δ=9.59 (s, 0.8H; Ar—H), 9.21 (d, 1H, $^3$J (H,H)=8.1 Hz; Ar—H), 9.12 (d, 1H, $^3$J (H,H)=8.4 Hz; Ar—H), 9.06 (d, 1H, $^3$J (H,H)=8.8 Hz; Ar—H), 9.01 (d, 1H, $^3$J (H,H)=8.1 Hz; Ar—H), 8.90 (d, 1H, $^3$J (H,H)=4.0 Hz; Ar—H), 8.88 (d, 1H, $^3$J (H,H)=4.0 Hz; Ar—H), 8.76 (s, 0.2H; Ar—H), 8.583 (d, 0.5H, $^3$J (H,H)=8.8 Hz; Ar—H), 8.580 (d, 0.5H, $^3$J (H,H)=8.8 Hz; Ar—H), 8.06 (d, 0.8H, $^3$J (H,H)=8.8 Hz; Ar—H)—(all Ar—H peaks integrate to 11H); 5.63 (d, 1H, $^3$J (H,H)=9.2 Hz; α-CH—), 2.95 (unresolved multiplet, 1H; β-CH—), 1.39 (d, 3H, $^3$J (H,H) =6.2 Hz; CH$_3$), 0.90 (d, 3H, $^3$J (H,H)=7.0 Hz; CH$_3$) ppm.

The acid form of Vc (2.023 g, 4.12 mmol) was suspended with water (50 mL). Potassium hydroxide (0.223 g, 8.24 mmol) dissolved in 50 mL of water was added drop-wise to the suspension. The resulting purple solution was stirred overnight at RT and then vacuum filtered to remove undissolved solids. The solvent was evaporated by simple distillation under nitrogen gas (Prepure Grade) atmosphere. The resulting purple solid (acid form of Vc) was dried at 130° C. under a nitrogen atmosphere overnight to yield 1.169 g (98%). $^1$H NMR (300 MHz, [D]TFA): δ=9.63 (s, 0.5H; Ar—H), 9.24 (d, 1H, $^3$J (H,H)=8.4 Hz; Ar—H), 9.21 (d, 1H, $^3$J (H,H)=8.8 Hz; Ar—H), 9.09 (d, 1H, $^3$J (H,H)=8.4 Hz; Ar—H), 9.04 (d, 1H, $^3$J (H,H)=8.4 Hz; Ar—H), 8.94 (d, 1H, $^3$J (H,H)=3.3 Hz; Ar—H), 8.91 (d, 1H, $^3$J (H,H)=3.3 Hz; Ar—H), 8.80, (s, 0.5H; Ar—H), 8.623 (d, 0.5H, $^3$J (H,H)=8.8 Hz; Ar—H), 8.619 (d, 0.5H, $^3$J (H,H)=8.8 Hz; Ar—H), 8.01 (d, 0.5H, $^3$J (H,H)=8.8 Hz; Ar—H)—(all Ar—H peaks integrate to 11H), 5.63 (d, 1H, $^3$J (H,H)=9.2 Hz; α-CH—), 2.95 (unresolved multiplet, 1H; β-CH—), 1.39 (d, 3H, $^3$J (H,H) =6.2 Hz; CH$_3$), 0.90 (d, 3H, $^3$J (H,H)=7.0 Hz; CH$_3$) ppm.

The acid form of Vc (0.2600 g, 0.43 mmol) was placed in a 250 ml round-bottomed flask with a stirring bar. Ammonium hydroxide (50 ml, 30% NH$_3$, aq) was added to dissolve the compound. Adding ammonium hydroxide formed a purple solution (aq). To remove the ammonia and water, the solution was stirred in a 100° C. oil bath overnight under an air flow. The resulting solid (Vd) was dried under vacuum at 100° C. to yield 0.2401 g (21%).

Example 6

In this example, compounds VIa-VIe were synthesized according to procedure outlined in Scheme 5. Studies by polarized optical microscopy provided evidence that this compound exhibit lyotropic liquid-crystalline properties. In addition, compound VIa was used to illustrate a novel process of this invention for the fabrication of anisotropic fluorescent materials.

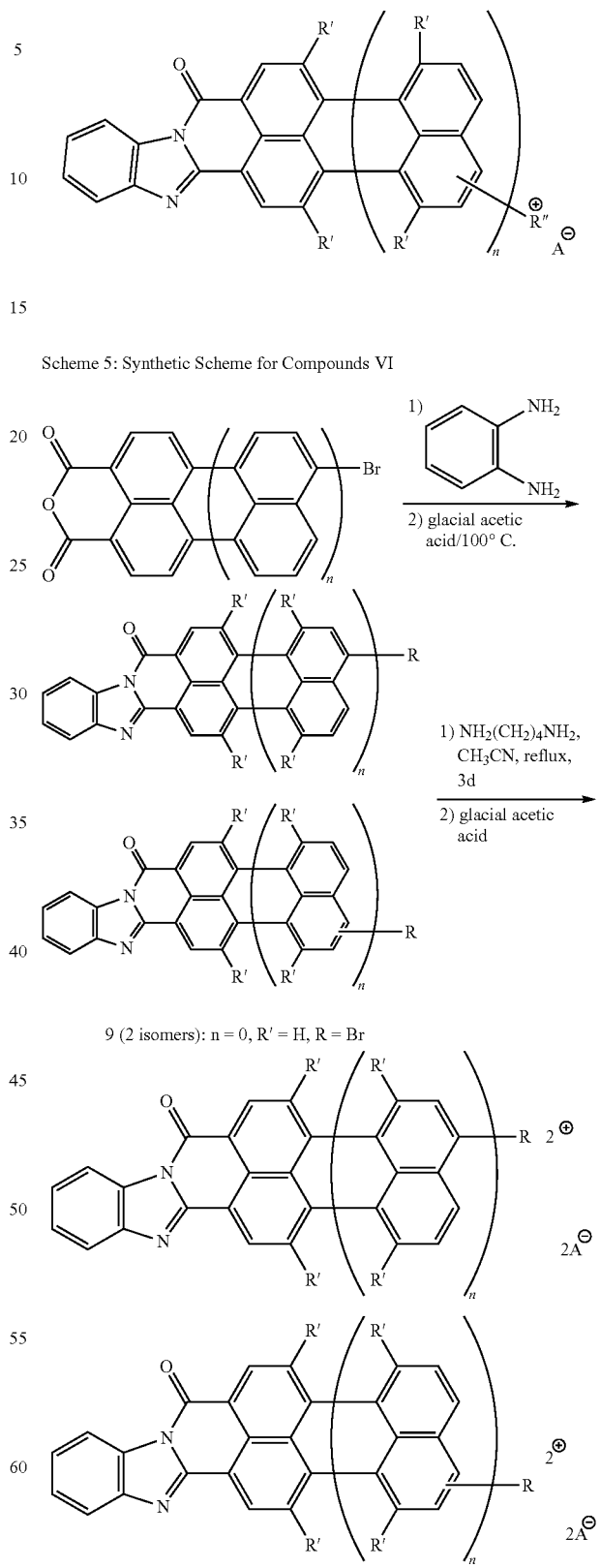

Scheme 5: Synthetic Scheme for Compounds VI

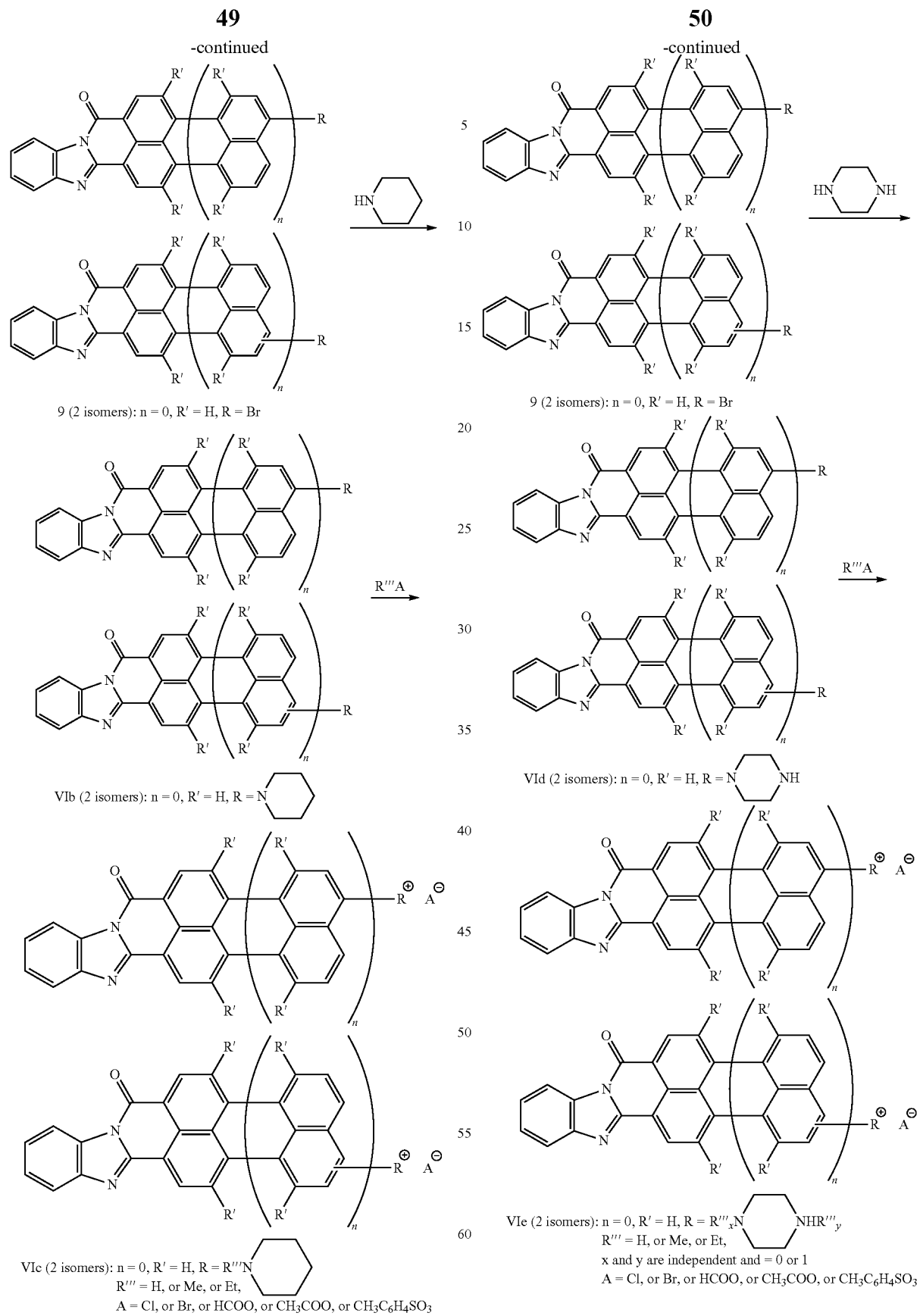
Bromonaphthyl anhydride (1.6188 g, 5.842 mmol) and o-phenylenediamine (3.2105 g, 29.69 mmol) were stirred in glacial acetic acid (75 ml) at 100° C. overnight. The mixture was then allowed to cool to RT. A yellow solid was filtered and washed with distilled H₂O. The solid was dried under vacuum overnight to yield 1.8004 g (88%). Both isomers were prepared, and the crude product (9) was used without separation of the isomers. These compounds are soluble in chloroform and benzene but the ¹H NMR was taken in deuterated trifluoroacetic acid (dTFA).

Compound 9 (0.6099 g, 1.747 mmol) and 1,4-diaminobutane (1.5882 g, 18.02 mmol) were stirred in refluxing acetonitrile (10 ml) for 3 d. The solution was allowed to cool to RT and an orange precipitate was filtered. The orange solid was stirred in ether overnight, filtered, and dried under vacuum. The orange solid was then dissolved in 15 ml of glacial acetic acid and dripped into 150 ml of hexane, causing an orange solid to precipitate. The orange solid, VIa, was collected by filtration, washed with hexane, and dried by aspiration to yield 0.1082 g (0.227 mmol, 13%). This compound is soluble in distilled water. It forms a liquid crystal at a concentration of 7.6% (w/w) in water. ¹H NMR (300 MHz, [D]TFA): δ=9.17 (2H; Ph-H), 8.91 (2H; Ph-H), 8.78 (1H; naph-H), 7.95 (1H; naph-H), 7.8-7.9 (2H; naph-H), 6.76 (2H; —NH₃⁺), 4.33 (2H; N—CH₂), 3.32 (2H; N—(CH₂)—), 2.15 (3H; CH₃COO), 1.95 (4H; CH₂) ppm.

Compounds VIb, VIc, VId and VIe are made employing compound 9 and the indicated amines as indicated in Scheme 5.

Compounds of formula VI (where n=1), for example:

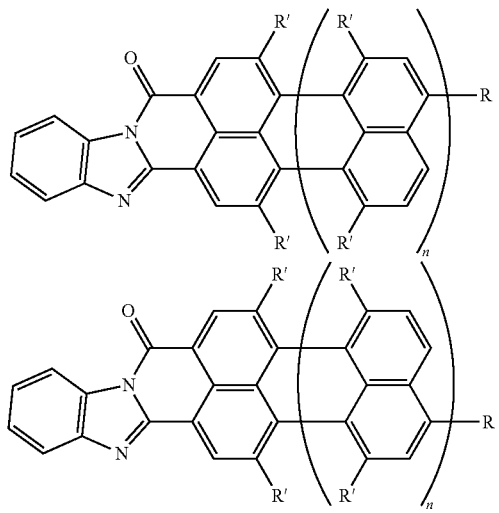

are synthesized by methods similar to those used to synthesize compounds of formula III employing an intermediate generated by modification of a step of the synthesis of Scheme 1. In the second step in the conversion of intermediates 1 to 2, in Scheme 1, the amine RNH₂ is replaced with 1,2-phenylenediamine or 1,8-naphthalene diamine. Decarboxylation, followed by bromination gives a product that has the structure of 9 (n=1), instead of 5. Substitution of Br in 9 by amines as shown in Scheme 5 is employed to generate compounds VI (n=1).

Example 7

In this example, compounds VIIa-k were synthesized. Studies by polarized optical microscopy showed that these compounds exhibit lyotropic liquid-crystalline properties. In addition, compound VIIa was used to illustrate a novel process for the fabrication of anisotropic fluorescent materials.

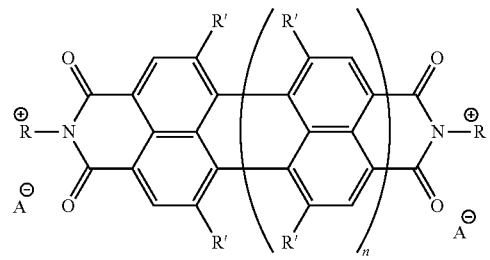

VIIa: n = 1, R′ = H, R = CH₂CH₂NHEt₂, A = Cl or HCOO;
VIIb: n = 1, R′ = D, R = CH₂CH₂NHEt₂, A = Cl or HCOO;
VIIc: n = 1, R′ = H, R = CH₂CH₂NH₃, A = Cl or HCOO;
VIId: n = 1, R′ = H, R = CH₂CH₂CH₂NHMe₂, A = Cl or HCOO;
VIIe n = 1, R′ = H, R = CH₂CH₂CH₂NHBu₂, A = Cl or HCOO;
VIIf: n = 1, R′ = H, R = CH(CMe₂)CH₂NMe₂, A = Cl or HCOO;
VIIg: n = 1, R′ = H, R = CH₂CH₂NH₂(CH₂CH₂NH₃)₂, A = Cl or HCOO;
VIIh: n = 1, R′ = H, R = (CH₂)₃NHMe(CH₂)₃NH₃, A = Cl or HCOO;
VIIi: n = 1, R′ = H, R = CH₂CH₂NMeEt₂, A = 4-MePhSO₃
VIIj: n = 1, R′ = H, R = CH₂CH₂NMeEt₂, A = I
VIIk: n = 1, R′ = H, R = (CH₂)₃N(Me)₂(CH₂)₃NH₂Me, A = 4-MePhSO₃

Perylene-3,4:9,10-tetracarboxylic dianhydride (PTCA) and the desired amine were heated at about 140° C. for a day. After the mixture was cooled to about 80° C., methanol was added. After heating for an additional 30 minutes, the solid was filtered and rinsed with organic solvents such as methanol and diethyl ether. The solid was dried under vacuum. The dried solid was then dissolved in the desired acid (e.g., HCl (aq) or HCOOH (aq)), and any undissolved particles were filtered. Upon addition of organic solvents (e.g., ethyl ether or 2-butanone) to the filtrate, compounds VIIa-VIIh precipitated from solution. The solids were filtered and dried to give compounds VIIa-VIIh.

Bis-(N,N-diethylaminoethyl)perylene-3,4,9,10-tetracarboxylic diimide (2.00 g, 3.40 mmol, neutral form of compound VIIa) was added to a 100-mL round-bottomed flask. 25 mL of methyltoluene sulfonate (166 mmol, 49 equiv.) was added and the solution was allowed to stir at room temperature or with heating for several hours. This solution was added to 100 mL of diethyl ether. The solid precipitate was allowed to settle and the ether was decanted. 100 mL of methanol (MeOH) was then added and the solid completely dissolved. Ether was then added carefully to the top of the methanolic solution. The solid that formed was slowly filtered, washed with excess ether, and dried. A total of 2.84 g of VIIi was obtained. To further purify VIIi, 1.340 g of the product was added to 40 mL of MeOH without heating or sonicating. The solution was filtered and the filtrate was evaporated using a rotary evaporator. Drying the residue under vacuum produced 0.907 g of dark red solid (58% yield). ¹H NMR (300 MHz, CF₃COOD): δ=8.85, (overlapping doublets, 8H; H-1,2), 7.65 (d, 4H, J=8 Hz; H-10), 7.20 (d, 4H, J=8 Hz; H-9), 4.77 (m, 4H; H-3), 3.70 (m, 4H; H-4), 3.55 (q, 8H, J=6.8 Hz; H-5), 3.22 (s, 6H; H-7), 2.27 (s, 6H; H-8), 1.53 (t, 12H, J=6.8 Hz; H-6) ppm; ¹³C NMR (75 MHz, CD₃OD): ∂=163.49, 144.31, 141.85, 133.74, 131.52, 131.48, 130.14, 128.11, 127.24, 124.57, 122.09, 58.64, 57.06, 34.68, 21.57, 9.41, 8.55 Ppm; UV (H₂O, 1.7×10⁻⁷ M) λ_max=533 (ε=34500), 500 (ε=31000), 469 (sh. ε=13400)nm; IR (KBr) 1695 (sharp, C=O stretch), 1656 (sharp, C=O stretch), 1593 (sharp, C=C stretch), 1440 (w), 1401 (w), 1362 (sharp, C—N stretch), 1195 (broad, strong, Ar—SO3— stretch), 1119 (m), 1032 (m), 1010 (m), 810 (m, perylene C—H wag), 747 (w, perylene C—H wag), 680 (m), 566 (m) cm$^{-1}$.

Similarly, compound VIIk was prepared from the neutral form of VIIh. Compound VIIj was prepared from the neutral form of VIIa using methyl iodide instead of methyltoluene sulfonate.

Example 8

Compound VIIi (Scheme 6) was used as an example to illustrate the novel method of this invention for preparation of anisotropic solids without using a mechanical shearing force. In this method, an isotropic solution of VIIi in water was concentrated slowly, a lyotropic chromonic liquid-crystalline phase develops and results in the formation of wire-like structures in which the mesogens are anisotropically oriented. A slab of polydimethylsiloxane (PDMS) that has a regular pattern of line features was used as the template. The use of PDMS molds in the micromolding of isotropic organic polymers[22] and fluidic alignment of inorganic materials have been reported previously.[23]

Mesogen VIIi possesses a number of useful properties. The mesogen is dichroic, fluorescent, semiconducting, and photoconducting and is thermally and photochemically stable.[24-29] The control of the molecular orientation of VIIi in solids of micrometer dimensions provides useful optical or electronic properties that are unique to anisotropic materials.

glass slide was concentrated by allowing water to evaporate from the edge of the sample under a cover-slip. When viewed between crossed polarizers (FIG. 4A), birefringent droplets (bright regions) isolated from each other in the isotropic bulk (black background) emerged, indicating the development of a liquid-crystalline phase. FIG. 4B is a larger scale optical micrograph showing the development of a chromonic LC phase from an isotropic solution of VIIi (about 20 wt % in water). Upon further evaporation of solvent, these droplets grew into long ribbon-like structures (FIG. 4B). On the glass substrate, the liquid crystalline ribbons grew in random directions.

Examination of the sample through a single polarizer (FIG. 4C, middle and right) revealed that the isotropic solution showed direction-independent absorption of blue and green light, resulting in the observed pink color for the solution. However, the ribbon-like regions exhibited anisotropic absorption of light. Regions in which the direction of growth of the ribbons was perpendicular to the polarization axis of the light absorbed blue and green light. This resulted in more intense red color compared to the isotropic solution. Regions in which the direction of growth of the ribbons was parallel to the polarization axis of the light, transmitted visible light and appeared as almost white in color. These results indicate that the principle axis of the electronic transition (that is aligned with the long axis of the molecule)[32] of VIIi in the ribbon-like regions is oriented perpendicular to the direction of growth of the ribbons.

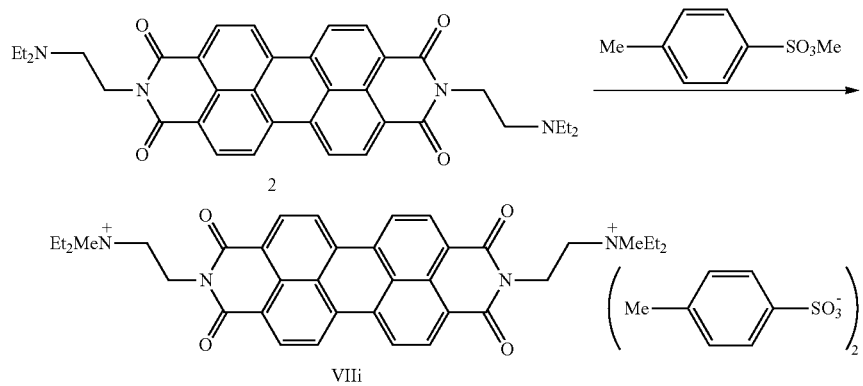

Scheme 6

Visible absorption spectra shown in FIG. 3 indicate that the electronic transition properties of VIIi vary with its concentration in water. At low concentration (e.g., $1.5 \times 10^{-7}$ M), the visible absorption spectrum of VIIi shows two intense peaks at about 535 nm and 500 nm with a shoulder at ~470 nm. With increasing concentration, the peak at 535 nm decreases in relative intensity, while the peak at 500 nm is broadened and increases in relative intensity. At $1.5 \times 10^{-4}$ M, the spectrum shows a very broad peak with a $\lambda_{max}$ at ~500 nm and shoulders at ~545 and 470 nm. These changes in the electronic transition properties are indicative of intermolecular interactions among the aromatic rings and therefore indicate aggregation of VIIi as the concentration of the aqueous solution increases. In the concentration range studied, VIIi was observed to transmit light at wavelengths longer than 600 nm (orange and red colors).

The formation of a chromonic liquid-crystalline phase at high concentrations of VIIi was confirmed by polarized optical microscopy. An aqueous solution of VIIi (~20 wt %) on a To control the width and the direction of growth of the chromonic ribbons, an isotropic solution of VIIi (~20 wt %) in water was added to a PDMS template that had regular line features that were ~9 μm in width, 2 μm in depth, and ~11 μm apart (FIG. 1). The self-organization of VIIi on the template upon slow evaporation of solvent (from under the edge of the glass cover-slip) was monitored by polarized optical microscopy (FIGS. 5A-D).

When the sample was viewed between crossed polarizers, birefringent optical textures developed, indicating the formation of a liquid-crystalline phase from the isotropic solution on the PDMS template. When viewed with a single polarizer (polarization axis parallel to the line features), the ribbon-like structures were very light pink in color as compared to the isotropic solution (FIG. 5A). In contrast, when the polarization axis of the polarized light was perpendicular to the lines, the ribbons were an intense red in color (FIG. 5B). These results show that the mesogens in the liquid-crystalline ribbons are anisotropically oriented and absorb light (blue and green) polarized perpendicular to the line features. Upon further evaporation of solvent, the entire solution became completely liquid-crystalline and anisotropic (FIGS. 5C and 5D). The electronic transition moments of the molecules are oriented perpendicular to the long dimension of the line feature. After the solid was formed, the PDMS template was peeled off of the glass cover slip. The optical micrographs of the micropattern of the anisotropic solid that was transferred to the cover-slip are shown in FIGS. 5E and 5F. These oriented solids exhibit anisotropic optical properties and can be used as micro-sized polarizers.

From an examination of the optical images of the molded solid, for the ~9 μm wide line features in the molded solid, the width and the spacing of the solid lines prepared deviated less than 10% from the width and the spacing of the features of the mold.

Similar experiments were performed using a PDMS template that had regular line features that were 2 μm in depth, 2 μm in width, and 2 μm apart. Although the fabrication conditions (e.g., the concentration of the solutions, the rate of evaporation, and the cleaning of template and glass substrates) have not yet been optimized, the results (FIG. 6) demonstrate that anisotropic materials having feature sizes as small as 2 μm can be prepared using the template guided method of this invention.

Similar experiments were performed and demonstrated that anisotropic solids having feature sized of about 600 nm can be prepared using the methods of this invention.

The method of this example was exemplified by generating anisotropic solids on glass substrates. As noted above, a variety of substrates can be employed. When glass substrates are employed the glass surface upon which the solid is to be generated is preferably washed prior to contact with the template and solution. The glass surface can simply be, washed with first with deionized water followed by an ethanol wash or a more vigorous cleaning can be done with concentrated sulfuric acid or hydrogen peroxide followed by rinsing sequentially with deionized water and ethanol.

Example 9

Compounds IIIb, IVe, and VIIa, which are defined above, were used as examples to illustrate that the mesogens self-organize into fiber-like or ribbon-like structures in the chromonic liquid-crystalline phase and in the solid phase. The molecules in the fiber-like or ribbon-like structures are anisotropically oriented, although the fiber-like or ribbon-like structures develop in random directions in the absence of a template.

FIG. 7A is an optical micrograph (400×) showing the fiber like chromonic LC structures developed slowly from a solution of IIIb (4.9 wt % in 5 vol % formic acid) on a glass substrate. The sample was viewed between crossed polarizers.

FIG. 7B is an optical micrograph (200×) showing the ribbon-like chromonic LC structures developed slowly from a solution of IVe (2 wt % in 5 vol % formic acid) on a glass substrate. The sample was viewed between crossed polarizers.

Similar fiber-like solids of compound VIIa (HCOO— as counterion) are formed on glass slides under a cover glasses. A ribbon-like or fiber-like solid was formed when an isotropic aqueous solution of VIIa (8.6 wt % in water) was concentrated by slow evaporation of solvent under a cover glass to give anisotropically oriented solid fibers. The samples were found to be birefringent.

Example 10

Compound IIIa was also used to illustrate the method of this invention to prepare anisotropic materials from lyotropic chromonic liquid crystals without using a mechanical shearing force to coat the liquid-crystalline materials onto a substrate surface. In this method, the chromonic mesogens self-organize within a template onto a glass substrate to form an anisotropic solid.

In this example, polydimethylsiloxane (PDMS) was used as the template material though materials (e.g. glass, other polymers, metals, and inorganic solids) other than PDMS can also be used. In this example, a PDMS substrate with regular line patterns was used; however, substrates with features that may or may not be in a regular pattern can be used. The steps of the process are as illustrated in FIG. 1. A solution of the mesogen was added to the template which also served as a container of the solution. A glass substrate was placed over the template. Slow evaporation of solvent resulted in the self-organization of the mesogen and formation of ribbon-like or wire-like chromonic liquid-crystalline structures (in which the mesogens are anisotropically oriented) in the patterned features of the substrate. Anisotropic solids are obtained by sufficient solvent removal. The anisotropic solid formed in the template can be transferred to the glass cover substrate by peeling off the template.

Optical micrographs showed the formation of an anisotropic solid of compound IIIa on a glass cover slip in the form of lines of solid material. The anisotropic material was formed by slow evaporation of an isotropic solution of IIIa that was added to a PDMS template with 2 μm line features. The PDMS template was removed after the sample was dried leaving the anisotropic solid of IIIa adhered to the glass. The polarization axis of the polarizer was parallel to the line features.

Example 11

Compound IIId was also used to illustrate the method of this invention to prepare anisotropic materials from lyotropic chromonic liquid crystals without using a mechanical shearing force to coat the liquid-crystalline materials onto a substrate surface. Cooling of a hot aqueous solution of IIId in an isotropic solution or in a lyotropic liquid-crystalline phase or concentration of the solutions by evaporation of solvent results in the formation of rod-shaped anisotropic solids. The rod-shaped anisotropic crystals showed direction-dependent absorption of light.

Optical micrographs showed the formation of a micropattern of an anisotropic solid of IIId on the glass cover slip. The anisotropic material was formed by slow evaporation of an isotropic solution of IIId (~12 wt % in 2% formic acid) that was added to a PDMS template with 2 μm line features. The PDMS template was removed after the sample was dried leaving the anisotropic solid of IIId adhered to the glass substrate. The polarization axis of the polarizer was parallel to the line features.

Compound IIIb was also used to illustrate the method of this invention to prepare anisotropic materials from lyotropic chromonic liquid crystals (as in FIG. 1) without using a mechanical shearing force to coat the liquid-crystalline materials onto a substrate surface. The fluorescent chromonic mesogen self-organize within a template onto a glass substrate to form an anisotropic solid that exhibits direction-dependent emission of light.

Optical micrographs showed that the micropattern (~9 μm lines) of IIIb exhibited anisotropic fluorescence emission of light. The sample was viewed under a fluorescence microscope equipped with a filter block that transmitted incident light of wavelengths from 530-560 nm and emission light from 573-648 nm. The polarization axis of the polarizer was parallel to the line features. FIG. 10B is an optical micrograph when the polarizer was rotated 90°.

Example 11

Compound IVe and a mica substrate were also used to illustrate the method of this invention to prepare anisotropic materials from lyotropic chromonic liquid crystals without using a mechanical shearing force to coat the liquid-crystalline materials onto a substrate surface as in FIG. 1. In this method, a chromonic mesogen self-organized within a PDMS template onto a mica substrate to form an anisotropic solid that exhibits direction dependent emission of light.

Optical micrographs showed the formation of an anisotropic solid of IVe on a mica substrate. The anisotropic material was formed by slow evaporation of an isotropic solution of IVe (~3 wt % in 7 N formic acid) that was added to a PDMS template with ~9 μm line features. The PDMS template was removed after the sample was dried leaving the anisotropic solid of IVe adhered to the mica substrate. The polarization axis of the polarizer was found to be perpendicular to the line features.

Example 12

A cyanine dye was used to illustrate the method of this invention to prepare anisotropic materials by self-organization of hydrophilic or ionic organic compounds without using a mechanical shearing force to coat the liquid-crystalline materials onto a substrate surface as in FIG. 1. In this method, the cyanine dye self-organizes within a PDMS template onto a glass substrate to form an anisotropic solid that exhibits direction dependent emission of light.

Optical micrographs showed the formation of anisotropic solids of pinacyanol chloride on a glass substrate. Anisotropic fibers are formed by slow evaporation of an isotropic solution of pinacyanol chloride (~15 wt % in 16.7 N formic acid) on a glass substrate without any template. When the long axis of the fibers are aligned with the axis of polarization of light, the fibers are blue in color, when long axis of the fibers are perpendicular to the axis of polarization of light, the fibers are purplish pink in color. The fibers were found to be birefringent.

Optical micrographs of a micropattern of solid cyanine dye prepared by the method of this invention showed that an anisotropic solid was formed. The anisotropic material was formed by slow evaporation of an isotropic solution of pinacyanol chloride (~15 wt % in 16.7 N formic acid) that was added to a PDMS template with 2 μm line features. The PDMS template was removed after the sample was dried leaving the anisotropic solid adhered to the glass substrate. The polarization axis of the polarizer was found to be parallel to the line features. The anisotropic solid lines appeared blue in color. When the polarizer was rotated 90°, the anisotropic solid lines appeared purplish pink in color.

Example 13

This example describes anisotropic solid films formed by shear-induced alignment that are composed of a mixture of chromonic mesogens of this invention. The use of multi-component liquid-crystalline materials allows the generation of anisotropic films that linearly polarize light over a much wider spectrum of wavelengths and broadens their potential utility. Films such as those exemplified in this example, which polarize visible light can, for example, be employed as components of liquid-crystal displays. The method of this example can be applied to mixtures of two, three or more mesogens. The method is illustrated using compounds Ia and IVa (compound of formula IV-1, where n and q=0, R is —$(CH_2)_2$—$N(Et)_2H^+$, R" is H, and C is $HCOO^-$).

The criteria for the structural design of the molecules used to fabricate broad spectrum polarizers include the following: (1) The difference in the surface areas of the aromatic regions of the components (as shown by Ia and IVa) is not too large to preclude the formation of mixed aggregates of these compounds by solvophobic interactions and π-stacking. The formation of mixed aggregates (instead of self-aggregates) minimizes large regions of inhomogeneous color in the polarizing films. (2) Components are dichroic and the principle electronic transition axes align with the long molecular axes to ensure that their mixed aggregates and the anisotropic films produced subsequently exhibit direction-dependent optical properties. (3) Components display chromonic liquid-crystalline properties in a common aqueous solvent permitting shear-induced alignment (or alignment without mechanical shearing (as in FIG. 1) employing methods exemplified in Example 8 and others herein). (2) The component compounds are preferably selected (such as Ia and IVa have been) to possess different aromatic ring systems that absorb at different wavelengths, so that their mixtures absorb over a large wavelength range.

The control of solubilities and chromonic liquid-crystalline properties of compounds like Ia and IVa can be achieved by adjusting the number of bulky ionic groups attached to their aromatic rings. Compounds Ia and IVa were synthesized according to the procedure described in the above examples. When compounds Ia and IVa were dissolved separately in 16.5 NHCOOH (aq), the visible absorption spectra of their solutions showed a blue shift in the $\lambda_{max}$ values as the concentrations of the solutions were increased from ~$10^{-7}$ to ~$10^{-4}$ M. This indicates the formation of H— aggregates by each compound when present alone in solution. However, when mixed in a mole ratio of ~1:1, red shifts in $\lambda_{max}$ values of Ia and IVa were observed, providing evidence for intermolecular interactions and the formation of mixed aggregates (probably J-aggregates) of Ia and IVa. At a concentration of about $10^{-4}$ M, the $\lambda_{max}$ value of Ia in the solution containing both Ia and IVa was almost 70-nm longer (to the red) than in the solutions of Ia alone. When a solution of both Ia and IVa at high concentration (e.g., 10 wt % of 1 and 2 combined (at ~1:1 mole ratio) in HCOOH (aq, 16.5 N) was viewed between crossed polarizers under an optical microscope, the optical textures observed were consistent with a chromonic, nematic liquid-crystalline phase. In this type of phase, the mesogens typically stack to form columns (not necessarily simple one-molecule-wide columns), but there is no positional order among the columns. Under a mechanical shearing force that spreads the liquid-crystalline solution containing both Ia and IVa onto a glass substrate, the liquid-crystalline domains are aligned and the degree of orientational order of the molecules can be extended over a substantially longer range. This order can then be transferred to the solid state upon removal of the solvent. The anisotropic optical properties of the sheared films formed from a mixture of both Ia and IVa were apparent when the films were examined by polarized optical microscopy. The films were transparent and very light in color when the polarization axis of the incident light was parallel to the shearing direction of the films. In contrast, an intense blue color was observed when the polarization axis of the incident light was orthogonal to the shearing direction.

The polarized visible spectra (in transmission mode) of a sheared film formed from a mixture of Ia and IVa, with the incident radiation normal to the film surface showed significant broadening of the spectra of the solid films compared to the spectra of the solutions, presumably because of intermolecular interactions in the solid phase. Furthermore, the oriented films exhibited intense absorption of light when the polarization axis of the incident light was perpendicular to the shearing direction, while only weak absorption occurred when the polarization axis of the incident light was parallel to the shearing direction. This indicates that the majority of the molecules on the glass substrate are oriented with their long axes orthogonal to the shearing direction, since the electronic transition moments for these transitions of both Ia and IVa are aligned with the long axes of their molecular planes. The oriented films showed anisotropic optical properties over a broad range of wavelengths (~450-890 nm); the degree of polarization of these films was typically over 80% from about 470 to 800 nm.

Polarized transmission IR spectroscopy was used to further elucidate the molecular orientation in the sheared films of the mixture of Ia and IVa. With the substrate in the XY plane and the shearing direction and the polarized IR radiation parallel to the X-axis, the C—H perylene wagging resonance will be strongest when the molecular planes of Ia and IVa are in the YZ plane. This will be the case whether the long axes of the molecules are aligned with the Y— axis or the Z-axis or something between. This molecular orientation causes the dynamic dipole vector ($\mu$) of the C—H perylene wagging mode to lie along the X-axis (the axis of polarized IR irradiation). If the average molecular planes of Ia and IVa were in the XZ plane or in the XY plane parallel to the substrate surface, the dipole vector of the C—H wagging mode would be perpendicular to the axis of polarized IR radiation, and the C—H wagging resonance would not be observed. When the shearing direction of the film and the electric vector of IR polarization were parallel, the out-of-plane C—H wagging resonances of Ia and IVa at about 750-810 $cm^{-1}$ were greatly enhanced in intensity relative to the normally dominant in-plane stretches at 1570-1690 $cm^{-1}$. Upon rotation of the sheared sample 90°, so that the shearing direction was perpendicular to the electronic vector of the incident IR radiation, the opposite effect was seen as all of the in-plane imide and aromatic stretches (1570-1690 $cm^{-1}$) of Ia and IVa increased in relative intensity, while the peaks at 750-810 $cm^{-1}$ almost disappeared. These results indicate that the molecular planes of Ia and IVa in these oriented films are aligned with the YZ plane. The studies by polarized visible spectroscopy discussed above show that the long molecular axes of Ia and IVa align with the Y axis, although the results cannot exclude the possibility that the long axis of some molecules in the films are aligned with the Z axis.

Dichroic mesogens Ia and IVa absorb at very different wavelengths and yet display chromonic liquid-crystalline properties in a common aqueous solvent. These properties allowed the induced orientation of the mixed liquid crystals by a mechanical shearing force and subsequently produced solid films that exhibit anisotropic optical properties over a broad spectrum. The design principles for mixed chromonic liquid crystals illustrated in this example are broadly applicable to other mesogens and other alignment techniques, including methods exemplified herein in the examples herein, as well as methods relying on the induced orientation of chromonic liquid crystals by photoaligned polymers (See: Matsunaga, D.; Tamaki, T.; Akiyama, H.; Ichimura, K. Adv. Mater. 2002, 14, 1477 and Ichimura, K.; Fujiwara, T.; Momose, M.; Matsunaga, D. J. Mater. Chem. 2002, 12, 3380) can be used to make anisotropic solids containing two or more orienting compounds.

Additional details of this example can be found in S-W. Tam-Chang, W. Seo, K. Rove and S. M. Casey (2004) "Molecularly Designed Chromonic Liquid Crystals for the Fabrication of Broad Spectrum Polarizing Materials" Chem. Mater. 16:1832-1834.

Example 14

In this example, anisotopic micropatterns of two different compounds (IIIb and IVe) were developed on opposite surfaces (side 1 and side 2) of a substrate (see FIG. 2C). A glass coverslip was used as a substrate. A solution of compound IIIb was prepared in situ by dissolving compound 5 (~15 wt %) in formic acid (~7N) and a solution of compound IVe was prepared in situ by dissolving its neutral amine (~6 wt %) in formic acid (14-17 N). The solution of IIIb was added onto a PDMS mold with micropatterned lines (channels, 20 µm in linewidth). A glass coverslip was used to cover the solution in the channels. The solvent was evaporated from the solutions over a few hours or overnight. The PDMS template was removed from the coverslip leaving a micropattern of anisotropic solid IIIb on one side (side 1 of the coverslip). The solution of IVe was then added onto another PDMS mold with micropatterned lines (20 µm in linewidth). The coverslip with the solid micropattern of IIIb was placed onto the PDMS mold in such as way that the opposite surface (side 2) (not carrying IIIb) was in contact with the PDMS template. The angle between the line pattern of the template on side 2 and the line pattern of IIIb on side 1 was selected to be 90° The solvent was allowed to evaporate from the solution of IVe over a few hours or overnight. The template was removed from the glass coverslip leaving a micropattern of anisotropic solid IVe on one side (side 2) and a micropattern of anisotropic solid IIIb on the opposite side (side 1) of the coverglass.

Optical micrographs of the substrate coated on two surfaces viewed through a single polarizer are provided as FIG. 8 A-D. The micrographs show the anisotropic orientation of IIIb and IVe in micropatterns of line features (~20 µm in linewidth) on the opposite sides the glass cover slip. The images (A) and (B) were focused at side 1 and the images (C) and (D) were focused at side 2. The polarization axis of the incident light was perpendicular to the lines of IIIb in (A) and (C) and parallel to the lines of IVe in (B) and (D).

REFERENCES

[1] D. L. Gin, W. Gu, B. A. Pindzola, W.-J. Zhou, Acc. Chem. Res. 2001, 34, 973-980.
[2] M. C. Fyfe, J. F. Stoddart, Acc. Chem. Res. 1997, 30, 393-401.
[3] J. S. Moore, Acc. Chem. Res. 1997, 30, 402-413.
[4] T. E. Mallouk, J. A. Gavin, Acc. Chem. Res. 1998, 31, 209-217.
[5] K. Campbell, C. J. Kuehl, M. J. Ferguson, P. J. Stang, R. R. Tykwinski, J. Am. Chem. Soc. 2002, 124, 7266-7267.
[6] J.-M. Lehn, Supramolecular Chemistry, VCH, Weinheim, New York, 1995.
[7] R. Shenhar, V. M. Rotello, Acc. Chem. Res. 2003, 36, 549-561.
[8] G. Pfaff, P. Reynders, Chem. Rev. 1999, 99, 1963-1981.
[9] D. Matsunaga, T. Tamaki, H. Akiyama, K. Ichimura, Adv. Mater. 2002, 14, 1477-1478.

[10] W. M. Moreau, Semiconductor Lithography: Principles and Materials, Plenum, New York, 1988.
[11] Y. Xia, G. M. Whitesides, Angew. Chem. Int. Ed. 1998, 37, 550-575.
[12] P. Yang, G. Wirnsberger, H. C. Huang, S. R. Cordero, M. D. McGehee, B. Scott, T. Deng, G. M. Whitesides, B. F. Chmelka, S. K. Buratto, G. D. Stucky, Science 2000, 287.
[13] G. Y. Liu, S. Xu, Y. Qian, Acc. Chem. Res. 2000, 33, 457-466.
[14] Y. Xia, J. A. Rogers, K. E. Paul, G. M. Whitesides, Chem. Rev. 1999, 99, 1823-1848.
[15] L. Cardillo, D. Swift, J. Meritt, J. Imaging Sci. Technol. 1998, 42, 300.
[16] J. Lydon, in Handbook of Liquid Crystals, Vol. 2B (Eds.: D. Demus, J. Goodby, G. W. Gray, H.-W. Spiess, V. Vill), Wiley-VCH, Weinheim, 1998, pp. 981-1007
[17] K. Ichimura, T. Fujiwara, M. Momose, D. Matsunaga, J. Mater. Chem. 2002, 12, 3380-3386.
[18] S. W. Tam-Chang, W. Seo, I. K. Iverson, S. M. Casey, Angew. Chem. Int. Ed. 2003, 42, 897-900.
[19] I. K. Iverson, S.-W. Tam-Chang, J. Am. Chem. Soc. 1999, 121, 5801-5802.
[20] C. Ruslim, D. Matsunaga, M. Hashimoto, T. Tamaki, K. Ichimura, Langmuir 2003, 19, 3686-3691.
[21] P. J. A. Kenis, R. F. Ismagilov, S. Takayama, G. M. Whitesides, Acc. Chem. Res. 2000, 33, 841-847.
[22] E. Kim, Y. Xia, G. M. Whitesides, J. Am. Chem. Soc. 1996, 118, 5722-5731.
[23] Y. Huang, X. Duan, Q. Wei, C. M. Lieber, Science 2001, 291, 630-633.
[24] K. Y. Law, Chem. Rev. 1993, 93, 449-486.
[25] F. Wurthner, C. Thalacker, A. Sautter, W. Schartl, W. Ibach, O. Hollricher, Chem. Eur. J. 2000, 6, 3871-3886.
[26] L. Schmidt-Mende, A. Fechtenkötter, K. Müllen, E. Moons, R. H. Friend, J. D. MacKenzie, Science (Washington, D.C.) 2001, 293, 1119-1122.
[27] A. B. Gregg, R. A. Cormier, J. Am. Chem. Soc. 2001, 123, 7959-7960.
[28] T. D. Carson, W. Seo, S. W. Tam-Chang, S. M. Casey, Chem. Mater. 2003, 15, 2292-2294.
[29] M. P. O'Neil, M. P. Niemczyk, W. A. Svec, D. Gosztola, G. L. I. Gaines, M. R. Wasielewski, Science 1992, 257, 63-65.
[30] N. V. Khromov-Borisov, M. L. Inclenbom, A. F. Danilov, Khim. Farm. Zh. 1980, 14, 15-20.
[31] I. Lykác, H. Langhals, Chem. Ber. 1983, 116, 3524-3528.
[32] M. Hasegawa, T. Matano, Y. Shindo, T. Sugimura, Macromolecules 1996, 29, 7897-7909.
[33] J. C. McDonald, G. M. Whitesides; Accounts Chem. Research 2002, 35(7), 491-499.

We claim:

1. A compound of the formula:

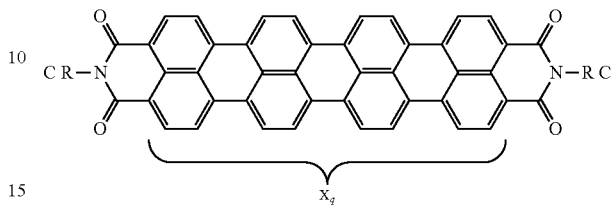

wherein:
R is a hydrophilic group or a charged group;
C, if present is a suitable counterion or counterions;
q is an integer indicative of the number of X substituents; and
each X, independent of other X in the compound, is a non-hydrogen substituent on the aromatic ring system selected from the group consisting of alkyl, alkoxy, alkyl sulfide, alkyl disulfide, cyano, isocyano, thiocyano, isothiocyano, nitro, or halogen, wherein one or more C, CH or $CH_2$ groups of the alkyl groups or alkoxy groups can be replaced with one or more of an O atom, S atoms, P atoms, a —CO— group, a —O—CO— group, a —$SO_3$— group, a —$PO_3$— group, an N atom, an $NR_1$ group, an —$NR_1$—CO— group and wherein one or more C of the alkyl or alkoxy group can be substituted with one or more halogens, hydroxyl, thiol, cyano, isocyano, thiocyano, isothiocyano or nitro groups wherein $R_1$ is an optionally substituted alkyl or aryl group; or a charged substituent where a charged X is accompanied by an appropriate counterion.

2. A solution for making an anisotropic solid which comprises one or more soluble orienting compounds of claim 1.

3. An anisotropic solid comprising one or more of the compounds of claim 1.

4. A polarizer comprising an anisotropic solid containing one more of the compounds of claim 1.

5. An optical device comprising a polarizer comprising an anisotropic solid containing one or more of the compounds of claim 1.

* * * * *